US011980383B2

(12) United States Patent
Farrow et al.

(10) Patent No.: US 11,980,383 B2
(45) Date of Patent: May 14, 2024

(54) WOUND-CARE APPARATUS AND METHOD FOR CLEANSING, DESLOUGHING, AND DEBRIDING WOUNDS

(71) Applicant: FARROW CONSULTING LLC, Charlotte, NC (US)

(72) Inventors: Wade P. Farrow, Charlotte, NC (US); Adrian Slattery, Rocky River, OH (US); Douglas R. Halley, Westlake, OH (US)

(73) Assignee: Farrow Medtech LLC, College Station, TX (US)

( * ) Notice: Subject to any disclaimer, the term of this patent is extended or adjusted under 35 U.S.C. 154(b) by 23 days.

(21) Appl. No.: 17/133,212

(22) Filed: Dec. 23, 2020

(65) Prior Publication Data

US 2021/0186552 A1 Jun. 24, 2021

Related U.S. Application Data

(60) Provisional application No. 62/953,441, filed on Dec. 24, 2019.

(51) Int. Cl.
*A61B 17/32* (2006.01)

(52) U.S. Cl.
CPC ............... *A61B 17/320068* (2013.01); *A61B 2017/320008* (2013.01); *A61B 2017/320078* (2017.08); *A61B 2217/007* (2013.01)

(58) Field of Classification Search
CPC ........... A61B 17/320068; A61B 2017/320008; A61B 2017/320078; A61B 2217/007;

(Continued)

(56) References Cited

U.S. PATENT DOCUMENTS 6,478,754 B1  11/2002  Babaev
6,569,099 B1  5/2003  Babaev
(Continued)

FOREIGN PATENT DOCUMENTS

WO    2005030297      4/2005
WO    2013072357      5/2013
WO    2014/210149 A1  12/2014

OTHER PUBLICATIONS

7 Need-to-Know Polypropylene Material Properties. Jan. 16, 2020. Coatings for Baskets and Racks. Retrieved from the Internet <URL: https://www.marlinwire.com/blog/7-need-to-know-polypropylene-material-properties#:~:text=Surface%20Hardness.,and%20flex%20with%20an%20impact. >, (Year: 2020).*

(Continued)

*Primary Examiner* — Shaun L David
*Assistant Examiner* — Rachael L Geiger
(74) *Attorney, Agent, or Firm* — Young Basile Hanlon & MacFarlane, P.C.

(57) ABSTRACT

A method of treating or cleaning a wound bed is disclosed. The method includes obtaining a wound-care device. The wound-care device includes a handle and a head monolithically formed with a first end of the handle and extending away from the first end of the handle. The head includes a base and a plurality of projections monolithically formed with the base and extending away from the base. During use of the wound-care device, a user may manually disturb a wound bed of a patient by placing one or more projections of the plurality of projections in contact with the wound bed and manually moving, while the one or more projections are in contact with the wound bed, the wound-care device with respect to the wound bed.

19 Claims, 47 Drawing Sheets

(58) Field of Classification Search
CPC ......... A61B 2017/320084; A61B 2017/00761;
A61B 2017/320004; A61B 2017/32007
See application file for complete search history.

(56) References Cited

U.S. PATENT DOCUMENTS

| | | | |
|---|---|---|---|
| 6,663,554 B2 | 12/2003 | Babaev | |
| 6,761,729 B2 | 7/2004 | Babaev | |
| 6,916,296 B2 | 7/2005 | Soring | |
| 6,960,173 B2 | 11/2005 | Babaev | |
| 7,025,735 B2 | 4/2006 | Soring et al. | |
| 7,431,704 B2 | 10/2008 | Babaev | |
| 7,572,268 B2 | 8/2009 | Babaev | |
| 7,608,054 B2 | 10/2009 | Soring | |
| 7,713,218 B2 | 5/2010 | Babaev et al. | |
| 7,785,277 B2 | 8/2010 | Babaev et al. | |
| 7,785,728 B2 | 8/2010 | Babaev | |
| D627,463 S | 11/2010 | Voic et al. | |
| 7,842,032 B2 | 11/2010 | Babaev | |
| 7,878,991 B2 | 2/2011 | Babaev | |
| 7,896,854 B2 | 3/2011 | Babaev | |
| 7,896,855 B2 | 3/2011 | Babaev | |
| 7,901,388 B2 | 3/2011 | Babaev | |
| 7,914,470 B2 | 3/2011 | Babaev | |
| 7,931,611 B2 | 4/2011 | Novak et al. | |
| D644,326 S | 8/2011 | Voic et al. | |
| 8,025,672 B2 | 9/2011 | Novack | |
| 8,050,752 B2 | 11/2011 | Babaev | |
| 8,052,705 B2* | 11/2011 | Bar-On | A61F 9/0133 606/166 |
| 8,235,919 B2 | 8/2012 | Babaev | |
| 8,277,472 B2 | 10/2012 | Babaev et al. | |
| 8,430,897 B2 | 4/2013 | Novak et al. | |
| 8,562,547 B2 | 10/2013 | Babaev | |
| D699,839 S | 2/2014 | Voic | |
| D715,434 S | 10/2014 | Darian | |
| D715,435 S | 10/2014 | Darian | |
| D715,936 S | 10/2014 | Darian | |
| D733,319 S | 6/2015 | Somers et al. | |
| 9,119,658 B2 | 9/2015 | Paraschiv et al. | |
| D741,481 S | 10/2015 | Darian et al. | |
| 9,211,137 B2 | 12/2015 | Voic | |
| 9,320,528 B2 | 4/2016 | Voic et al. | |
| 9,387,005 B2 | 7/2016 | Voic | |
| 9,421,028 B2 | 8/2016 | Darian | |
| 9,622,766 B2 | 4/2017 | Voic | |
| 9,788,852 B2 | 10/2017 | Voic | |
| 9,872,697 B2 | 1/2018 | Voic | |
| 9,949,751 B2 | 4/2018 | Voic | |
| 10,092,308 B2 | 10/2018 | Mikus et al. | |
| 10,117,666 B2 | 11/2018 | Voic | |
| 10,149,735 B2* | 12/2018 | Noell | A61B 90/80 |
| 10,219,822 B2 | 3/2019 | Voic et al. | |
| 10,299,809 B2 | 5/2019 | Mikus et al. | |
| 10,363,067 B2* | 7/2019 | Hultquist | A61B 90/20 |
| 2003/0165550 A1 | 9/2003 | Rhoades | |
| 2004/0010250 A1* | 1/2004 | R. Manna | A61B 18/1445 606/42 |
| 2004/0030254 A1 | 2/2004 | Babaev | |
| 2008/0306501 A1 | 12/2008 | Babaev | |
| 2009/0157094 A1 | 6/2009 | Yeshurun et al. | |
| 2009/0192442 A1 | 7/2009 | Ignon et al. | |
| 2011/0009694 A1* | 1/2011 | Schultz | A61B 1/317 600/109 |
| 2011/0247220 A1* | 10/2011 | Whited | A61B 17/322 30/276 |
| 2014/0330286 A1* | 11/2014 | Wallace | A61M 3/0202 606/127 |
| 2015/0148712 A1 | 5/2015 | Loven et al. | |
| 2015/0182246 A1* | 7/2015 | Grez | A45D 44/00 606/131 |
| 2016/0143660 A1* | 5/2016 | Castro | A61B 17/32 606/170 |
| 2017/0014145 A1* | 1/2017 | Favie | A61N 5/0616 |
| 2017/0072224 A1 | 3/2017 | Frohwitter | |
| 2017/0215906 A1 | 8/2017 | Derk et al. | |
| 2018/0177528 A1* | 6/2018 | Domingos | A61B 17/32 |
| 2019/0111238 A1* | 4/2019 | Schultz | A45D 44/00 606/131 |
| 2020/0179725 A1 | 6/2020 | Loven et al. | |

OTHER PUBLICATIONS

The Curason, www.curasonix.com/en/, webpage visited Sep. 14, 2021.
Translation of WO2013072357.
Written Opinion of the International Searching Authority for International Application No. PCT/US2020/067045, dated Mar. 30, 2021.
Extended European Search Report for Application No. EP 20905007.9 dated May 16, 2023.

\* cited by examiner

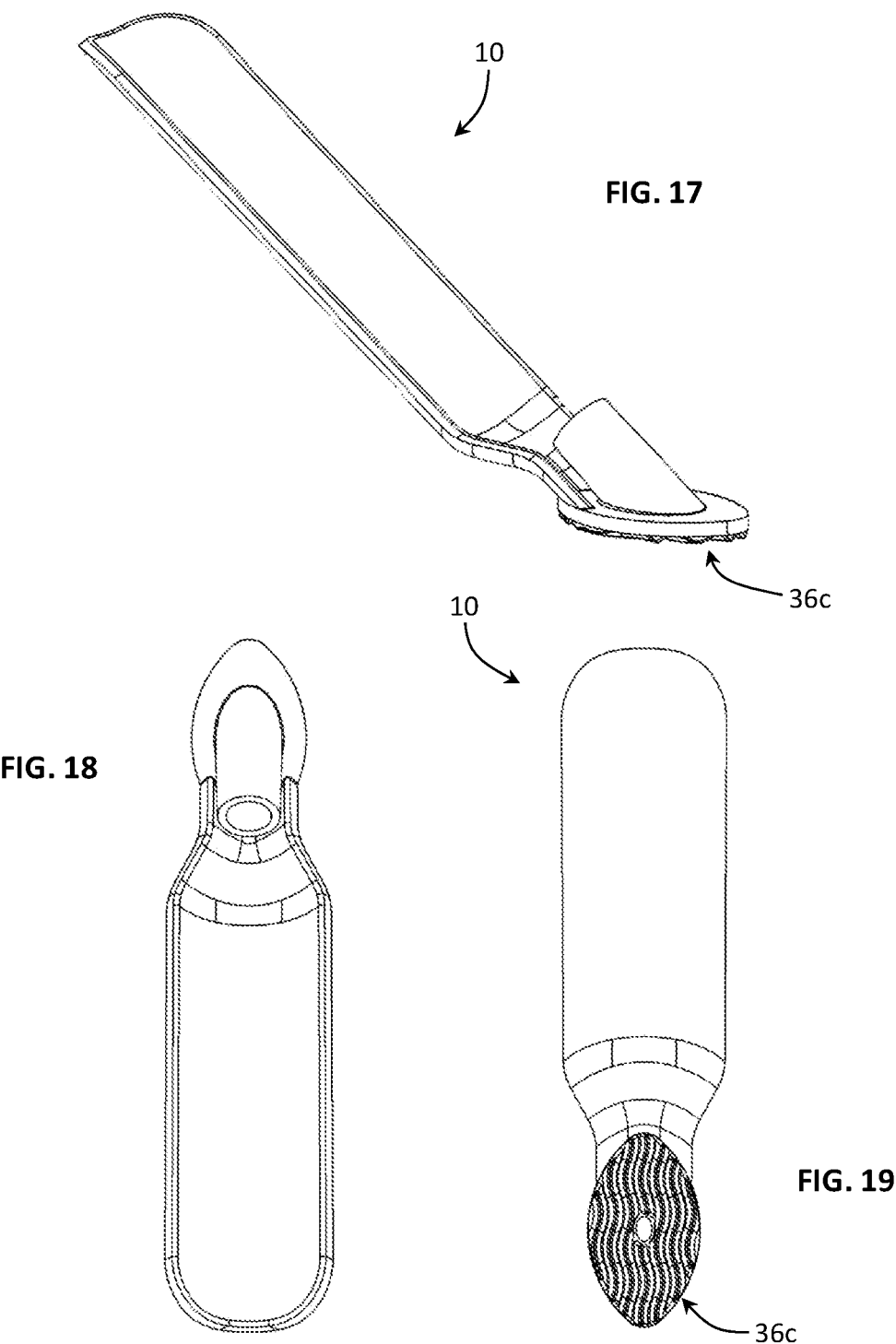

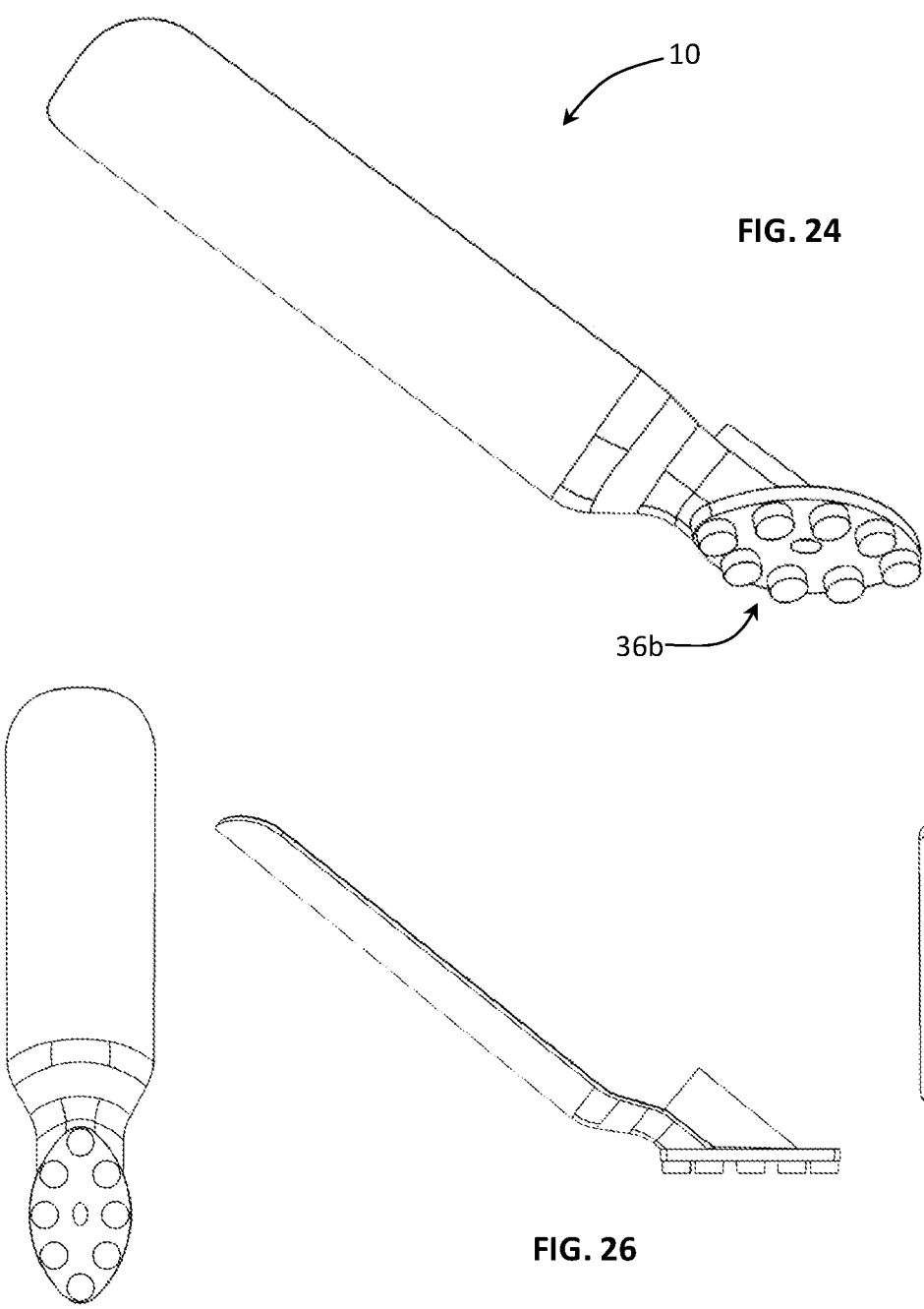

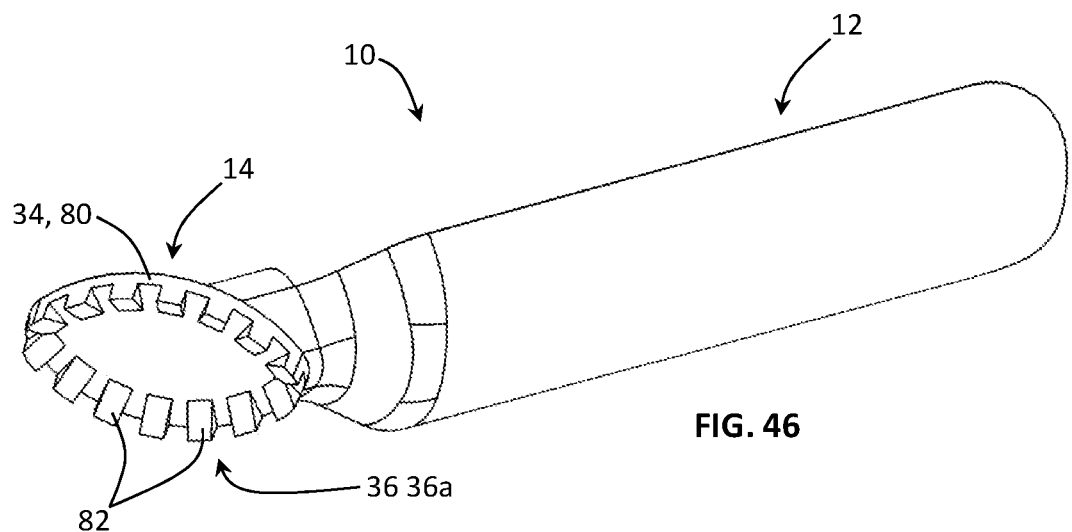
FIG. 46
FIG. 47
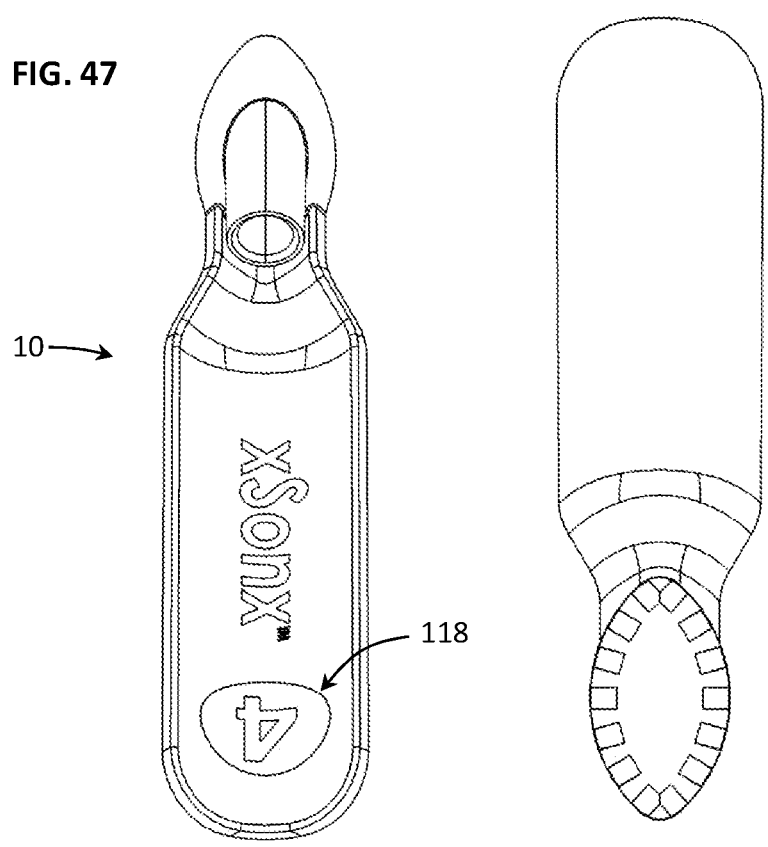
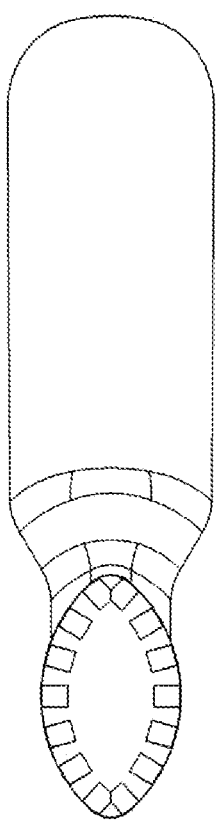
FIG. 48

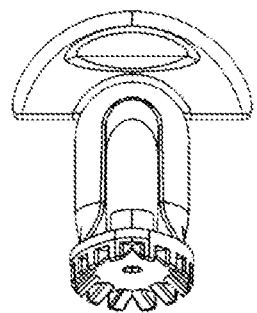
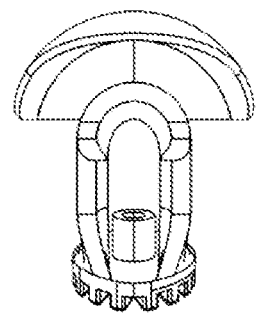
FIG. 69    FIG. 70
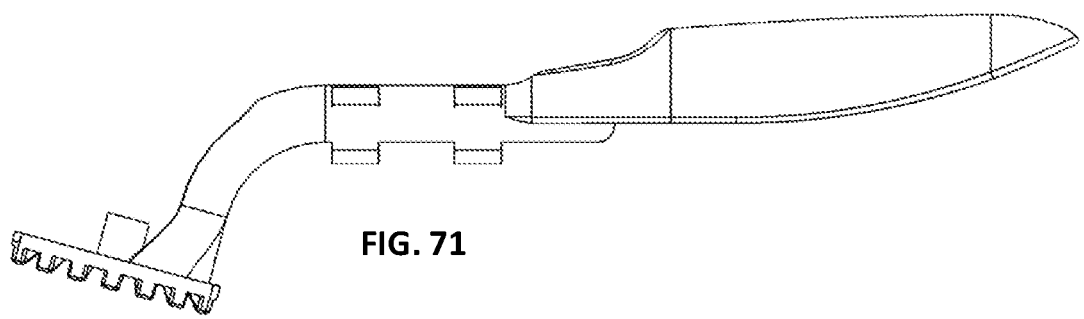
FIG. 71
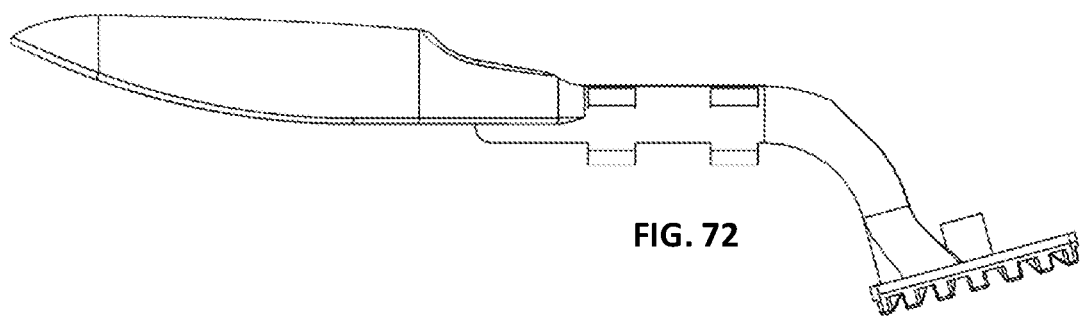
FIG. 72

WOUND-CARE APPARATUS AND METHOD FOR CLEANSING, DESLOUGHING, AND DEBRIDING WOUNDS

BACKGROUND

1. Related Applications

This application claims the benefit of U.S. Provisional Patent Application Ser. No. 62/953,441 filed Dec. 24, 2019, which is hereby incorporated by reference.

2. Field Of The Invention

This invention relates to wound care and, more particularly, to novel systems and methods for cleansing, desloughing, and debriding wounds.

3. Background Art

Different types of devitalized tissue commonly appear in wound beds. Such tissue may interrupt granulation and delay healing. For example, devitalized tissue may stimulate the overproduction of matrix metalloproteases (MMIPs) and thereby slow the healing process. Additionally, devitalized tissue may provide an environment favorable to bacteria. Bacterial biofilms grow on 60-90% of chronic wounds and about 6% of acute wounds. Bacterial biofilms are low grade infections, cause chronic inflammation, impair wound healing, and increase risk of cellulitis. Various technologies and/or methods have been developed to improve wound care. However, those technologies and/or method have certain drawbacks. For example, ultrasonic debridement (e.g., debridement involving oscillations at about 20 kHz or above) is too expensive to be widely adopted. Conversely, pulse lavage is often too untidy for use in clinic or emergency room settings. Accordingly, what is needed are improved systems and methods for cleansing, desloughing, and debriding wounds and removing bacterial biofilms.

BRIEF DESCRIPTION OF THE DRAWINGS

The present invention will become fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 17 is a perspective view of the main body and head portions of the wound-care device of FIG. 10;

FIG. 18 is a top view of the main body and head portions of the wound-care device of FIG. 10;

FIG. 19 is a bottom view of the main body and head portions of the wound-care device of FIG. 10;

FIG. 24 is a perspective view of another alternative embodiment of a wound-care device in accordance with the present invention;

FIG. 25 is a bottom view of the wound-care device of FIG. 24;

FIG. 26 is a side view of the wound-care device of FIG. 24;

FIG. 27 is a front view of the wound-care device of FIG. 24;

FIG. 46 is a perspective view of another alternative embodiment of a wound-care device in accordance with the present invention;

FIG. 47 is a top view of the wound-care device of FIG. 46;

FIG. 48 is a bottom view of the wound-care device of FIG. 46;

FIG. 69 is a front view of the wound-care device of FIG. 62;

FIG. 70 is a rear view of the wound-care device of FIG. 62;

FIG. 71 is a first side view of the wound-care device of FIG. 62;

FIG. 72 is a second, opposite side view of the wound-care device of FIG. 62;

DETAILED DESCRIPTION OF SELECTED EMBODIMENTS

Figure 1:
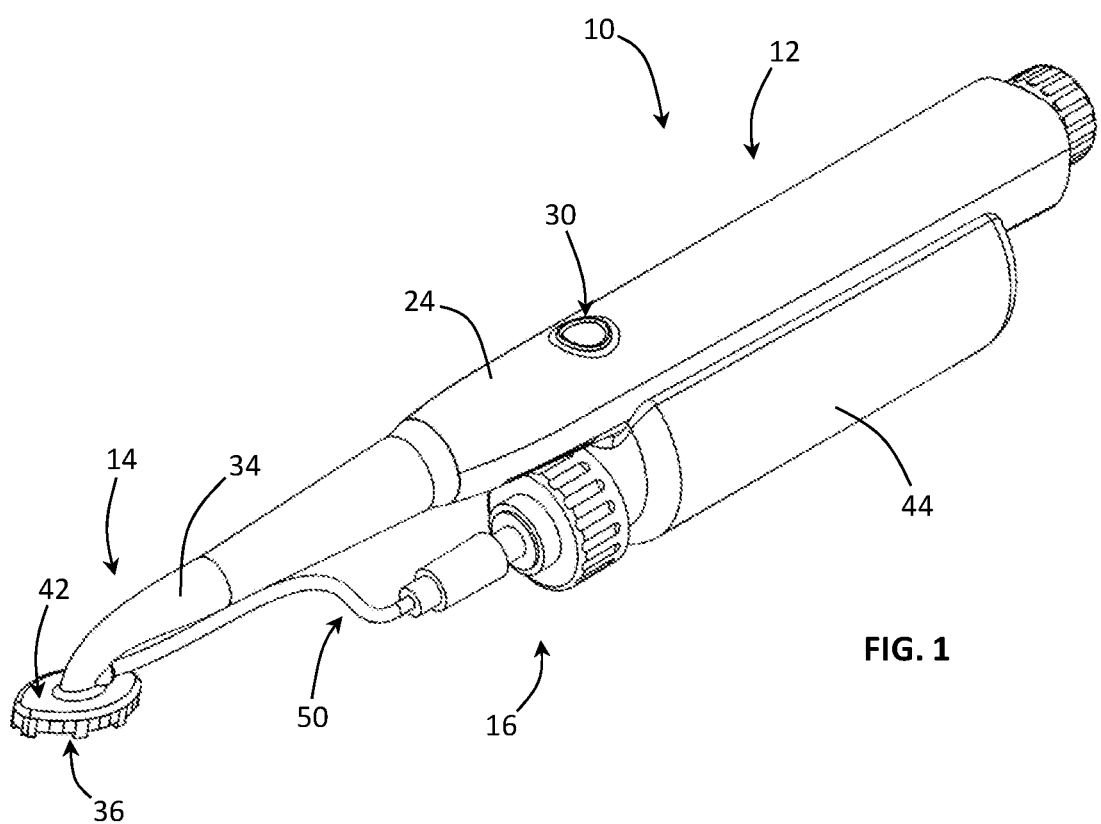
FIG. 1 is a perspective view of one embodiment of a wound-care device in accordance with the present invention.
Figure 2:
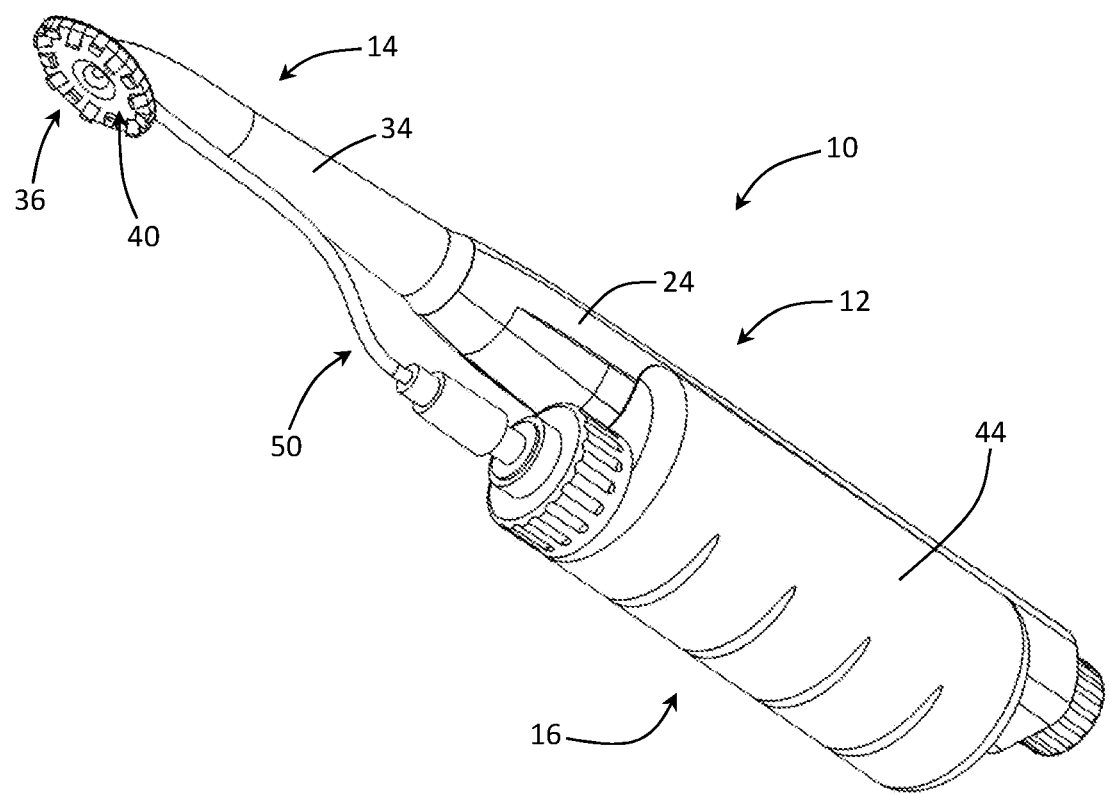
FIG. 2 is another perspective view of the wound-care device of FIG. 1.
Figure 3:
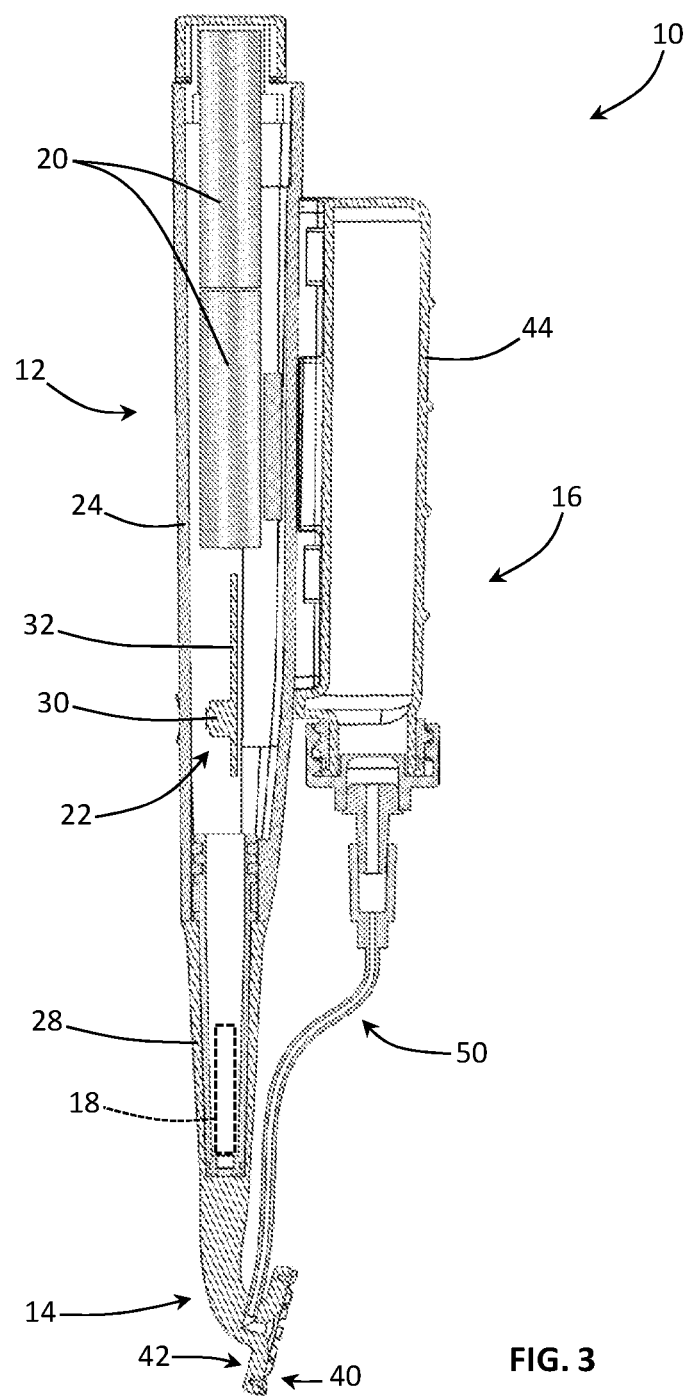
FIG. 3 is a side cross-sectional view of the wound-care device of FIG. 1.
Figure 4:
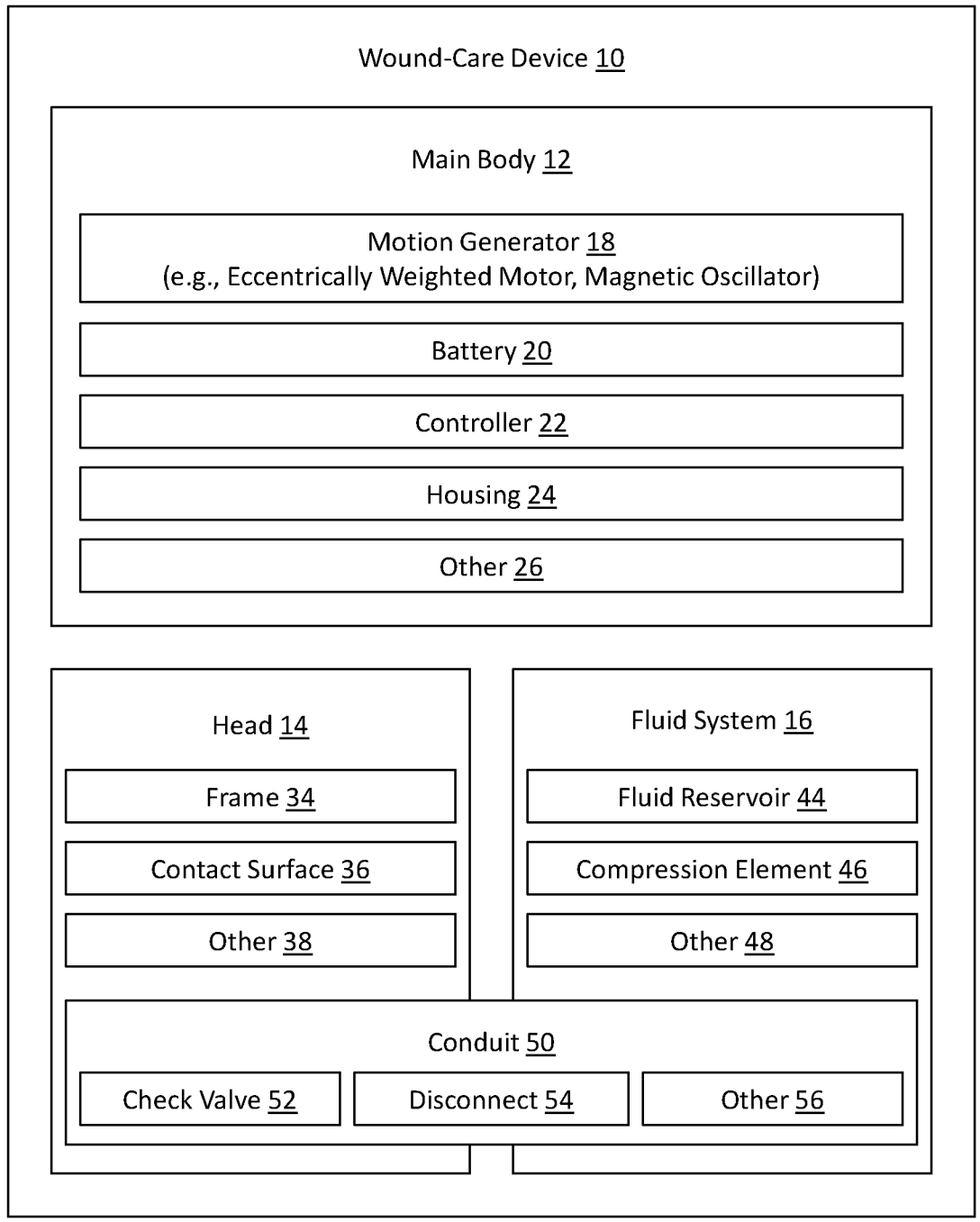
FIG. 4 is a schematic block diagram of one embodiment of a wound-care device in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIGS. 1-4, devitalized tissue appearing in a wound bed may include fibroslough (primarily fibrinous tissue), leukoslough (primarily WBC accumulation), necroslough (primarily necrotic tissue), and bioslough (primarily biofilm). Slough may be defined as devitalized tissue comprising primarily fibrin, but it may also include white blood cells, debris, and the like. The presence of slough may interrupt granulation and delay healing. It may also provide a favorable environment in which bacteria may grow and spread. There is also an infection continuum in wounds, proceeding from contaminated wound bed (bacteria on surface of wound but not replicating), colonized (bacteria are living on wound bed and replicating), early biofilm formation, mature biofilm formation, and local to systemic infection with biofilm seeding. Accordingly, to promote healing, a wound-care device 10 in accordance with the present invention may facilitate the removal of devitalized tissue from a wound. This removal may be described as wound cleansing, desloughing, and/or debridement.

Depending on various factors, devitalized tissue in a wound bed may have different consistencies. For example, the consistency of devitalized tissue may be described as (1) mucinous (i.e., slimy and soft), (2) gelatinous. (3) stringy and/or clumpy, (4) fibrinous, and/or (5) leathery. Depending on the consistency of the devitalized tissue, different debridement tools and/or methods may be needed. For example, debridement suitable for devitalized tissue that is "leathery" may be too aggressive for devitalized tissue that is "mucinous." Accordingly, a wound-care device 10 may be adjustable or adaptable to provide proper cleansing and/or debridement across the range of consistency of devitalized tissue.

Bacterial biofilms can be found in 60-90% of chronic wounds and in approximately 6% of acute wounds. Biofilms usually contain multiple bacterial species. Biofilms can be found in multiple places, including within a wound bed (i.e., to a depth of about 60-70 microns below the surface of a wound), on a wound surface, in slough, in fluids on and around a wound bed, etc. and can migrate onto the wound dressings as well. Accordingly, a wound-care device 10 may be used to disrupt bacteria growth, prevent the formation of bacterial biofilms, and/or treat bacterial biofilms.

Wound care is complicated by the fact that a wide variety of people with a wide variety of medical experience and/or training are tasked with providing such care. For example, at home, patients with little to no medical experience or training are often tasked with providing their own wound care (e.g., tasked with fitting and/or changing their own would dressings). For patients with more serious wounds, wound care may be provided at their respective homes by ancillary healthcare staff having various levels of wound-care training. Some ancillary healthcare staff may have associate nursing degrees. Others have bachelor degrees in nursing. Still others may be specialized wound, ostomy, and continence nurses (WOCN). However, regardless of such educational background, ancillary healthcare staff will have different comfort levels and skill sets with respect to cleansing wounds and conducting even basic wound cleansing and/or debridement.

In institutional, long-term care settings such as nursing homes and long-term acute care (LTAC) hospitals, there may be wound-care teams with more advanced training and an enhanced skill set due to their repeated and regular treating of complicated wounds. In the offices of physicians and surgeons, wounds often need cleansing or mild surgical debridement. Such treatment is often performed in an operating room. However, such use of an operating room is often unnecessary and increases the cost of treatment and may increase morbidity depending on choice of anesthesia.

Accordingly, to address the wide variety of people tasked with providing wound care, a wound-care device 10 in accordance with the present invention may be easy to use. Moreover, it may be configured so as to limit the potential for misuse or harmful use. Accordingly, both an inexperienced patient and a highly trained medical professional may both use a wound-care device 10 to beneficial effect.

In selected embodiments, a wound-care device 10 may comprise a main body 12 or handle portion 12 and a head 14. In other embodiments, a wound-care device 10 may comprise a main body 12, a head 14, and a fluid system 16. A head 14 may removably connect to a main body 12. In operation, a head 14 may apply motion (e.g., vibration, oscillation, reciprocation, or the like) generated by a main body 12 to a wound surface. Accordingly, a main body 12 may be responsible for generating a desired motion and a head 14 may be responsible to conduct that motion from the main body 12 to a wound surface.

In certain embodiments, a main body 12 may include a motion generator 18, one or more batteries 20, a controller 22, a housing 24, one or more other components 26 or structures 26, or the like or a combination or sub-combination thereof. A motion generator 18 may generate vibration, oscillation, reciprocation, or the like at a desired frequency. One or more other structures 26 (e.g., a physical linkage, shaft, or the like), a housing 24, or the like may conduct the vibration, oscillation, or reciprocation to a head 14.

In selected embodiments, a motion generator 18 may vibrate, oscillate, reciprocate, or the like at a relatively low sonic frequency in a range from about 100 Hz to about 1000

Hz. Alternatively, or in addition thereto, a motion generator 18 may vibrate, oscillate, reciprocate, or the like at a relatively high amplitude (e.g., an amplitude in the range from about 1 mm to about 10 mm and, more preferably, about 3 mm to about 8 mm). That is, once a head 14 is applied to a main body 12, the vibration, oscillation, reciprocation, or the like of a motion generator 18 may produce a side-to-side sweeping motion at a distal end of the head 14 that is about 1 mm to about 10 mm (and, more preferably, about 3 mm to about 8 mm) from one extreme to the other. In other embodiments, the amplitude and/or motion may be different, but may still be in a relatively low sonic frequency range. Thus, a device 10 in accordance with the present invention operate at a frequency that is much lower than any ultrasonic debridement device and benefit from the higher amplitude that may be obtained at that lower frequency.

In selected embodiments, a motion generator 18 may comprise an electromagnet with a polarity that is alternated at a desired frequency in order to create a desired vibration, oscillation, or reciprocation (e.g., a desired vibration, oscillation, or reciprocation in a linkage that extends to engage a head 14). In other embodiments, a motion generator 18 may comprise an electric motor turning a shaft having an eccentric weight secured thereto to generate a vibration, oscillation, or reciprocation effect.

For example, a motion generator 18 may comprise an electric motor having a rated speed of about 9,000 to about 36,000 revolutions per minute (and preferably about 18,000 to about 22,000 revolutions per minute) when a rated load (e.g., an eccentric mass of about 0.5 to about 1.0 grams and preferably about 0.75 grams) is applied to the shaft thereof. That speed may translate to a vibration, oscillation, reciprocation, or the like in the sonic range of about 150 Hz to about 600 Hz, where each cycle may comprise two strokes (e.g., one stroke or deflection to the left and a return stroke or deflection to the right) across a wound bed. Thus, a motion generator 18 operating at about 150 Hz may produce about 300 vibration strokes per second, while a motion generator 18 operating at about 600 Hz may produce about 1,200 vibration strokes per second.

A motion generator 18 may generate vibration, oscillation, and/or reciprocation in a linkage 28 or other structure 28 that extends to engage a head 14. For example, in selected embodiments, one end of a main portion 12 may comprise or form a horn 28 within which a motion generator 18 may be positioned. When turned "on," a motion generator 18 may cause a horn 28 to vibrate, oscillate, and/or reciprocate at a desired frequency. Accordingly, when a horn is inserted within or otherwise connected to a correspondingly shaped head 14, the horn 28 may communicate that vibration, oscillation, and/or reciprocation to the head 14.

In selected embodiments, the structure configuration of a horn 28, a head 14, or a horn 28 and head 14 combination may define the type or shape of motion generated by a motion generator 18. For example, by selecting where the greatest mass is located, which axis of bending or deflection is preferred (i.e., is less resistant to bending or deflection), or the like or a combination thereof, the motion of a head 14 may be defined as being more circular, rocking back and forth, translating side to side, or the like in order to provide a desired effect, action, or operation on a wound bed.

A battery 20 may provide the electrical power required by a motion generator 18. In selected embodiments, a battery 20 may be rechargeable. For example, a battery 20 (e.g., a lithium ion battery) may include or be connected to a receiving or secondary coil to enable or support wireless charging when a corresponding device 10 is placed on or in a charging station. Alternatively, or in addition thereto, a device may be at least partially powered and/or charged by one or more supercapacitors.

A controller 22 may control operation of a main body 12. In selected embodiments, a controller 22 may comprise a switch 30 for turning a motion generator 18 on and off. Alternatively, or in addition thereto, a controller 22 may comprise a printed circuit board (PCB) 32, one or more integrated circuits, one or more processors (e.g., an application-specific integrated circuit (ASIC), a programmable logic controller (PLC), or the like), memory, or the like or a combination or sub-combination thereof in order to control a motion generator 18. Accordingly, a controller 22 may automatically control certain functions of a wound-care device 10.

For example, a controller 22 may turn off a motion generator 18 if a battery is low on charge, if a particular time interval (e.g., 2 to 3 minutes) has passed since the device 10 was turned on, or the like. A controller 22 may control the speed and/or power of a device 10 through one or more switches 30, buttons 30, or the like that may be operated by a user. In selected embodiments, a controller 22 may regulate or condition a voltage (e.g. increase a voltage from 3.0 V to 3.7 V or some other desired voltage) of electrical current passing from a battery 20 or other power source to a motion generator 18 as desired or necessary.

In selected embodiments, a controller 22, may pulse, momentarily pause vibration, beep, flash a light, or the like at predetermined, regular intervals (e.g., every 30 seconds) so that the user may more easily monitor and control the time spent cleansing or debriding a wound. Accordingly, a physician may instruct a patient or home-healthcare nurse to use a device 10 for 30 seconds to cleanse a small wound, 90 seconds for a large wound, or the like. The patient or nurse may then watch for the appropriate number of pulses or beeps in order to meet the prescribed treatment time.

A housing 24 may contain various other components of a main body 12. For example, a housing 24 may contain and provide structure for mounting or anchoring a motion generator 18, battery 20, controller 22, and the like. In selected embodiments, a housing 24 may form a handle. Accordingly, when a user uses a wound-care device 10, the user may grasp and hold the housing 24.

In certain embodiments, a head 14 may include a frame 34, a contact surface 36, one or more other components 38 or structures 38, or the like or a combination or sub-combination thereof. A frame 34 may extend from a main body 12 to support a contact surface 36. For example, a frame 34 may engage a physical linkage 28, horn 28, or the like that is selectively vibrated, oscillated, and/or reciprocated by a motion generator 18. Accordingly, a frame 34 may conduct vibrations, oscillations, and/or reciprocations that originate with a motion generator 18 to a contact surface 36.

A contact surface 36 may be configured to contact a wound surface. In selected embodiments, a head 14 may be considered as having a front side 40 and a back side 42. In such embodiments, a contact surface 36 may be or correspond to a front side 40 of a head 14. Accordingly, a contact surface 36 may be configured to provide a desired cleansing, desloughing, debridement, or the like.

In certain embodiments, a contact surface 36 may be selectively separable from a corresponding frame 34. Accordingly, a user may obtain or control a cleansing, desloughing, or debriding effect by selecting and installing a contact surface 36 designed to provide the cleansing, desloughing, or debriding effect. Alternatively, a contact surface 36 may be integrally or substantially permanently connected to a frame 34. Accordingly, in certain embodiments, a user may obtain or control a cleansing, desloughing, or debriding effect by selecting and installing a head 14 having a contact surface 36 designed to provide the cleansing, desloughing, or debriding effect.

In selected embodiments, a contact surface 36 may be configured for single use. For example, a contact surface 36 (or a head 14 comprising a frame 34 and a contact surface 36) may be provided to a user in a sterile condition and within sterile packaging. After being used on a wound, a contact surface 36 will no longer be sterile and may have significant bacterial contamination. Accordingly, the contact surface 36 (or the head 14 comprising the frame 34 and the contact surface 36) may be discarded and a new contact surface 36 (or a new head 14) may be used for the next cleansing, desloughing, or debridement.

A fluid system 16 may facilitate wound cleansing, desloughing, and/or debridement. Fluid provided or delivered by a fluid system 16 may tend to flush loose material and particles out of a wound bed. For example, fluid delivered to a central location on a contact surface 36 may irrigate outward (e.g., radially outward) and across the contact surface 36 (e.g., within various channels formed in the contact surface 36) to aid in removing, dislodging, and flushing bacteria, toxins, and cellular debris and preventing clogging of the contact surface 36. Alternatively, or in addition thereto, fluid may tend to soften materials that are being removed so as to aid in (e.g., speed) their removal.

In selected embodiments, a fluid system 16 may include a fluid reservoir 44, a compression element 46, one or more other components 48 or structures 48, or the like or a combination or sub-combination thereof. A fluid reservoir 44 may contain a fluid (e.g., saline, an antibiotic or antiseptic in liquid form, a gel, a paste, or the like). A fluid reservoir 44 may be deformable. Deformation of a fluid reservoir 44 may tend to expel fluid therefrom. Accordingly, manual deformation (e.g., squeezing, flattening, etc.) of a fluid reservoir 44 may provide the motive force for and/or control a rate of expelling fluid from a fluid reservoir 44.

In certain embodiments, a fluid reservoir 44 may be directly manually compressed by the hand or fingers of a user. In other embodiments, a compression element 46 may be included to assist in compressing a fluid reservoir 44. A compression element 46 may be a structure or combination of structures that facilitates deformation (e.g., compression) of a fluid reservoir 44. For example, a compression element 46 may be a structure that holds a fluid reservoir 44 in place along a housing 24 (e.g., along an underside of a housing 24) so that a user can hold the device 10 and squeeze the fluid reservoir 44 at the same time (e.g., with the same hand). Alternatively, or in addition thereto, a compression element 46 may comprise a lever that operates in conjunction with a housing 24 so that a fluid reservoir 44 may be squeezed therebetween. Accordingly, by pulling the lever, the same hand with which a user holds a main body 12 may be used to expel fluid from the fluid reservoir 44.

In selected embodiments, a wound-care device 10 may include a conduit 50. A conduit 50 may extend to place a fluid reservoir 44 in fluid communication with a head 14. Accordingly, manual deformation of a fluid reservoir 44 may urge fluid out of the fluid reservoir 44 and into a conduit 50. The fluid may then travel through the conduit 50 until it reaches the head 14 where it may be expelled proximate a contact surface 36. In other embodiments, a fluid conduit 50 (or selected portions of a fluid conduit 50) may be integral to a head 14.

A conduit 50 may include a check valve 52, a disconnect 54, one or more other components 56 or structures 56, or the like or a combination or sub-combination thereof. A check valve 52 may permit fluid to move from a fluid reservoir 44 toward a head 14 and prevent fluid from moving from the head 14 back toward a fluid reservoir 44. This may prevent contaminated fluid from being sucked into a wound-care device 10. In certain embodiments, a check valve 52 may be part of a fluid reservoir 44 rather than part of a conduit 50. In other embodiments, a check valve 52 may be part of a head 14 rather than part of a conduit 50. However, wherever a check valve 52 may be located, it may enforce the same one way flow of fluid.

One or more disconnects 54 may enable a conduit 50 to be selectively connected and/or disconnected to a fluid reservoir 44, a head 14, or the like. Alternatively, a conduit 50 may simply have one or more ends that may be inserted within or over a properly sized aperture or port of a head 14 or fluid reservoir 44 in order to enable fluid to flow across the resulting interface. In either case, a conduit 50 may selectively connect to and disconnect from a head 14, a fluid reservoir 44, or both a head 14 and fluid reservoir 44. Accordingly, heads 14, fluid reservoirs 44, and conduits 50 may be installed, removed, and/or discarded as needed.

In selected embodiments, a fluid system 16 and conduit 50 may be omitted from a wound-care device 10. In such embodiments, cleansing, desloughing, and/or debridement of a wound bed may be conducted in a "dry" manner without the addition of any fluid. Alternatively, fluid may be applied in a separate process. For example, a liquid, gel, paste, or the like may be applied to a wound bed in a first process that precedes and is separate from using a wound-care device 10 in accordance with the present invention to clean, deslough, or debride the wound bed.

Figure 5:
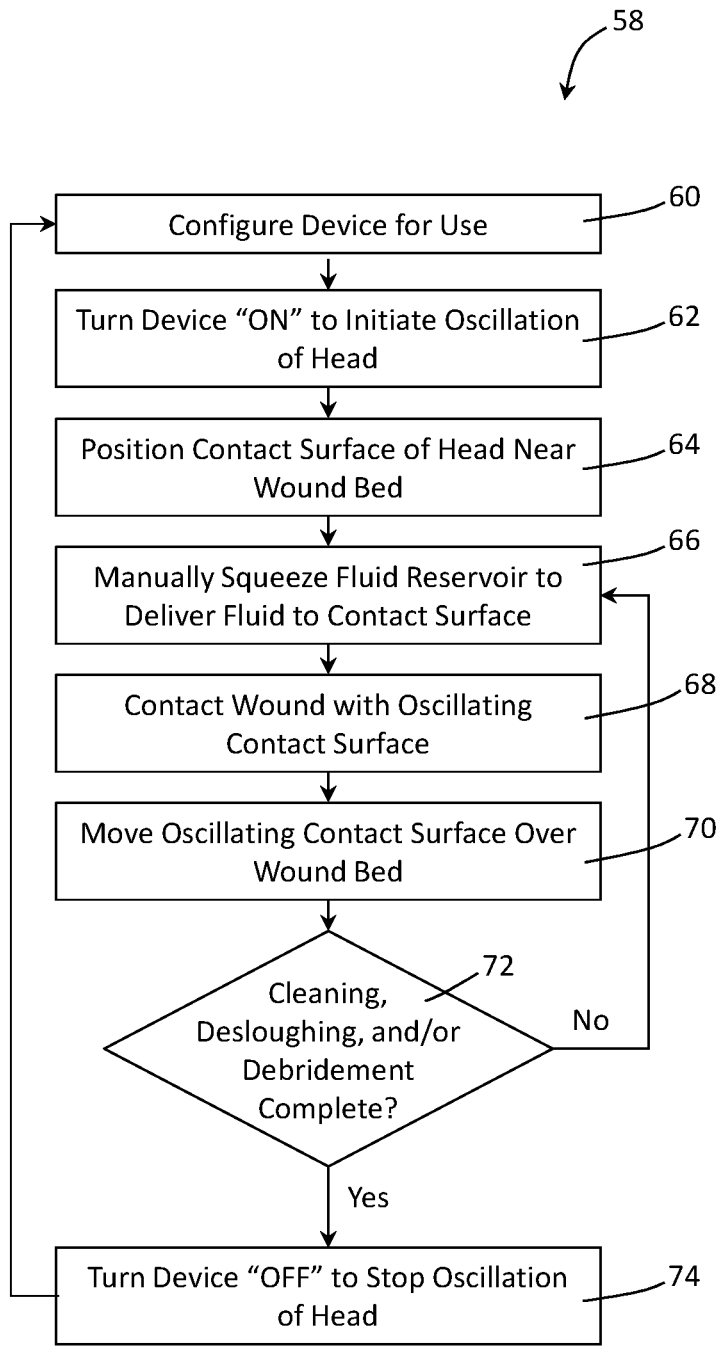
FIG. 5 is a block diagram of one embodiment of a method for using a wound-care device in accordance with the present invention.

Referring to FIG. 5, in selected embodiments, a method 58 for cleansing, desloughing, and/or debriding a wound bed may begin when a device 10 is configured 60 for use. Configuring 60 a device 10 for use may include selecting and installing an appropriate contact surface 36 or head 14, selecting and installing a fluid reservoir 44 and/or conduit 50, or the like or a combination thereof. Thereafter, a device 10 may be turned 62 "on" (e.g., to start oscillation or other motion of a head 14) and then a contact surface 36 may be positioned 64 proximate a wound bed.

To initiate cleansing, desloughing, and/or debriding, a user may manually squeeze 66 a fluid reservoir 44 to create a flow of fluid to the contact surface 36 and/or place 68 a contact surface 36 in contact with the wound bed. Thereafter, the user may move 70 the contact surface 36 over the wound bed. Oscillation or other motion of the contact surface 36 alone or in combination with a rinsing effect produced by the fluid may tend to clean, deslough, and/or debride the wound bed. Accordingly, a user may continued to dispense 66 fluid, apply 68 the contact surface 36 to the wound bed, and move 70 the contact surface 36 over the wound bed until it is determined 72 that the cleansing, desloughing, and/or debriding is complete. Once it is complete, the device 10 may be turned 74 "off."

Figure 6:
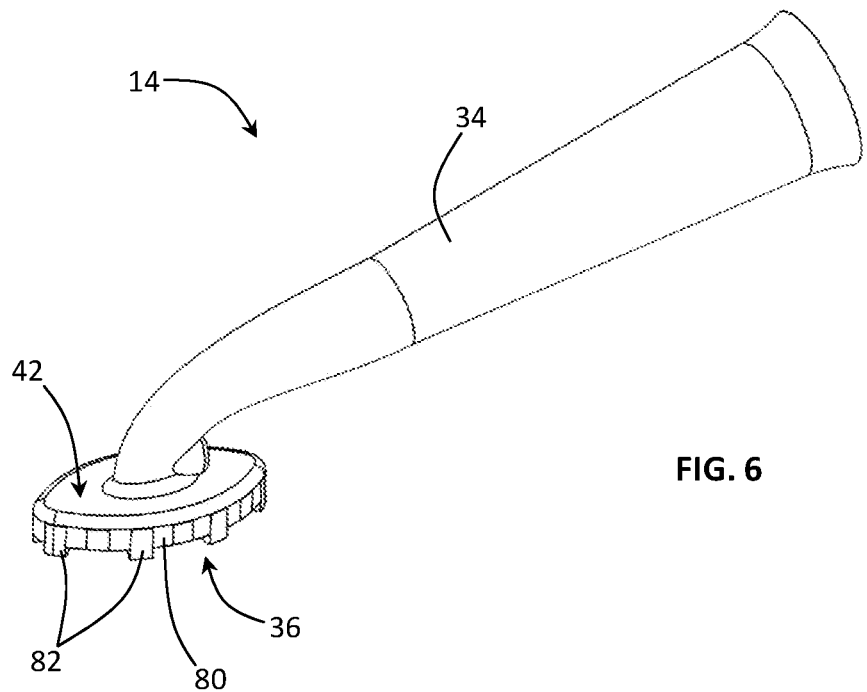
FIG. 6 is a perspective view of a removable head of the wound-care device of FIG. 1.
Figure 7:
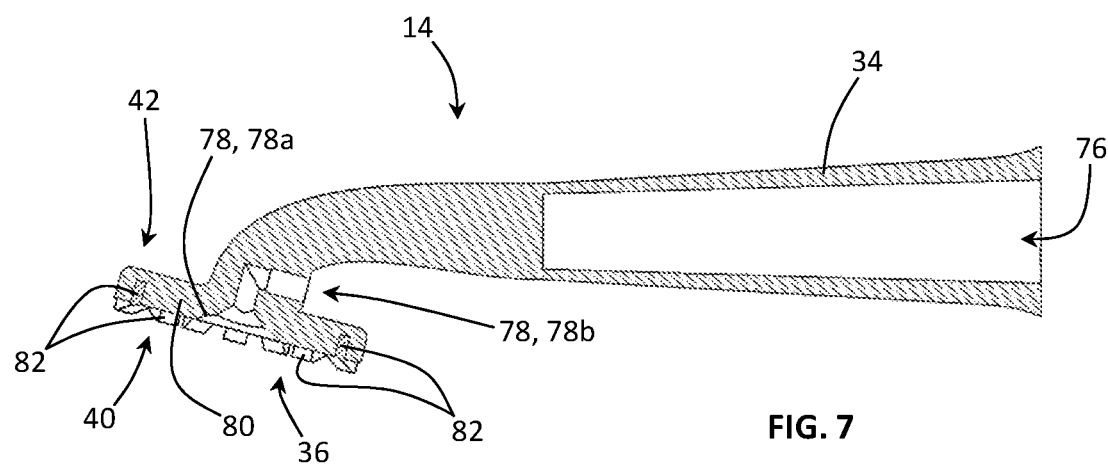
FIG. 7 is a side cross-sectional view of the removable head of FIG. 6.

Referring to FIGS. 6 and 7, in selected embodiments, a frame 34 of a head 14 may have an aperture 76 to support securement to a main body 12. In certain embodiments, such an aperture 76 may be shaped and sized to selectively receive (e.g., frictionally engage via mating tapers) a physical linkage 28, horn 28, or the like that conducts vibration, oscillation, and/or reciprocation from a main body 12 to a head 14.

In certain embodiments, an aperture 78 may be formed in a head 14 to enable fluid to pass therethrough. For example, a head 14 may include an aperture 78 extending from a back side 42 to a front side 40 of the head 14. A front portion 78*a* of an aperture 78 may be positioned centrally with respect to a contact surface 36. Accordingly, when fluid is expelled through that front portion 78*a* of the aperture 78, the fluid may flow, migrate, or otherwise move radially outward with respect to the contact surface 36. This radial flow or movement may tend to clean or flush the contact surface 36. A back portion 78*b* of an aperture 78 may be sized and shaped to receive and secure (e.g., frictionally secure) one end of a conduit 50 therewithin, thereby placing the aperture 78 in fluid communication with a fluid reservoir 44. In embodiments where a device 10 does not include a fluid system 16 and conduit 50, an aperture 78 in a head 14 may be omitted.

Contact surfaces 36 in accordance with the present invention may have any suitable configuration. Suitable configurations may vary in shape (e.g., rectangular, circular, diamond, oval, or the like), size (e.g., have a length and width in a range from about 5 mm to about 30 mm and preferably a length of about 28 mm and a width of about 14 mm), surface area (e.g., have a footprint of about 200 square millimeters to about 400 square millimeters and preferably a footprint of about 300 square millimeters), surface contour (e.g., flat, convex, or the like), surface texture or profile (e.g., sharp, rounded, course, fine, or the like), channeling (e.g., no channels, radial channels, orthogonally intersecting channels, circumferential channels, or the like or combinations or sub-combinations thereof, composition (e.g., solid polymer, solid elastic polymer, silicone, open cell foam, closed cell foam, or the like), hardness, or the like or in various combinations or sub-combinations thereof. Accordingly, the configuration may be selected to provide a desired performance.

In selected embodiments, contact surfaces 36 may be formed of silicone elastomer or some other polymer in various hardnesses (e.g., having a Shore A hardness in the range from about 15 to about 100, Shore D hardness in the range from about 40 to about 90, or Rockwell R hardness in the range from about 50 to about 100). In certain embodiments, a contact surface 36 may comprise a base 80 and one or more extensions 82 extending from the base 80. The base 80 and the one or more extensions 82 may be formed of different materials to support different functions. For example, a base 80 may be formed of a material that is easily formable and relatively rigid (e.g., polymer), while one or more extensions 82 may be formed of a material that is compatible with the function of cleansing, desloughing, and/or debriding a wound (e.g., an elastomer having a desired Shore A hardness). In selected embodiments, one or more extensions 82 may be insert molded or otherwise embedded within a base 80 to enable the extensions 82 to securely extend away from the base 80 and define a texture or profile for the contact surface 36.

In selected embodiments, varying the number and sharpness of the edges of one or more extensions 82, the pointedness of one or more extensions 82, the height of one or more extensions 82, the lateral offset of one extension 82 with respect to one or more adjacent extensions 82, the hardness of the material (e.g., polymer, elastomer, or the like) forming the one or more extensions 82, and/or the pressure applied by the user (e.g., the force with which the user urges the contact surface 36 against a wound bed) may be used to control the aggressiveness of the cleansing, desloughing, and/or debrided. Accordingly, extensions 82 providing a high concentration of sharp edges formed of a relatively hard material may produce a very aggressive contact surface 36, while extensions 82 having an absence (or lesser quantity) of sharp edges (e.g., rounded edges) and/or being formed of a relatively soft material may provide a very gentle contact surface 36. Fluid dispensed from one or more apertures 78 may flow over and in between extensions 82 and flush the contact surface 36 of debris during use of a device 10. This flushing action may better cleanse a wound bed and facilitate dislodgement and removal of bacteria, biofilm, and devitalized tissues during cleansing, desloughing, and/or debridement.

In certain embodiments, different extensions 82 of a particular contact surface 36 may have different edges and/or hardnesses associated therewith. For example, the extensions 82 associated with the ends (e.g., distal and proximal ends) of a contact surface 36 may be formed of a harder material than the more centrally located extensions 82. Alternatively, or in addition thereto, the extensions 82 associated with the ends (e.g., distal and proximal ends) of the contact surface 36 may have sharper edges than the more centrally located extensions 82. Accordingly, a user may apply different portions of a contact surface 36 to a wound bed to provide a different effect.

Figure 8:
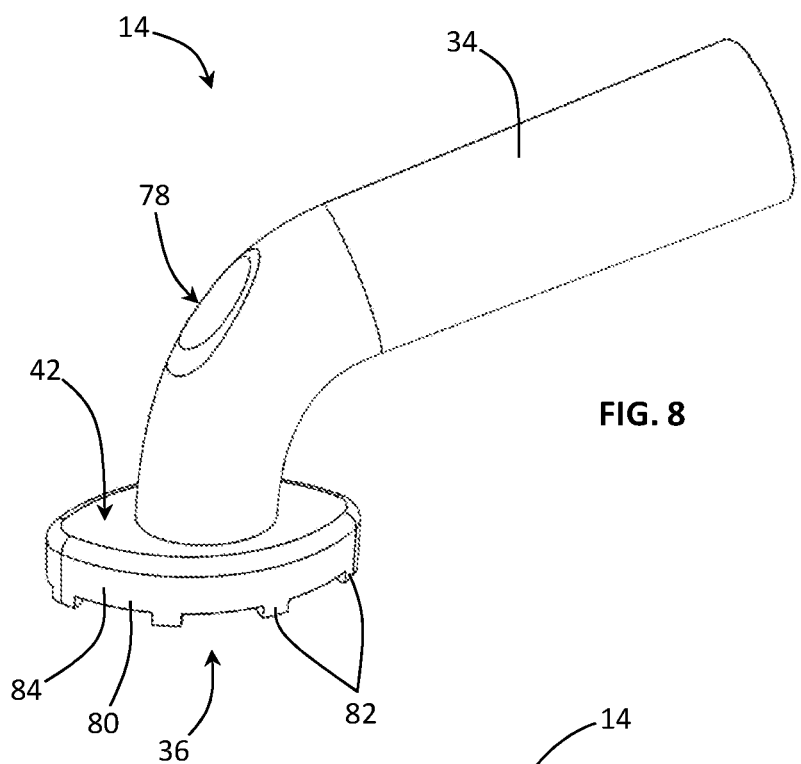
FIG. 8 is a perspective view of an alternative embodiment of a removable head for a wound-care device in accordance with the present invention.
Figure 9:
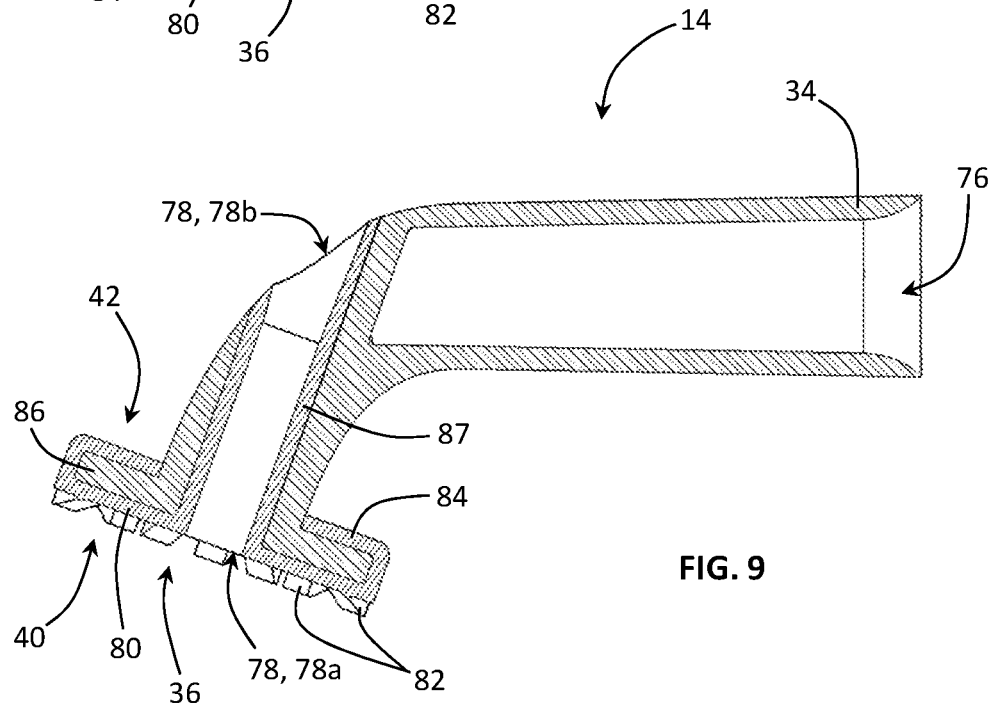
FIG. 9 is a side cross-sectional view of the removable head of FIG. 8.
Figure 10:
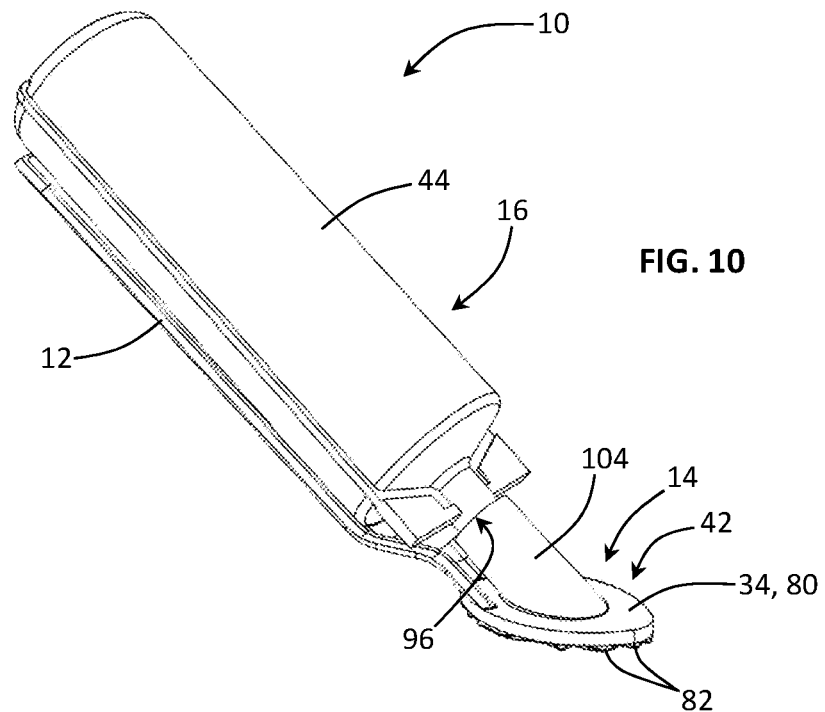
FIG. 10 is a perspective view of an alternative embodiment of a wound-care device in accordance with the present invention.
Figure 11:
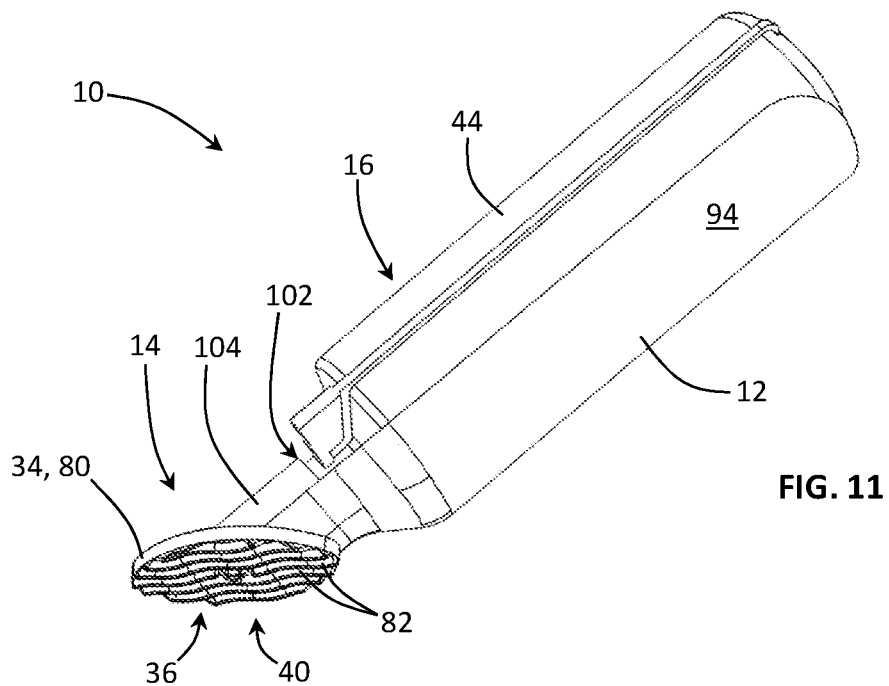
FIG. 11 is another perspective view of the wound-care device of FIG. 10.
Figure 12:
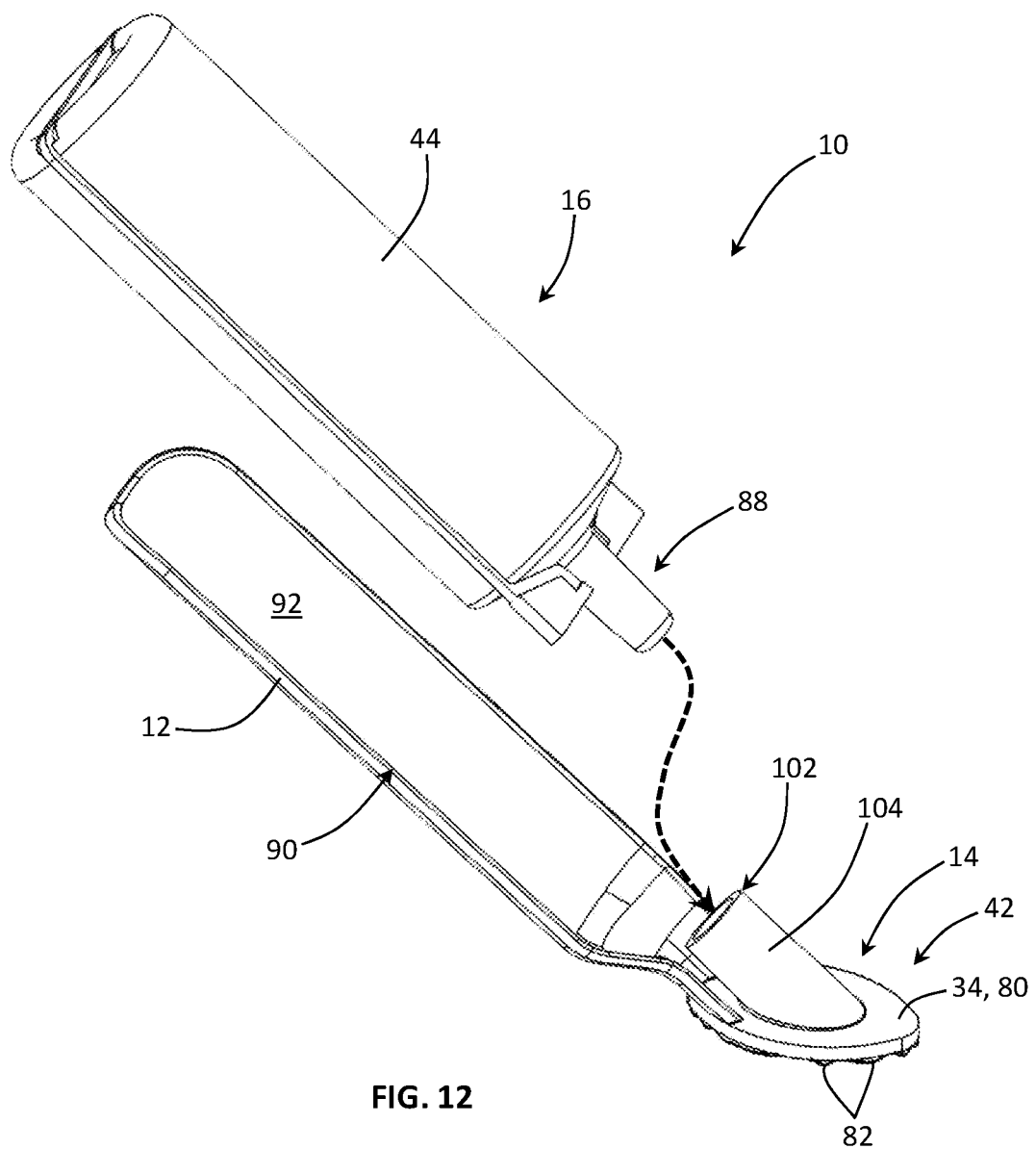
FIG. 12 is an exploded perspective view of the wound-care device of FIG. 10.
Figure 13:
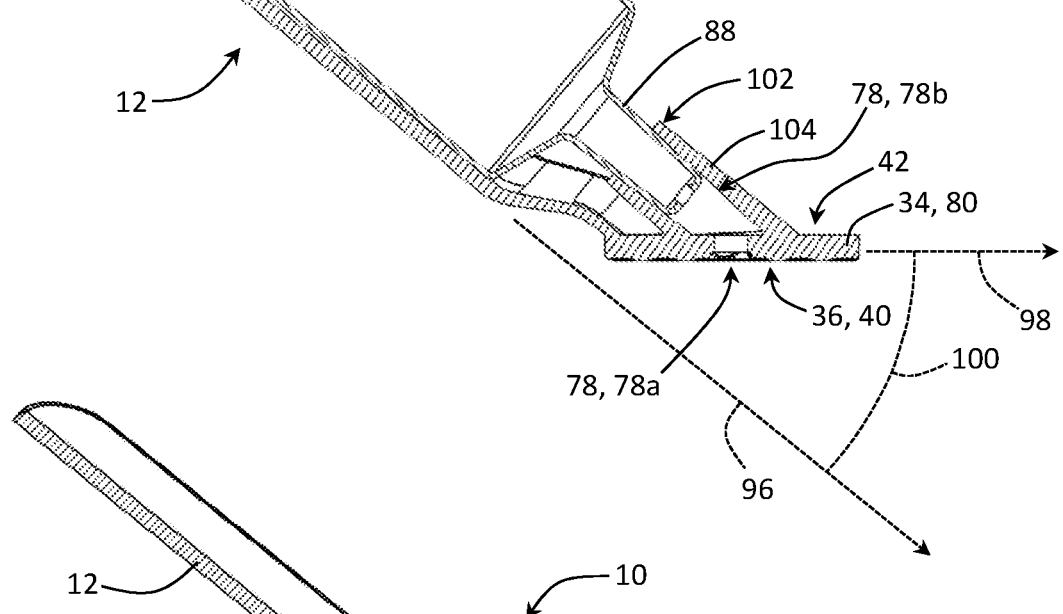
FIG. 13 is a side cross-sectional view of the wound-care device of FIG. 10.

Referring to FIGS. 8 and 9, in selected embodiments, a contact surface 36 may be formed as a boot 84 (e.g., a boot formed of an elastomer) that slips over a supporting structure 86 formed as part of a frame 34. In such embodiments, a boot 84 may form (e.g., monolithically form) both one or more extensions 82 and a base 80 from which the one or more extension 82 project. Such an embodiment may allows selected portions of a head 14 to be reusable, and the boot 84 to include the contact surface 36 and be a single use item formed of a very inexpensive elastomeric material, to reduce cost of use of the device. This may also simplify manufacturing, facilitate interchangeability, or the like. Alternatively, a boot 84 may be applied to a frame 34 in a two-step, over-molding process. In such embodiments, the resulting head 14 may be a single use item in its entirety.

In certain embodiments, a removable contact surface 36 (e.g., a base 80 portion of a contact surface 36) may include a length of tubing 87 extending away from a back thereof. A conduit 50 of a fluid system 16 may connect to such tubing to deliver fluid to the contact surface 36. Accordingly, in such embodiments, fluid may never contact a frame 34. The length of the tubing 87 may be selected to reduce the likelihood of biological contamination of the conduit 50. In selected embodiments, the length of the tubing 87 may be about 1 cm to about 13 cm. As a result, a contact surface 36 and associated tubing 87 may be discarded after use, while a conduit 50 may be used multiple times.

Referring to FIGS. 10-13, in selected embodiments, a wound-care device 10 may be configured for maximum utility and minimum cost. Accordingly, in certain embodiments, a wound-care device 10 in accordance with the present invention may be non-electric (e.g., a motion generator and 18 and corresponding or related structures 20, 22, 24, 28 may be omitted from a device 10). Alternatively, or in addition thereto, a wound-care device 10 may be single use. For example, in selected embodiments, a wound-care device 10 may comprise a main body 12 or handle portion 12 that is monolithically formed together with a head 14 (e.g., the main body 12 and head 14 may be injection molded as a single unit). The material forming the main body 12 and head 14, including the contact surface 36 of the head 14, may be homogeneous throughout. This may reduce the cost of manufacturing a device 10 in accordance with the present invention, make a device 10 viable as a single use device 10, and avoid all sanitation and sterilization issues associated with reuse of any part of a device 10.

In certain embodiments, the material used to form the main body 12 and head 14 of a device 10 may be or reflect a compromise between the structural requirements for the main body 12 and head 14 and the structural requirements for a contact surface 36 of the head 14. In selected embodiments, the material may be or comprise a polymer having a Rockwell R hardness of about 100 or lower. For example, the material may be or comprise polypropylene (e.g., polypropylene random copolymer with a Rockwell R hardness of about 90 and a flexural modulus of about 966 MPa). Accordingly, in certain embodiments, a wound-care device 10 may comprise a main body 12, head 14, and contact surface 36 that are monolithically formed (e.g., injection molded as a single unit) in a polymeric material such as polypropylene.

A fluid system 16 paired with a simplified main body 12 and head 14 combination may be similarly simplified. For example, a conduit 50 may be omitted and a fluid system 16 may comprise a fluid reservoir 44 (e.g., a fluid reservoir 44 in the form of a squeeze bottle, single use container, saline bullet, or the like) having an outlet 88 that directly engages (e.g., is inserted into a mating back portion 78*b* of) an aperture 78 of a head 14. In certain embodiments, a fluid reservoir 44 may be a sterile, single-use, 15 ml saline bullet.

In selected embodiments, a main body 12 or handle portion 12 of a device 10 may have a concavity 90 formed therein. A concavity 90 may be sized and shaped to support a fluid reservoir 44 at least partially therewithin. For example, a fluid reservoir 44 (e.g., a squeeze bottle, saline bullet, or the like) may have a cylindrical side wall. Accordingly, a concavity 90 of a main body 12 may have an interior surface 92 that follows, tracks, or otherwise cradles at least a portion of a cylindrical side wall of a fluid reservoir 44. Such cradling, alone or in combination with insertion of an outlet 88 of a fluid reservoir 44 into an aperture 78 of a head 14, may secure a fluid reservoir 44 in place or make it easier for a user to hold a fluid reservoir 44 in place during use (e.g., during movement of a device 10 with respect to a wound bed and/or squeezing of a fluid reservoir 44 to expel fluid).

In certain embodiments, an exterior surface 94 of a main body 12 may track or follow an interior surface 92. Alternatively, or in addition thereto, the spacing between the interior surface 92 and the exterior surface 94 may be relatively small. Accordingly, a thickness of a material forming a main body 12 (e.g., a thickness of a material located between the interior surface 92 and the exterior surface 94) may be relatively thin and/or substantially uniform. This may reduce the amount of material needed to produce of device 10. Additionally, in selected embodiments, a curvature of a main body 12 that produces a concavity 90 may effectively define or form at least one corrugation running lengthwise from one end of a main body 12 to the other. Such a corrugation may stiffen a main body 12 against bending without requiring large or larger amounts of material.

In selected embodiments, a main body 12 may extend in a first direction 96 (e.g., may have a line or axis of symmetry that extends in a first direction 96). A head 14 may extend away from a main body 12 in a second direction 98 that is different from the first direction 96 (e.g., may have a line or axis of symmetry that extends in a second direction 98 that is different from the first direction 96). For example, in certain embodiments, a head 14 may extend away from a main body 12 in a second direction 98 that departs from the first direction 96 at an angle 100 in a range from about 25 to about 55 degrees and preferably at an angle 100 in a range from about 40 to about 50 degrees. In selected embodiments, a head 14 may extend away from a main body 12 in a second direction 98 that departs from the first direction 96 at an angle 100 of about 45 degrees.

In selected embodiments and/or uses, a fluid reservoir 44 may be omitted from a device 10 comprising a simplified main body 12 and head 14 combination. In such embodiments, cleansing, desloughing, and/or debridement of a wound bed may be conducted in a "dry" manner without the addition of any fluid. Alternatively, fluid may be applied in a separate process. For example, a liquid, gel, paste, or the like may be applied to a wound bed in a first process that precedes and is separate from using a wound-care device 10 in accordance with the present invention to clean, deslough, or debride the wound bed.

When a fluid reservoir 44 is omitted, a concavity 90 formed in a main body 12 may provide a location for a finger (e.g., an index finger) of a user to extend and rest during use of the corresponding device 10. That is, rather than cradling a fluid reservoir 44 (e.g., a saline bullet having a diameter that is about equal to or slightly larger than a typical finger diameter), a concavity 90 may cradle a finger (e.g., an index finger) of a user. When using a device 10 in such a manner, a user may place the tip of whichever finger is cradled within a concavity 90 against a proximal end 102 of a structure 104 or conduit 104 forming a back portion 78*b* of an aperture 78 extending through the head 14. This engagement or abutment with the tip of the finger may enable a user to apply a desired or sufficient amount of pressure to a head 14 as it contacts a wound bed and/or better sense or control how much pressure is applied through a head 14 to a wound bed.

In certain embodiments, a finger positioned within a device 10 may enable a user to selectively apply specific regions of a head 14 or contact surface 36 (e.g., a distal end of a head 14, either side of a head 14, a proximal end of a head 14) to a wound bed with greater user control of the force applied and the angle of the contact surface 36 relative to a wound bed. This may give a user superior control over a pressure and location of engagement between a head 14 and a wound bed and better results or performance for the medical procedure.

In selected embodiments, a simplified main body 12 and head 14 combination may be distributed in an individually wrapped, sterile condition. In certain embodiments, multiple individually wrapped devices 10 may be combined into packs of a selected quantity (e.g., a pack of about five or some other quantity corresponding to about a two week supply). Accordingly, when tending to a patient, a medical professional may select a pack of devices 10, open and use one device 10 to clean, deslough, or debride a wound bed of a patient and/or teach the patient how to do it, and then send the remaining unopened devices 10 in the pack home with the patient for the patient use in the interim before the next visit with a medical professional. In certain embodiments, such a pack may include or be provided to a patient with a selected number of fluid reservoirs 44 containing fluid (e.g., a selected number of saline bullets of a size that fits the simplified main body 12 and head 14 combination).

Figure 14:
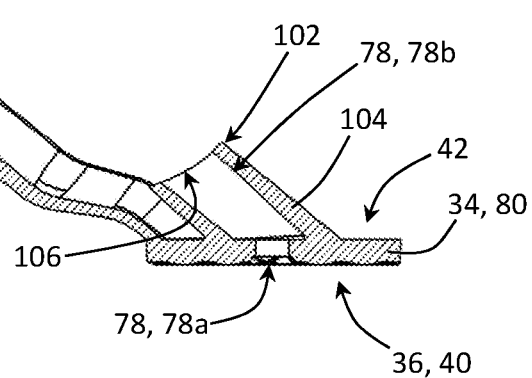
FIG. 14 is a side cross-sectional view of another alternative embodiment of a wound-care device in accordance with the present invention.

Referring to FIG. 14, in selected embodiments, a proximal end 102 of a structure 104 or conduit 104 forming a back portion 78*b* of an aperture 78 extending through the head 14 may be shaped so as to comfortably engage a finger tip of a user. For example, a proximal end 102 may have a curvature 106 formed therein that follows or replicates a portion of the curvature of a finger tip. Accordingly, a structure 104 or conduit 104 may be configured to alternatively and with equal effectiveness engage an outlet 88 of a fluid reservoir 44 and a tip of a finger of a user.

In certain embodiments, a structure 104 or conduit 104 may be sized and shaped to engage a conduit 50 with a Luer-taper type connection. For example, an interior surface of an aperture 78 may be sized and shaped to receive and frictionally engage a Luer-type, male, slip-fit connector. Alternatively, or in addition thereto, an exterior surface of a structure 104 or conduit 104 may be sized and shaped to receive and frictionally engage a Luer-type, female, slip-fit connector. Such an arrangement may enable standard conduits 50 (e.g., standard or commonly available intravenous tubing, intravenous connectors, saline bags, or the like) to be used as part of a fluid system 16 in accordance with the present invention.

Figure 15:
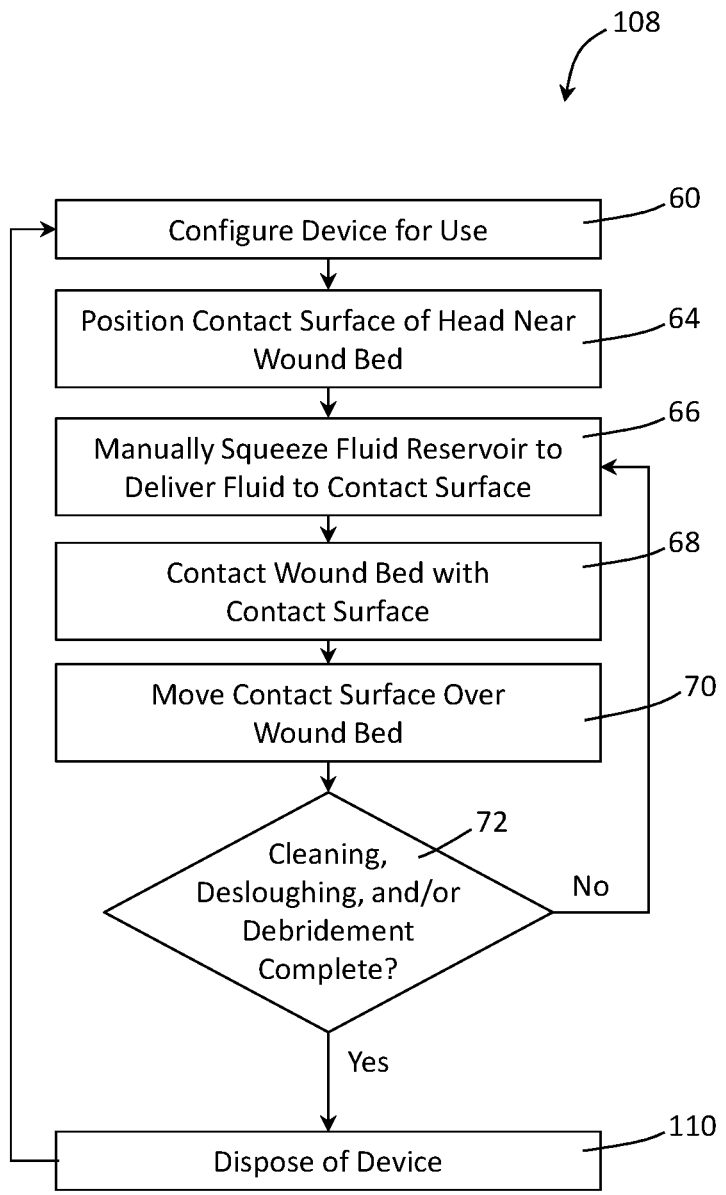
FIG. 15 is a block diagram of an alternative embodiment of a method for using a wound-care device in accordance with the present invention.

Referring to FIG. 15, in selected embodiments, an alternative method 108 for cleansing, desloughing, and/or debriding a wound bed may begin when a device 10 is configured 60 for use. Configuring 60 a device 10 for use may include selecting a device 10 with an appropriate contact surface 36, opening packaging containing the device 10, and installing a fluid reservoir 44 (e.g., selecting a saline bullet, removing a cap of the saline bullet, inserting an outlet 88 of the saline bullet into a back portion 78b of an aperture 78 of a head 14). Thereafter, a device 10 may be moved to position 64 a contact surface 36 proximate a wound bed.

To initiate cleansing, desloughing, and/or debriding, a user may manually squeeze 66 a fluid reservoir 44 to create a flow of fluid to the contact surface 36 and/or place 68 a contact surface 36 in contact with the wound bed. Thereafter, the user may move 70 the contact surface 36 over the wound bed. Moving 70 the contact surface 36 with respect to the wound bed in combination with a rinsing effect produced by the fluid may tend to clean, deslough, and/or debride the wound bed. The moving 70 of the contact surface may be side to side, front to back, at some angle, in small circles, or the like or a combination or sub-combination thereof. Accordingly, a user may continue to dispense 66 fluid, apply 68 the contact surface 36 to the wound bed, and move 70 the contact surface 36 over the wound bed until it is determined 72 that the cleansing, desloughing, and/or debriding is complete. Once it is complete, the device 10 may be discarded 110.

Figure 16:
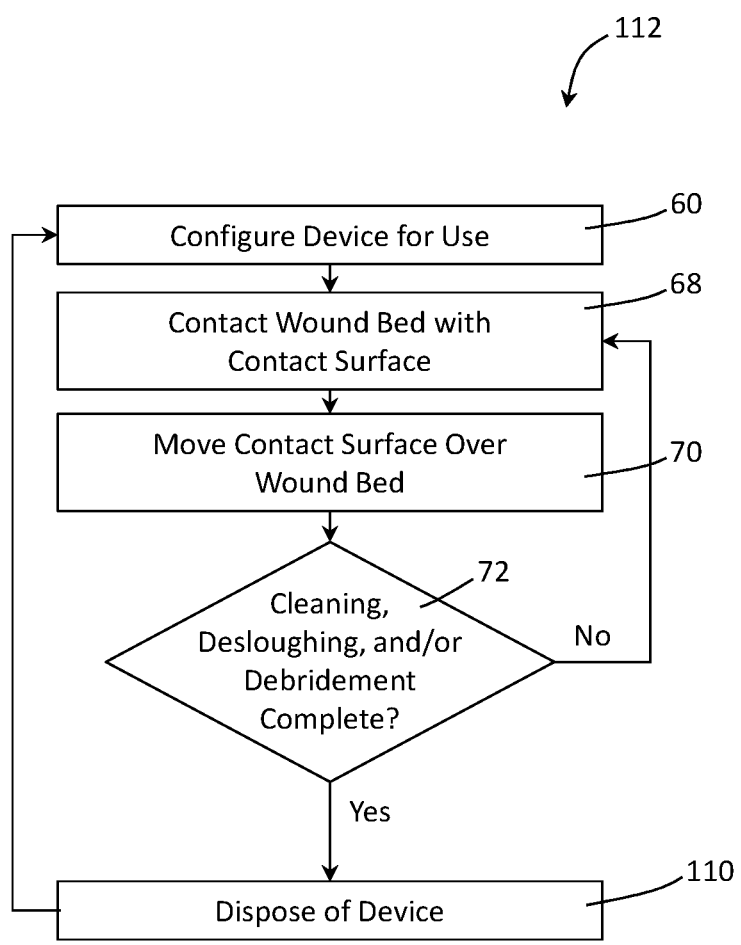
FIG. 16 is a block diagram of another alternative embodiment of a method for using a wound-care device in accordance with the present invention.
Figure 20:
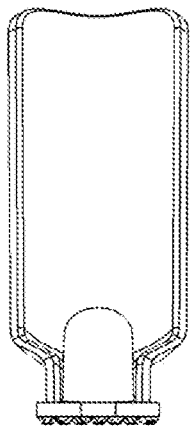
FIG. 20 is a front view of the main body and head portions of the wound-care device of FIG. 10.
Figure 22:
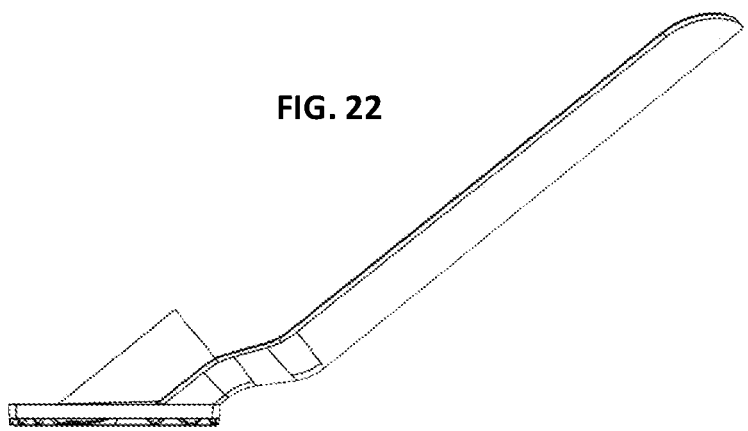
FIG. 22 is a first side view of the main body and head portions of the wound-care device of FIG. 10.
Figure 21:
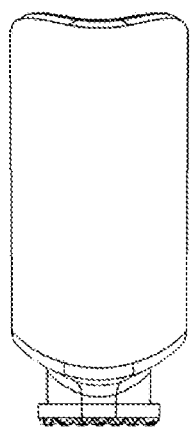
FIG. 21 is a rear view of the main body and head portions of the wound-care device of FIG. 10.
Figure 23:
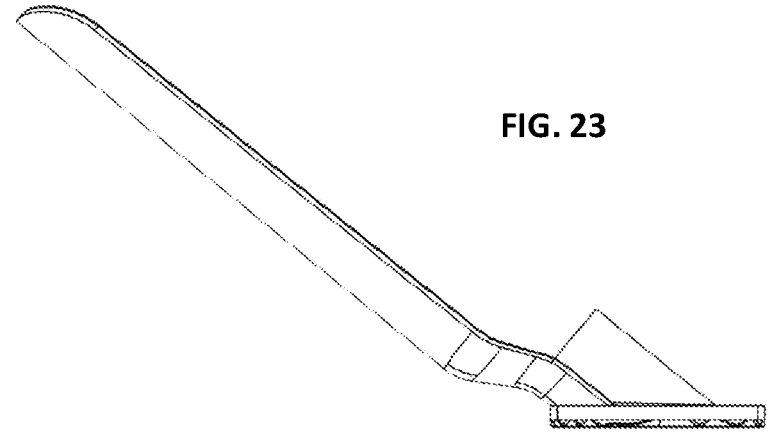
FIG. 23 is a second, opposite side view of the main body and head portions of the wound-care device of FIG. 10.

Referring to FIG. 16, in selected embodiments, another alternative method 112 for cleansing, desloughing, and/or debriding a wound bed may begin when a device 10 is configured 60 for use. Configuring 60 a device 10 for use may include removing the device from sterile packaging. To initiate cleansing, desloughing, and/or debriding, a user may manually place 68 a contact surface 36 in contact with the wound bed. Thereafter, the user may move 70 the contact surface 36 over the wound bed. Moving 70 the contact surface 36 with respect to the wound bed may tend to clean, deslough, and/or debride the wound bed. If using a finger (e.g., an index finger) to guide a device 10 or a head 14 of a device 10, a user may selectively change a pressure and/or orientation of a head 14 with respect to a wound bed to more precisely control an outcome of the procedure. Accordingly, a user may continue to apply 68 the contact surface 36 to the wound bed and move 70 the contact surface 36 over the wound bed until it is determined 72 that the cleansing, desloughing, and/or debriding is complete. Once it is complete, the device 10 may be discarded 110.

In certain embodiments, a method 112 may be preceded by the application of a fluid or the like to a wound bed. Accordingly, a method 112 may benefit from the fluid without the fluid being applied while a contact surface 36 is in contact 68 with a wound bed or as a contact surface 36 is moved 70 over a wound bed.

In other embodiments, a wound may be treated in one session using a combination of two methods 108, 112. For example, for a first period of time, a user may employ various steps 64, 66, 68, 70 corresponding to a "wet" method 108, then remove a fluid reservoir 44 (e.g., remove a saline bullet positioned within a concavity 90) and transition to employing various steps 68, 70 corresponding to a "dry" method 112 wherein a finger placed within a concavity 90 to provide greater control over the force, orientation, etc. of a device 10. Such a hybrid method may end by using fluid remaining in the fluid reservoir 44 to flush or rinse of the wound bed.

Referring to FIGS. 17-31, different wounds may fall on different locations within a wound infection continuum. Accordingly, the treatment needed for different wounds may also vary. For example, in certain situations, a wound infection continuum may be divided into multiple zones (e.g., three zones). A first zone may correspond to a lower level of infection, while one or more other zones may correspond to one or more higher levels of infection. Accordingly, one or more methods 58, 108, 112 in accordance with the present invention may enable wounds corresponding to the first zone to be treated differently from wounds corresponding to one or more other zones.

For example, if an examination of a wound bed reveals that a wound corresponds to the second zone or other higher zone of a wound infection continuum, a user (e.g., a medical professional) may select, install, and/or use a contact surface 36 that is relatively aggressive. Conversely, if an examination of a wound bed reveals that a wound corresponds to the first zone of a wound infection continuum, a user may select, install, and/or use a contact surface 36 that is less aggressive.

Alternatively, in one or more methods 58, 108, 112 in accordance with the present invention, a wound may be evaluated based on the presence and/or nature of devitalized tissue. For example, in certain situations, a wound may be classified into one of three situations. A first situation may correspond to devitalized tissue that is firmly adherent. A second situation may correspond to devitalized tissue that is loosely adherent. A third situation may correspond to a wound that could simply benefit from cleansing. Accordingly, one or more methods 58, 108, 112 in accordance with the present invention may enable wounds corresponding to the first, second, and third situations to be treated differently.

For example, if an examination of a wound bed reveals that a wound corresponds to devitalized tissue that is firmly adherent, a user may select, install, and/or use a contact surface 36 that is relatively aggressive. Such as a contact surface 36 may be referred to as a debridement surface 36a. If an examination of a wound bed reveals that a wound corresponds to devitalized tissue that is loosely adherent, a user may select, install, and/or use a contact surface 36 that is intermediately aggressive. Such a contact surface 36 may be referred to as a desloughing surface 36b. If an examination of a wound bed reveals that a wound could simply benefit from cleansing, a user may select, install, and/or use a contact surface 36 that is not aggressive. Such a contact surface 36 may be referred to as a cleansing surface 36c.

A contact surface 36 in accordance with the present invention may have any suitable configuration. In general, increasing the sharpness and/or number of the edges of the various extensions 82 of a contact surface 36 may result in a more aggressive effect when applied to a wound bed. Accordingly, a cleaning surface 36c may have few if any sharp edges, a desloughing surface 36b may have an intermediate number of edges and/or edges of intermediate sharpness, and a debridement surface 36a may have a significant number of edges and/or edges of increased sharpness.

FIGS. 17-23 show one embodiment of a simplified main body 12 and head 14 combination where the head 14 includes (e.g., is monolithically formed or molded to have) a cleansing surface 36c.

FIGS. 24-27 show one embodiment of a simplified main body 12 and head 14 combination where the head 14 includes (e.g., is monolithically formed or molded to have) a desloughing surface 36b.

Figures 28, 29, 30, 31:
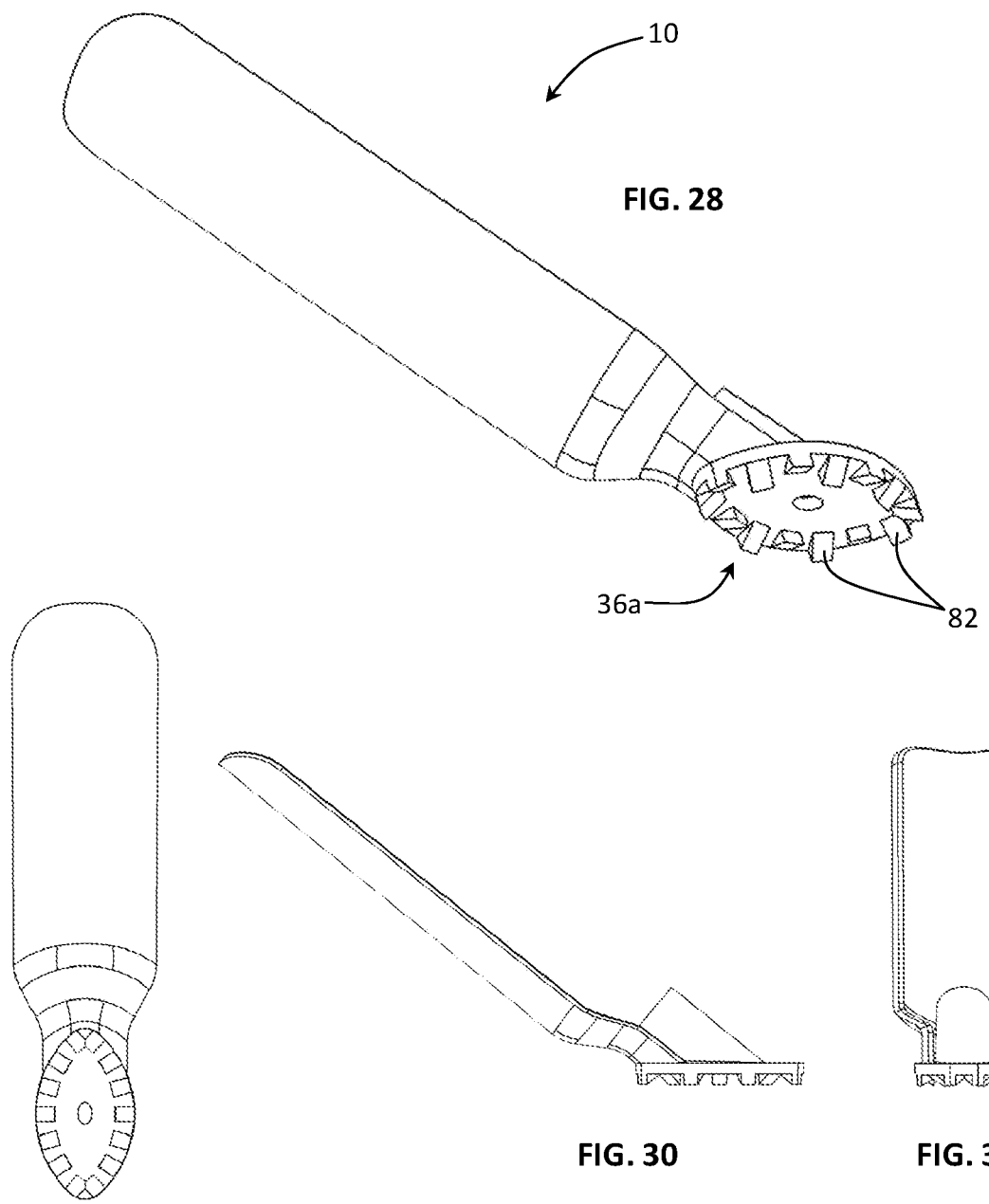
FIG. 28 is a perspective view of another alternative embodiment of a wound-care device in accordance with the present invention.
FIG. 29 is a bottom view of the wound-care device of FIG. 28.
FIG. 30 is a side view of the wound-care device of FIG. 28.
FIG. 31 is a front view of the wound-care device of FIG. 28.
Figure 32:
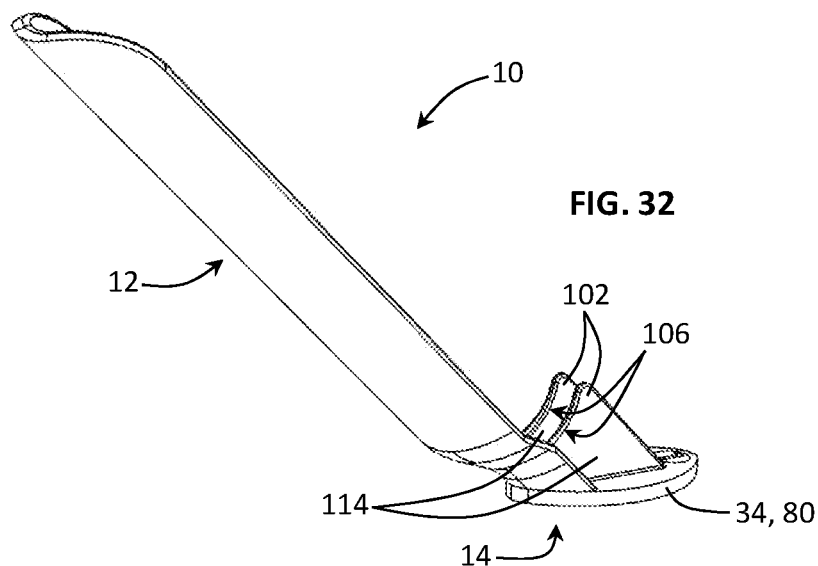
FIG. 32 is a perspective view of another alternative embodiment of a wound-care device in accordance with the present invention.
Figure 33:
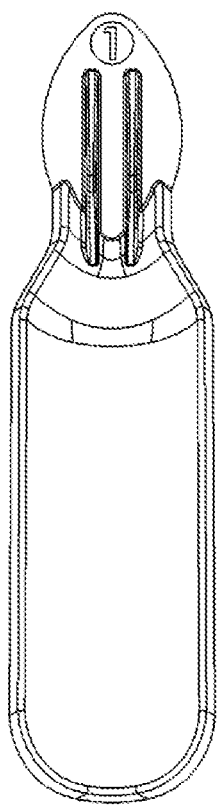
FIG. 33 is a top view of the wound-care device of FIG. 32.
Figure 34:
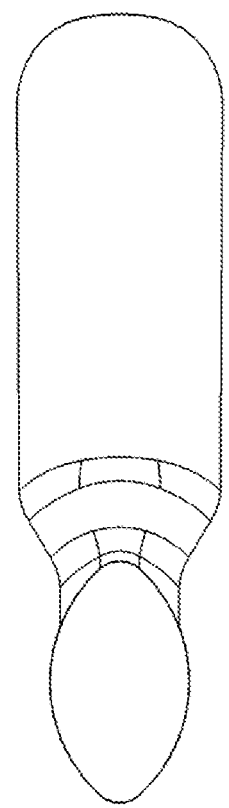
FIG. 34 is a bottom view of the wound-care device of FIG. 32.
Figure 35:
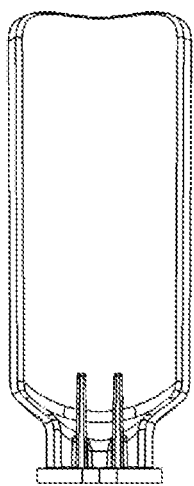
FIG. 35 is a front view of the wound-care device of FIG. 32.
Figure 37:
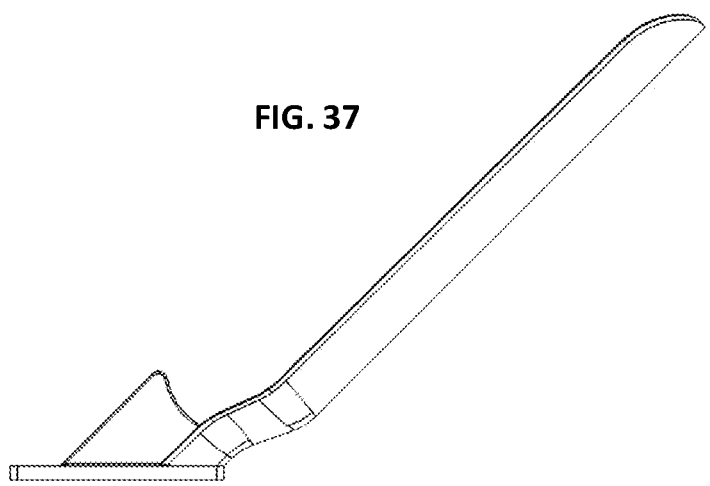
FIG. 37 is a first side view of the wound-care device of FIG. 32.
Figure 36:
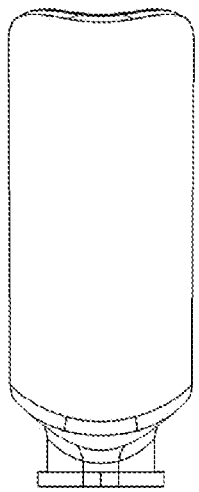
FIG. 36 is a rear view of the wound-care device of FIG. 32.
Figure 38:
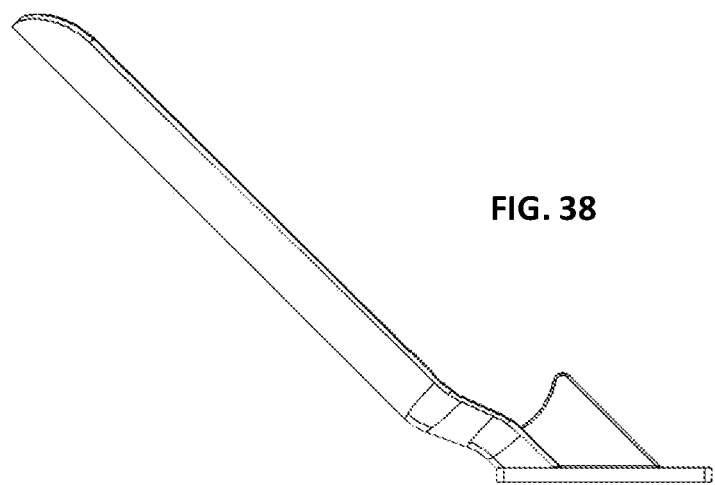
FIG. 38 is a second, opposite side view of the wound-care device of FIG. 32.
Figure 39:
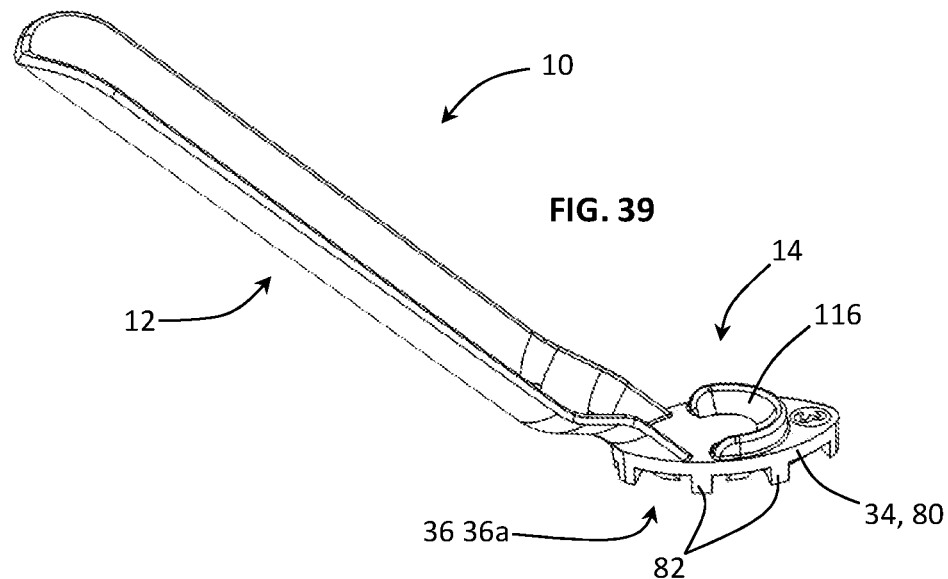
FIG. 39 is a perspective view of another alternative embodiment of a wound-care device in accordance with the present invention.
Figure 40:
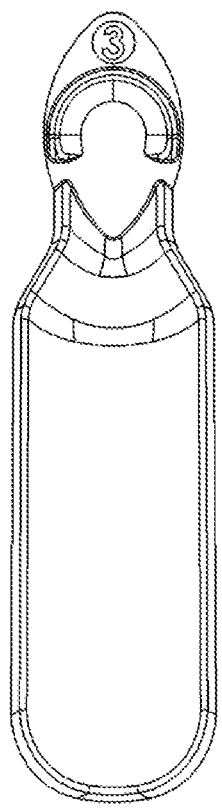
FIG. 40 is a top view of the wound-care device of FIG. 39.
Figure 41:
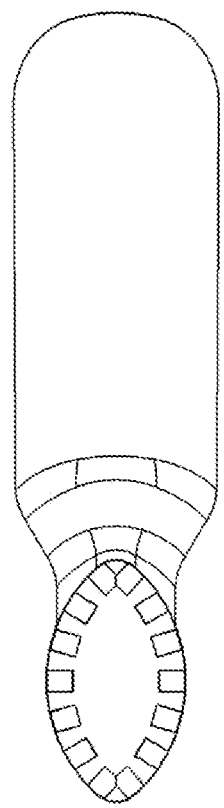
FIG. 41 is a bottom view of the wound-care device of FIG. 39.
Figure 42:
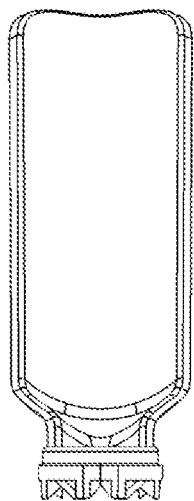
FIG. 42 is a front view of the wound-care device of FIG. 39.
Figure 44:
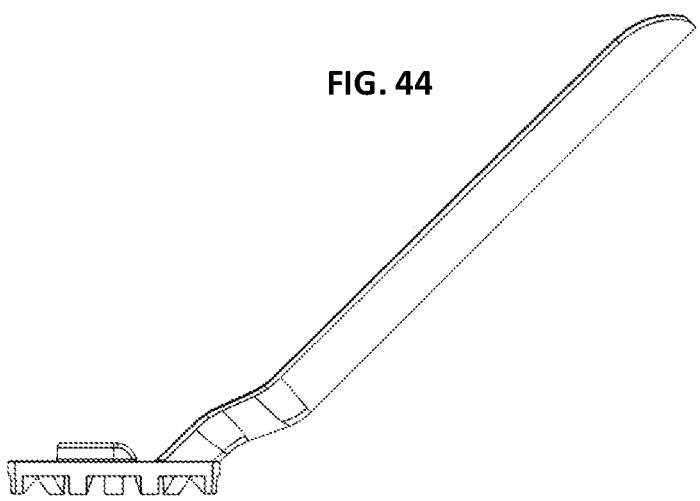
FIG. 44 is a first side view of the wound-care device of FIG. 39.
Figure 43:
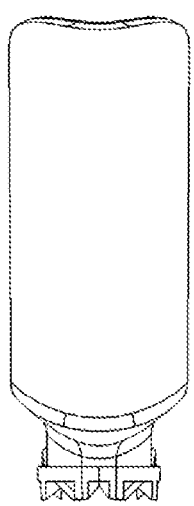
FIG. 43 is a rear view of the wound-care device of FIG. 39.
Figure 45:
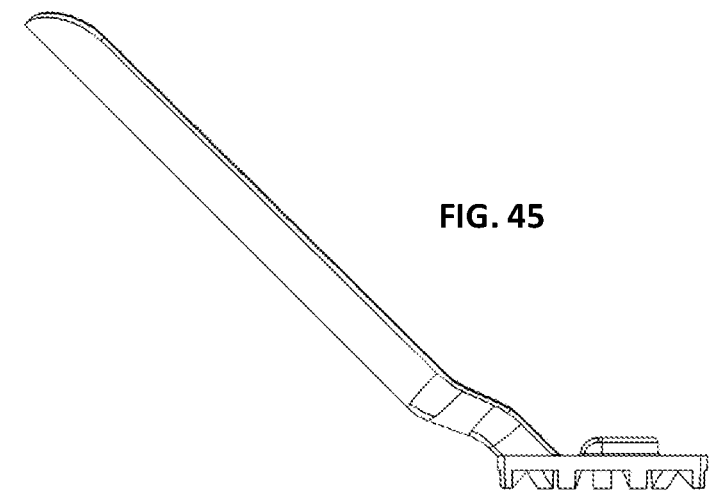
FIG. 45 is a second, opposite side view of the wound-care device of FIG. 39.
Figure 49:
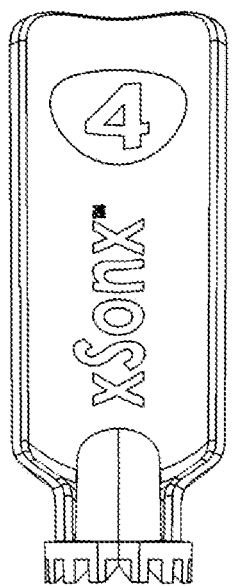
FIG. 49 is a front view of the wound-care device of FIG. 46.
Figure 51:
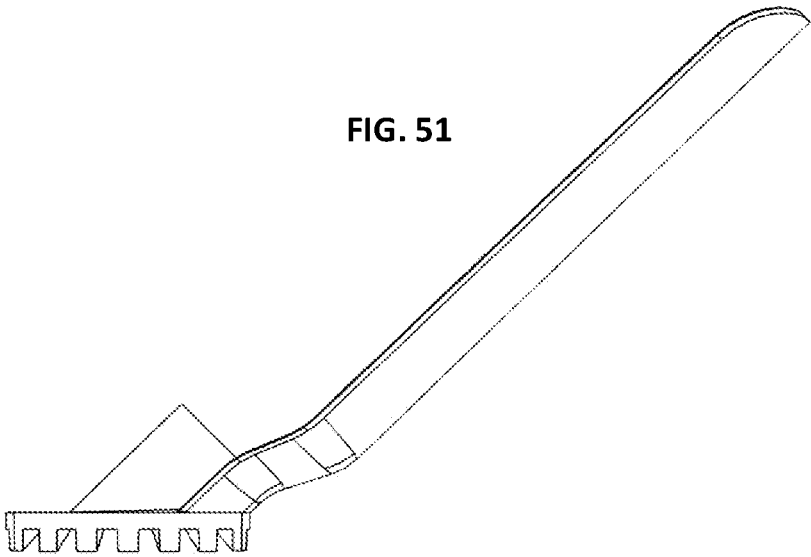
FIG. 51 is a first side view of the wound-care device of FIG. 46.
Figure 50:
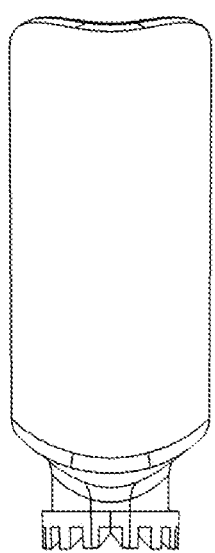
FIG. 50 is a rear view of the wound-care device of FIG. 46.
Figure 52:
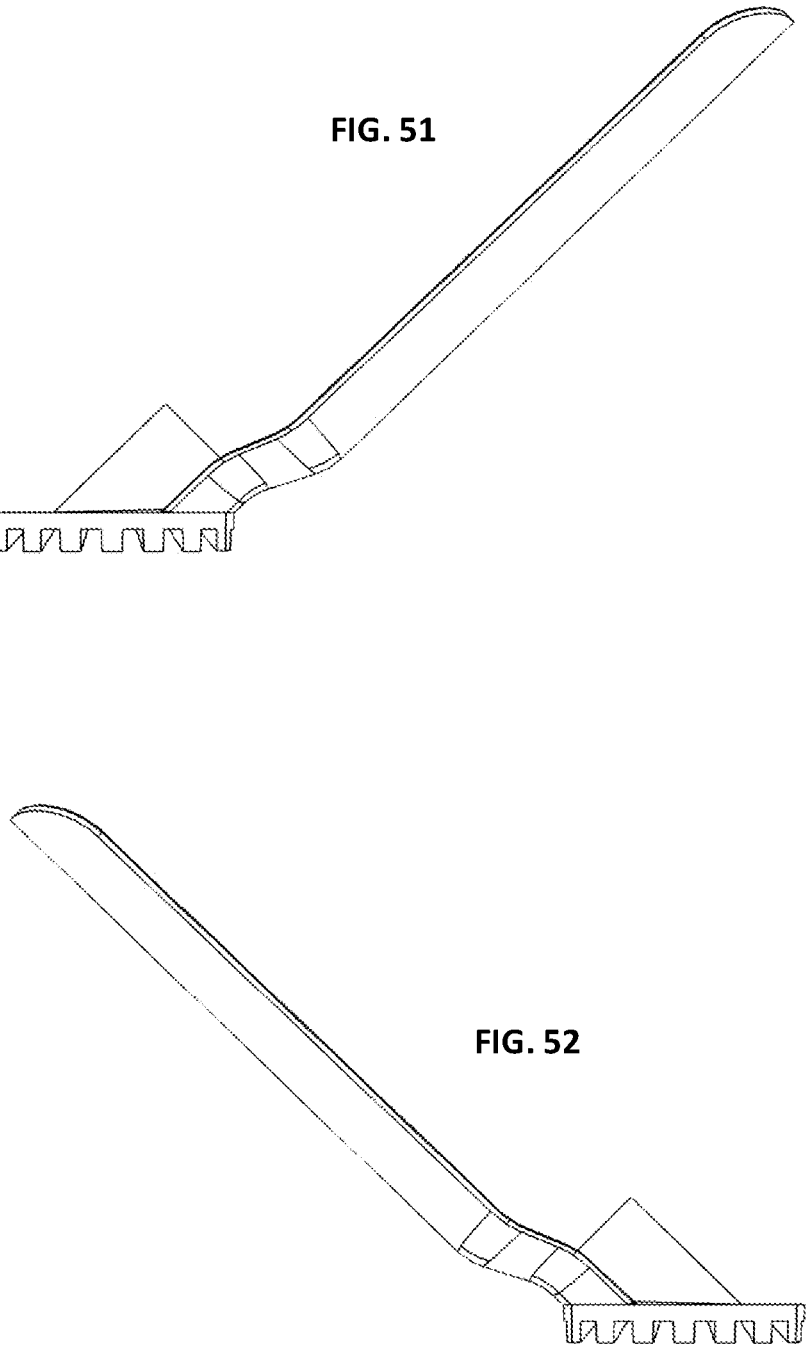
FIG. 52 is a second, opposite side view of the wound-care device of FIG. 46.
Figure 53:
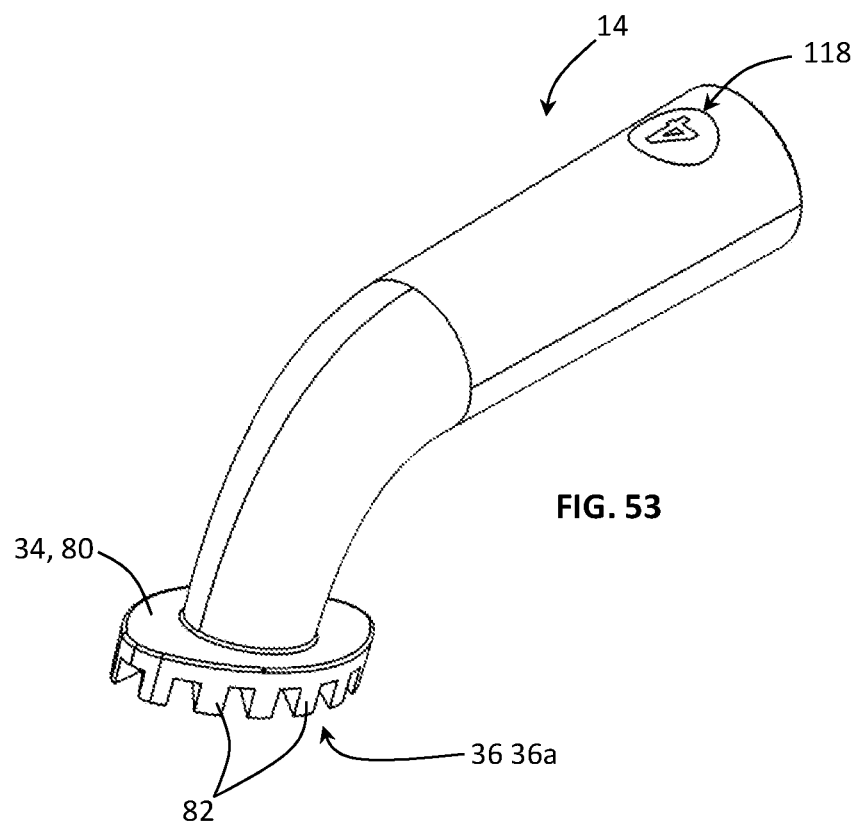
FIG. 53 is a perspective view of another alternative embodiment of a removable head for a wound-care device in accordance with the present invention.
Figure 54:
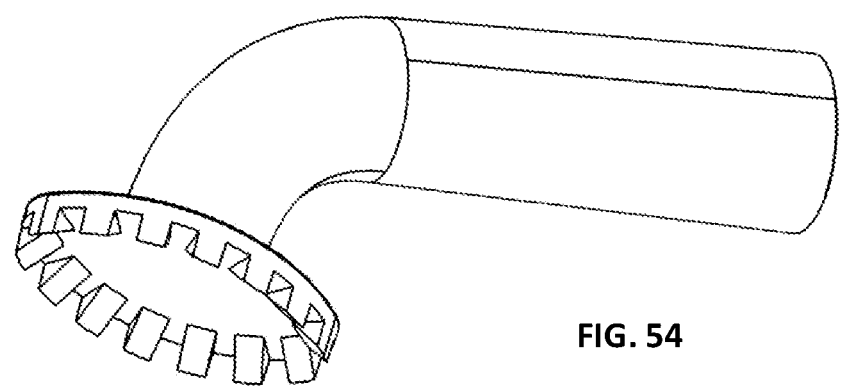
FIG. 54 is another perspective view of the removable head of FIG. 53.
Figure 55:
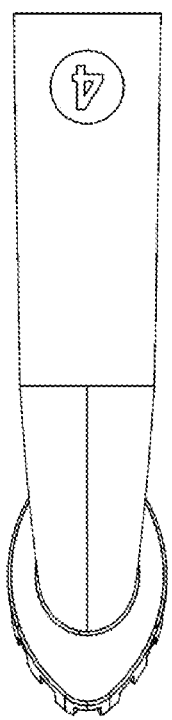
FIG. 55 is a top view of the removable head of FIG. 53.
Figure 56:
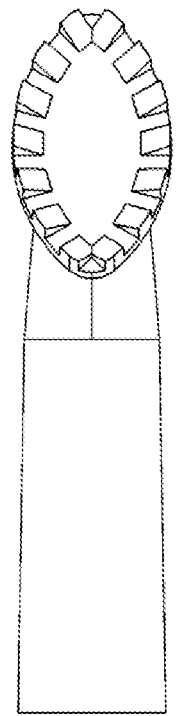
FIG. 56 is a bottom view of the removable head of FIG. 53.
Figure 57:
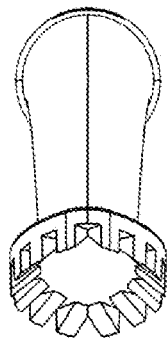
FIG. 57 is a front view of the removable head of FIG. 53.
Figure 58:
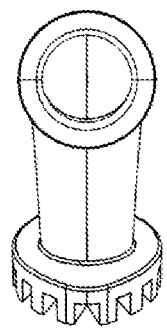
FIG. 58 is a rear view of the removable head device of FIG. 53.
Figure 59:
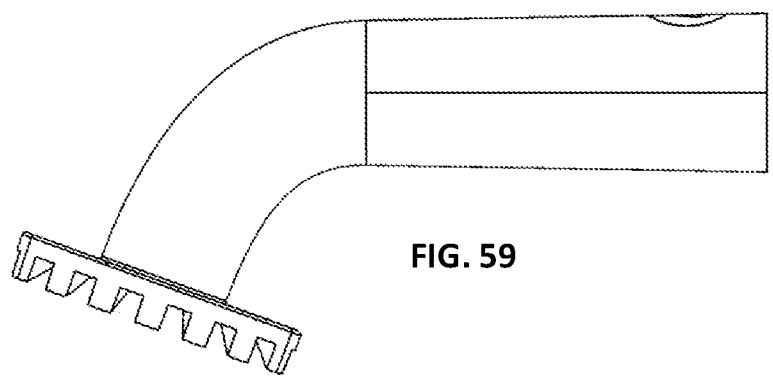
FIG. 59 is a first side view of the removable head device of FIG. 53.
Figure 60:
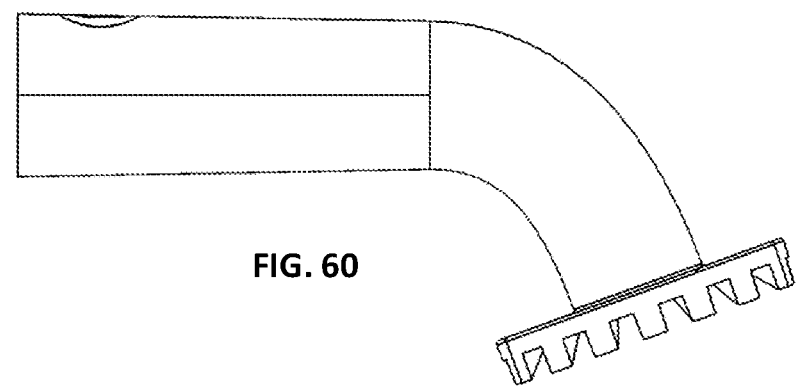
FIG. 60 is a second, opposite side view of the removable head of FIG. 53.
Figure 61:
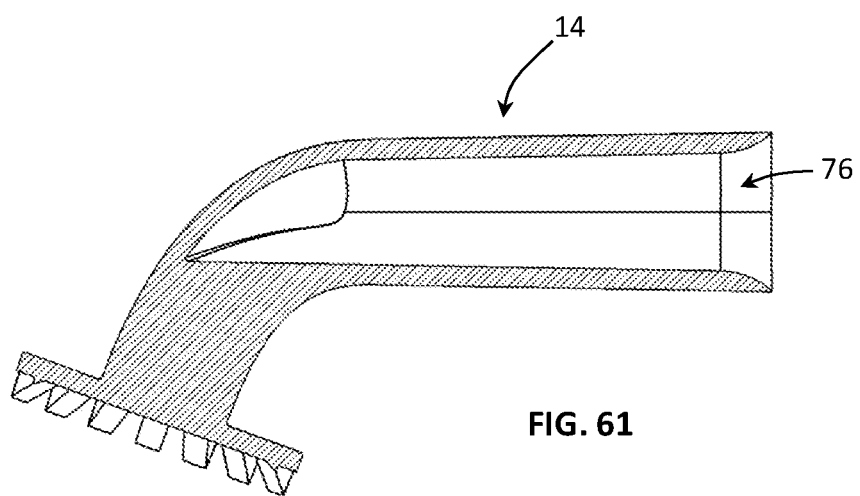
FIG. 61 is a side cross-sectional view of the removable head of FIG. 53.
Figure 62:
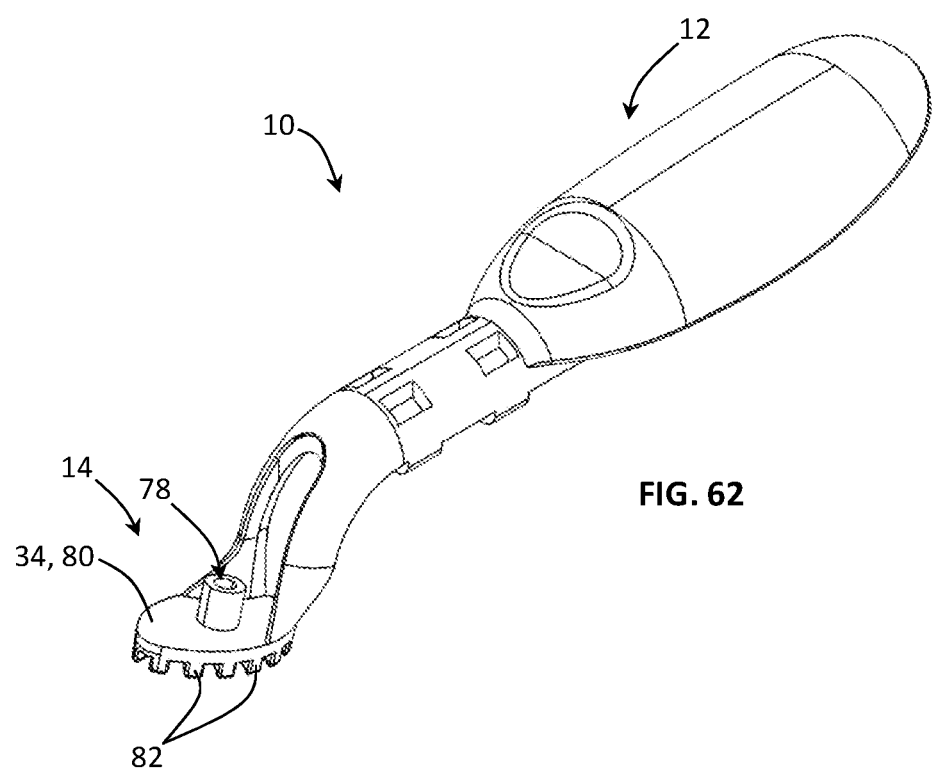
FIG. 62 is a perspective view of another alternative embodiment of a wound-care device in accordance with the present invention.
Figure 63:
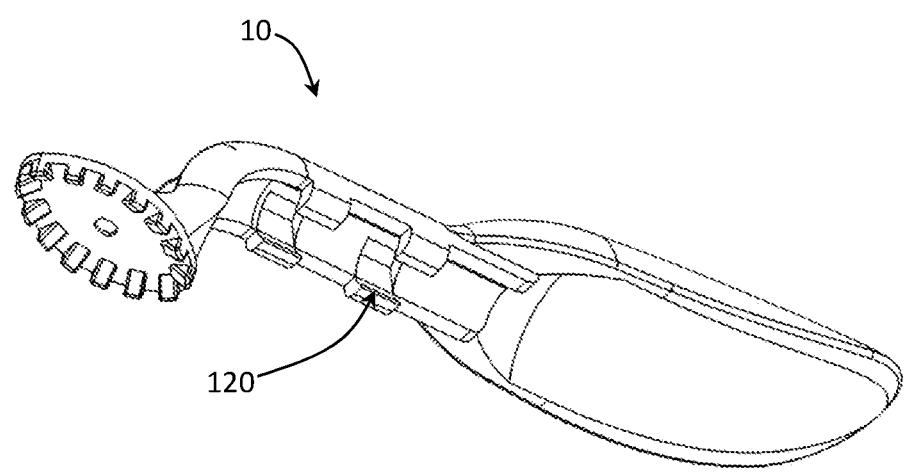
FIG. 63 is another perspective view the wound-care device of FIG. 62.
Figure 64:
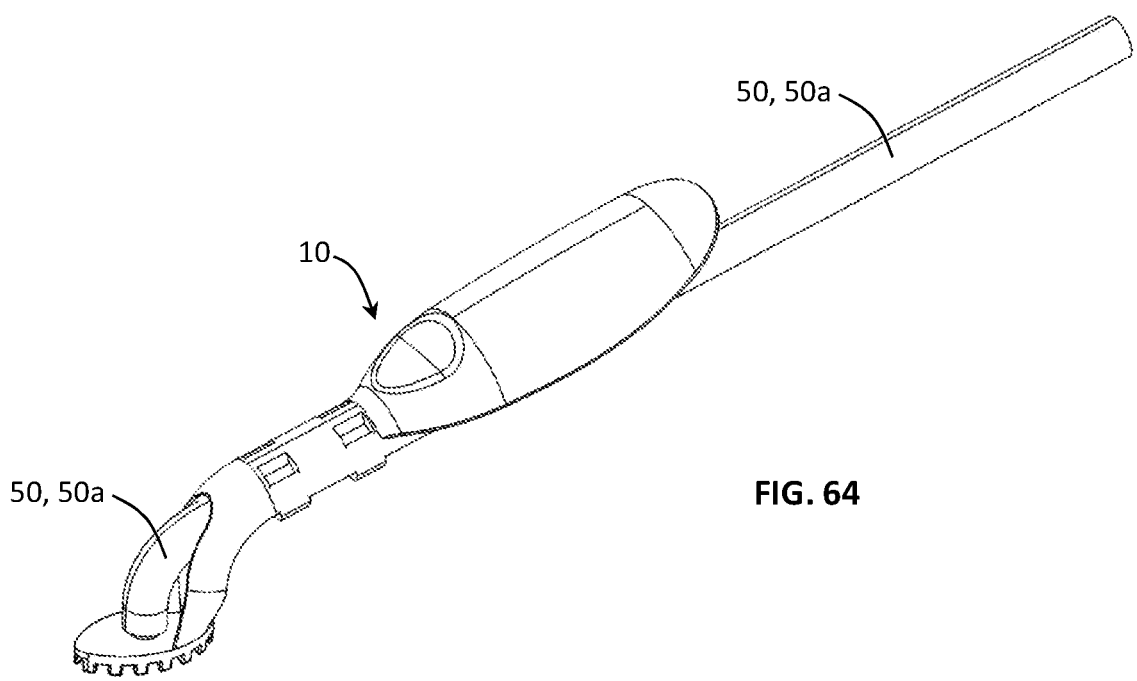
FIG. 64 is a perspective view the wound-care device of FIG. 62 with a tube applied thereto that may extend to a remote fluid reservoir.
Figure 65:
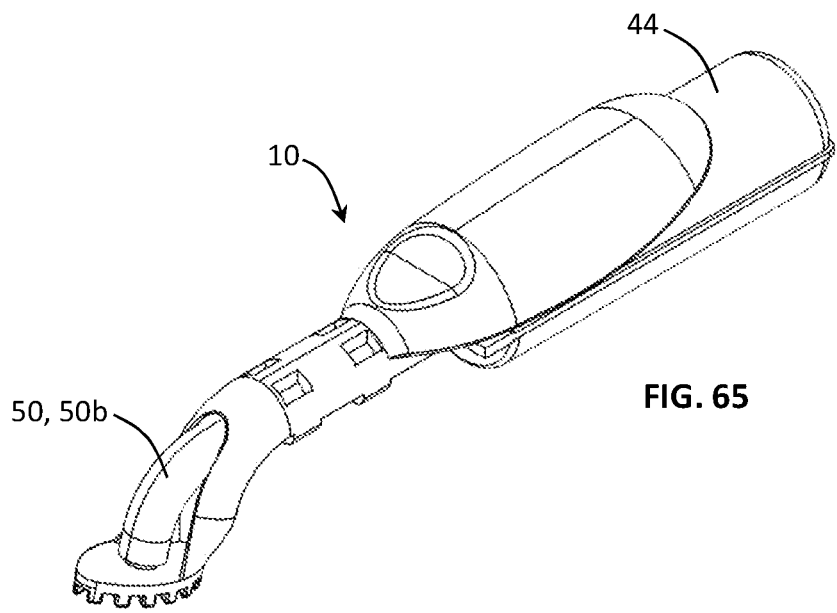
FIG. 65 is a perspective view the wound-care device of FIG. 62 with a fluid reservoir applied thereto.
Figure 66:
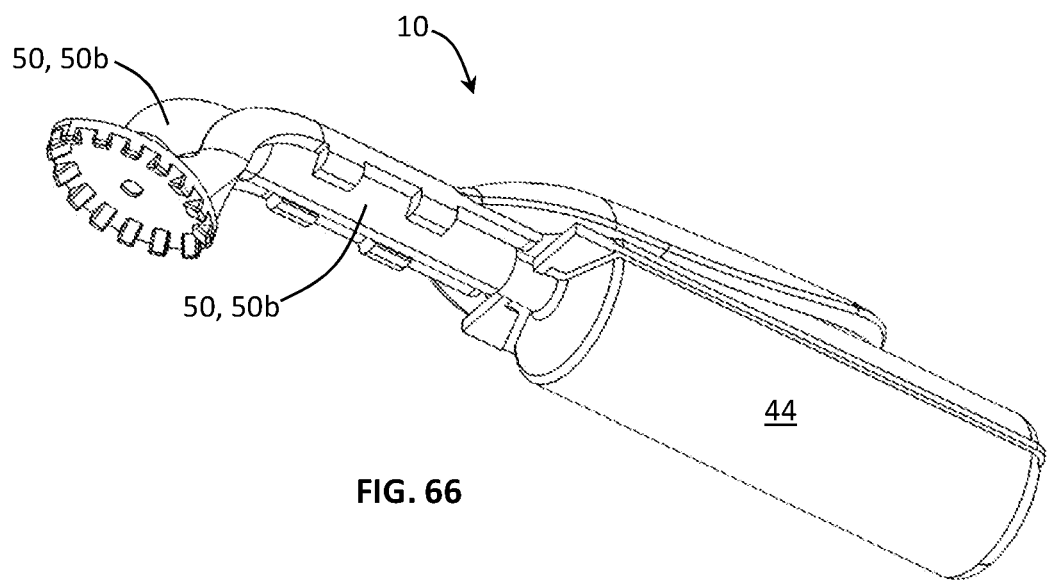
FIG. 66 is another perspective view the wound-care device of FIG. 62 with a fluid reservoir applied thereto.
Figure 67:
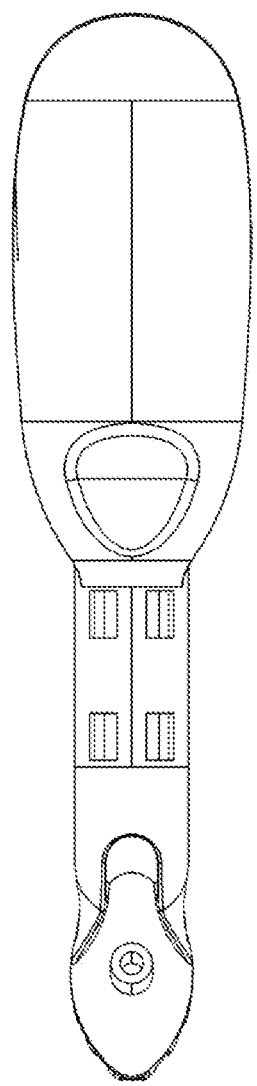
FIG. 67 is a top view of the wound-care device of FIG. 62.
Figure 68:
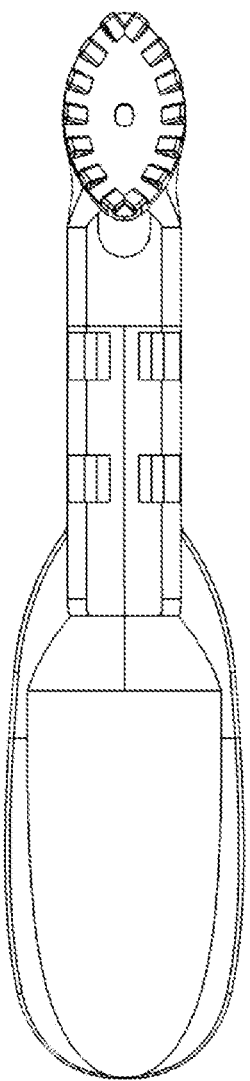
FIG. 68 is a bottom view of the wound-care device of FIG. 62.
Figure 73:
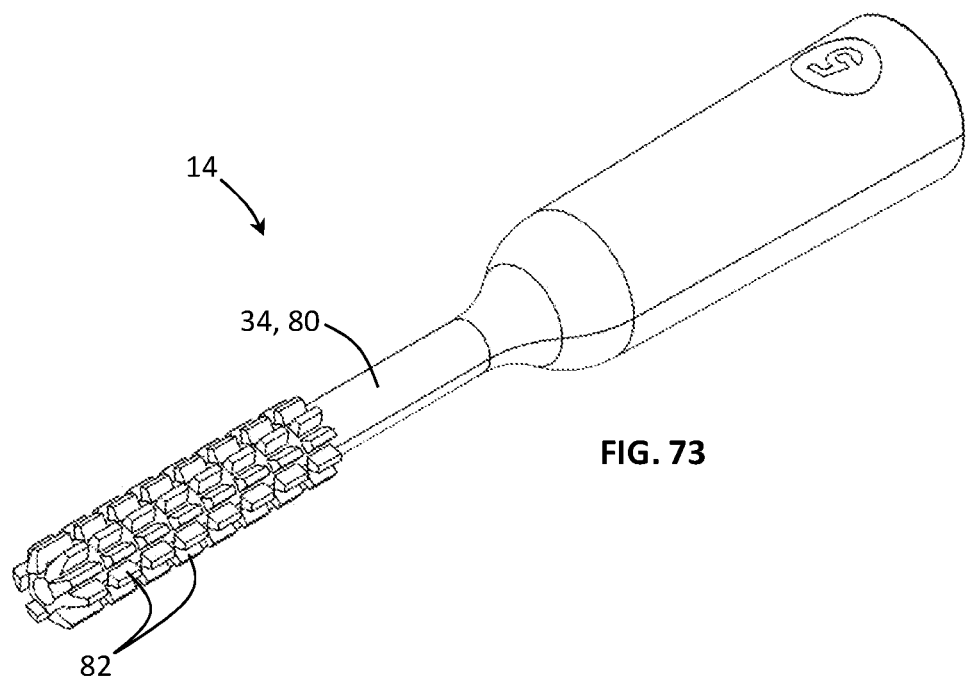
FIG. 73 is a perspective view of another alternative embodiment of a removable head for a wound-care device in accordance with the present invention.
Figure 74:
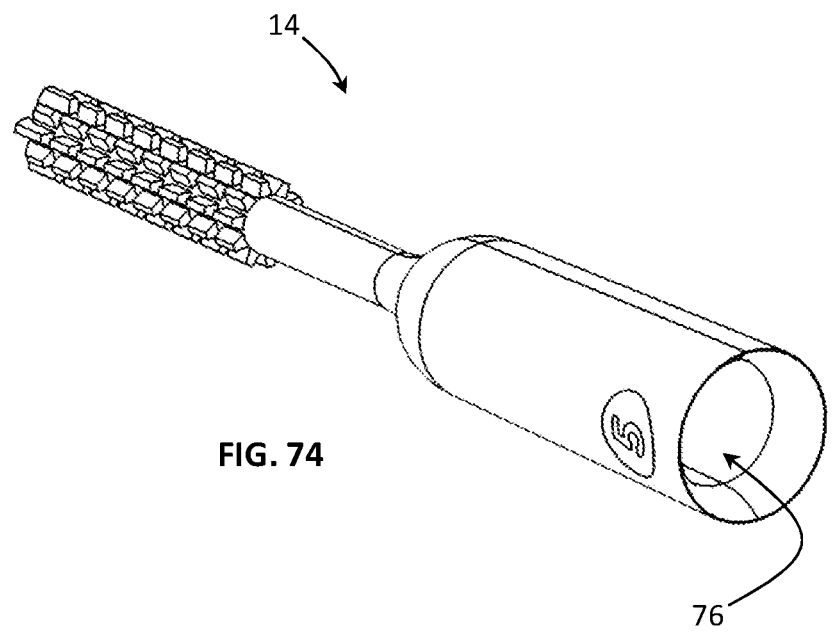
FIG. 74 is another perspective view of the removable head of FIG. 73.
Figure 75:
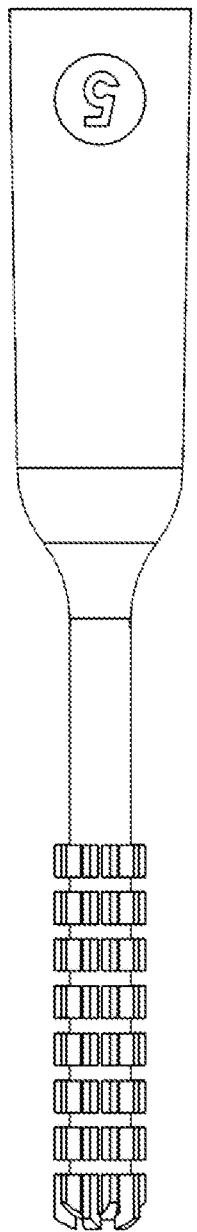
FIG. 75 is a top view of the removable head of FIG. 73.
Figure 76:
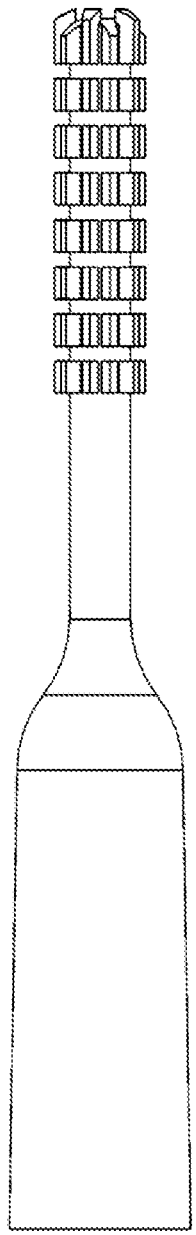
FIG. 76 is a bottom view of the removable head of FIG. 73.
Figure 77:
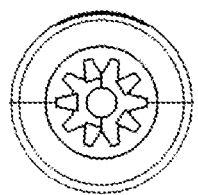
FIG. 77 is a front view of the removable head of FIG. 73.
Figure 78:
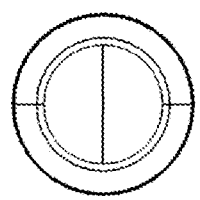
FIG. 78 is a rear view of the removable head device of FIG. 73.
Figure 79:
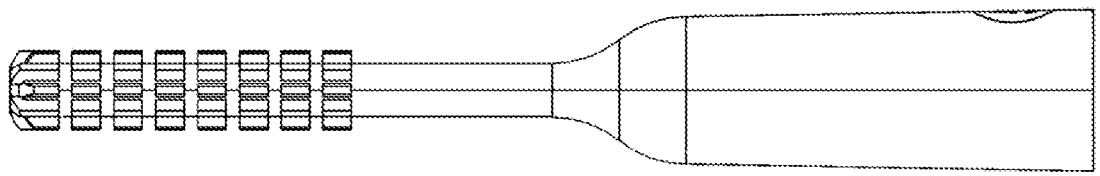
FIG. 79 is a first side view of the removable head device of FIG. 73.
Figure 80:
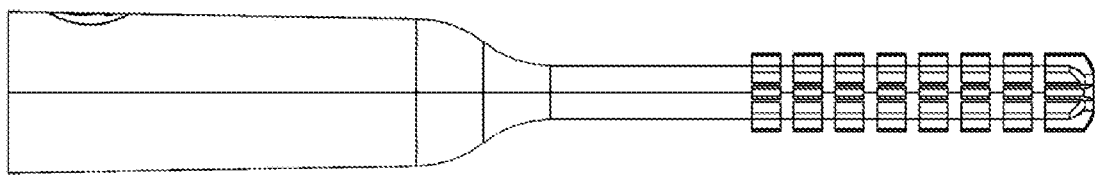
FIG. 80 is a second, opposite side view of the removable head of FIG. 73.
Figure 81:
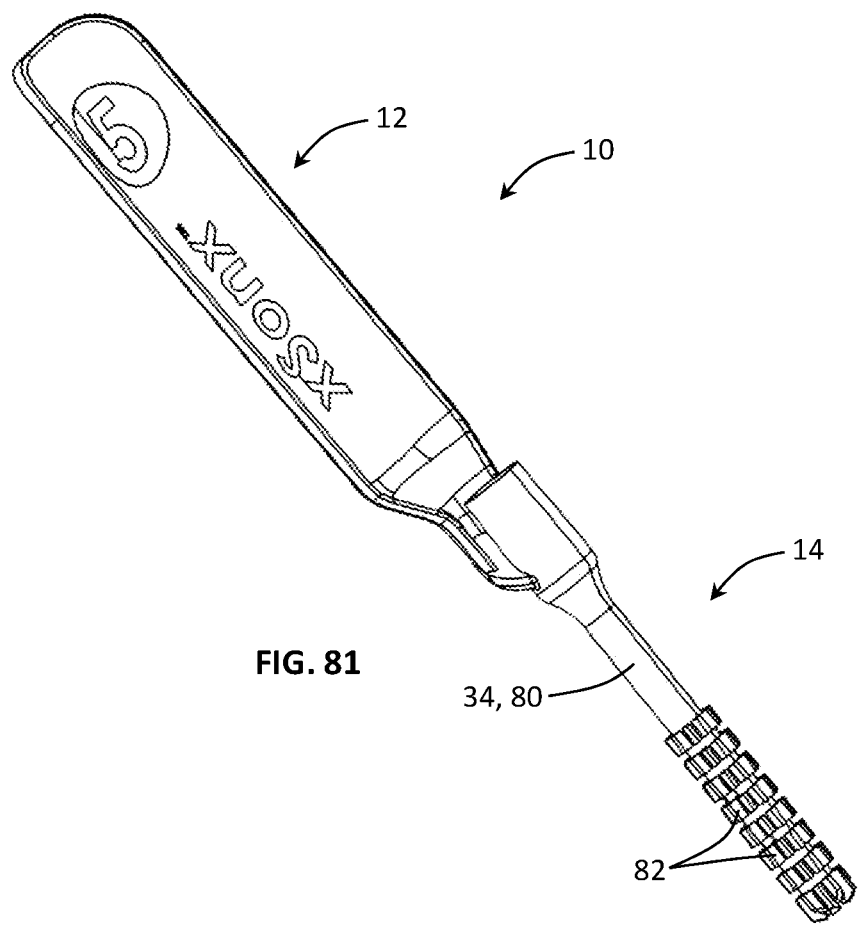
FIG. 81 is a perspective view of another alternative embodiment of a wound-care device in accordance with the present invention.
Figure 82:
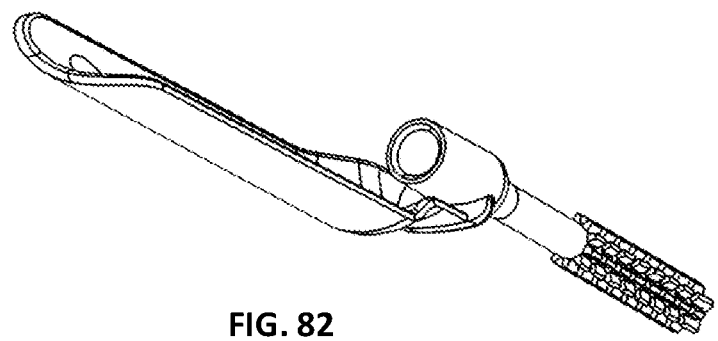
FIG. 82 is another perspective view of the removable head of FIG. 81.
Figure 83:
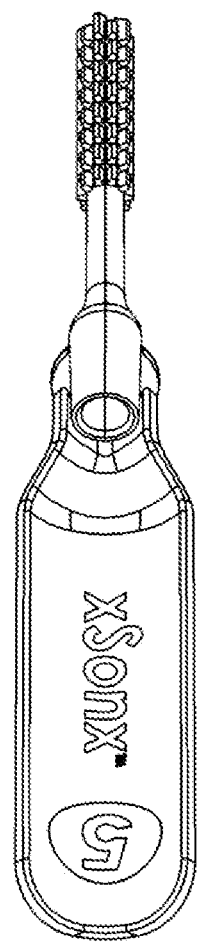
FIG. 83 is a top view of the wound-care device of FIG. 81.
Figure 84:
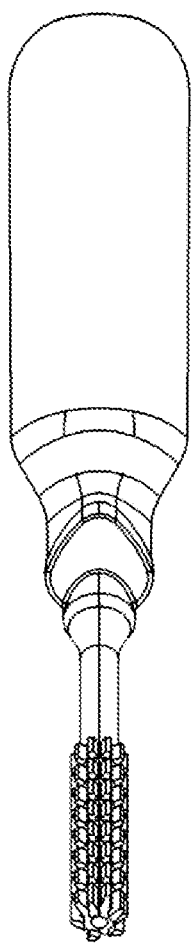
FIG. 84 is a bottom view of the wound-care device of FIG. 81.
Figure 85:
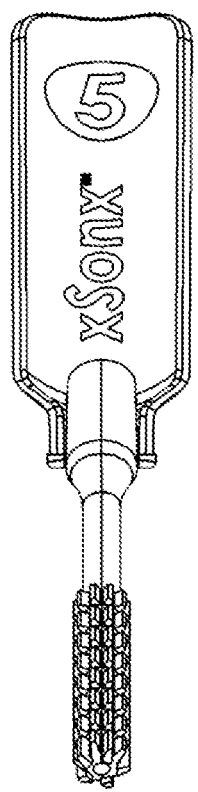
FIG. 85 is a front view of the wound-care device of FIG. 81.
Figure 86:
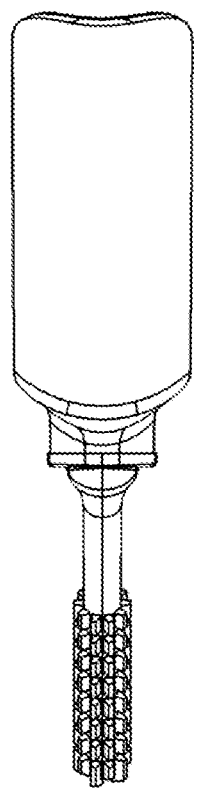
FIG. 86 is a rear view of the wound-care device of FIG. 81.
Figure 87:
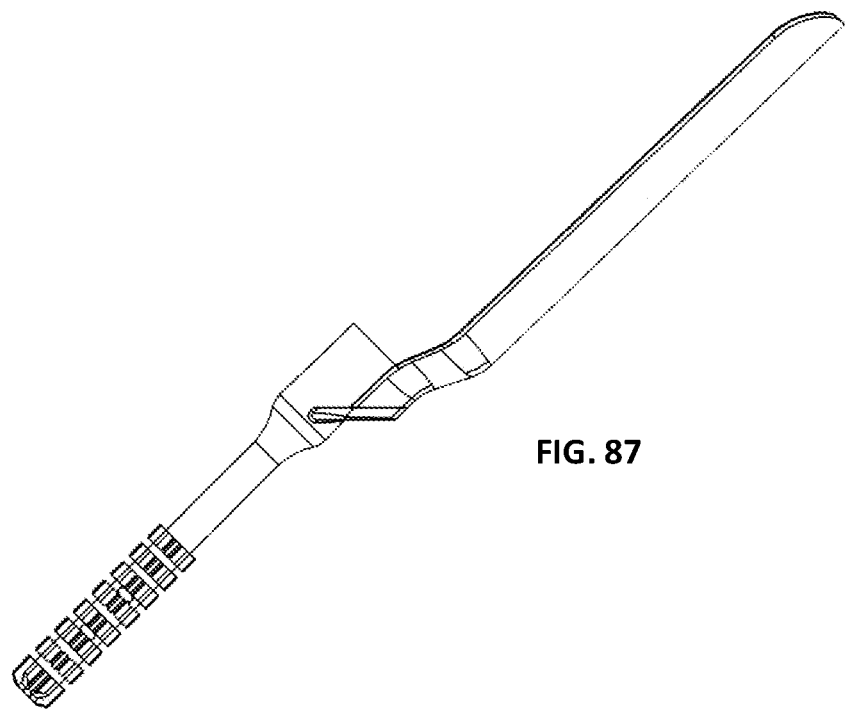
FIG. 87 is a first side view of the wound-care device of FIG. 81.
Figure 88:
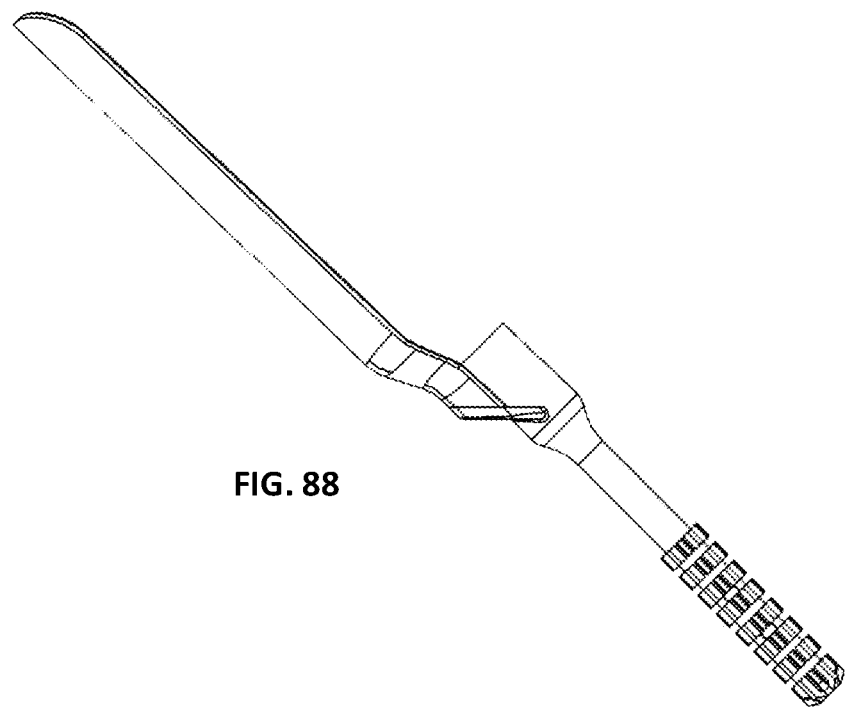
FIG. 88 is a second, opposite side view of the wound-care device of FIG. 81.

FIGS. 28-31 show one embodiment of a simplified main body 12 and head 14 combination where the head 14 includes (e.g., is monolithically formed or molded to have) a debridement surface 36a. In selected embodiments, the extensions 82 of a contact surface 36 (e.g., a debridement surface 36a) may alternate in height or be laterally offset side to side. For example, as shown in FIG. 28, the two distal most and two proximal most extensions 82 may be oriented so that the highest portion thereof is positioned to the outside for better cutting at the apices of the head 14, but the extensions 82 may otherwise alternate to make a broader cutting path.

Referring to FIGS. 32-38, in selected embodiments, a simplified main body 12 and head 14 combination may be formed without an aperture 78 for fluid to pass through the head 14. Rather, the combination may include one or more ribs 114 that extend to connect and/or reinforce a base 80 of a head 14 with respect to a main body 12 or handle portion 12. In certain embodiments, such ribs 114 may include proximal ends 102 having a curvature 106 formed therein that follows or replicates a portion of the curvature of a finger tip. Accordingly, one or more ribs 114 may be configured to engage a tip of a finger of a user.

In selected embodiments, a head 14 may include a base 80 without any extensions 82 projecting therefrom. For example, as shown in FIG. 32-38, a front side 40 of a base 80 may be substantially flat. Such a flat surface may provide a location for adhering a contact surface 36 comprising a scrubbing pad (e.g., open cell foam, closed cell foam, soft silicone, or other semi-abrasive surface). Alternatively, a base 80 may provide a location or structure to which an appropriate contact surface 36 may be fastened, snapped, slid over both ends of the base 80, or otherwise secured to a head 14. A main body 12 may, therefore, be provided in a non-sterile condition and still be safely used when a sterile contact surface 36 is secured in place. Accordingly, in such embodiments, a contact surface 36 may comprise or be formed by a scrubbing pad or the like of a material that is dissimilar to a material forming a head 14 or a head 14 and main body 12.

Referring to FIGS. 39-45, in selected embodiments, a simplified main body 12 and head 14 combination may be formed with a base 80 that includes a wedge 116, ramp 116, crescent 116, or the like that provides an abutment for a finger tip of a user. Accordingly, there are various ways in which a base 80 may be configured to engage a tip of a finger of a user.

Referring to FIGS. 46-52, an alternative embodiment of a simplified main body 12 and head 14 combination is illustrated. As shown, a head 14 may include (e.g., may be monolithically formed or molded to have) a debridement surface 36a. In selected embodiments, the extensions 82 of a contact surface 36 (e.g., a debridement surface 36a) may face outside (i.e., have a highest portion along an outside edge) so that the outer edge of the head 14 may better engage and cut into tissue in need of debridement. Additionally, a head 14 may be manipulated as it engages a wound bed to pull the head 14 along an outer edge thereof, thereby making a more sharply debrided wound edge as may be desired by a medical professional using the device 10 or supervising use thereof. For example, a head 14 may be manipulated in a carving motion along the edges thereof, thereby giving the medical professional maximal control over the aggressiveness of the debridement obtained during the procedure.

In selected embodiments, a device 10 (e.g., a main body 12 and/or a head 14) in accordance with the present may have a number 118, letter 118, marking 118, symbol 118, color code 118, or the like applied thereto that is indicative of where a corresponding contact surface 36 falls on an aggressiveness scale. For example, on a number scale from one to four, a number one marking 118 may indicate a cleansing surface 36c or some other least aggressive surface 36, while a number four marking 118 may indicate a sharp debridement surface 36a or some other most aggressive surface 36. Accordingly, a medical professional or other user may refer to a number 118 or the like when selecting a device 10 for use.

Referring to FIGS. 53-61, in selected embodiments, an aperture 78 may be omitted from a removable head 14 of a device 10 in accordance with the present invention. In such embodiments, a frame 34 of the head 14 may still include an aperture 76 to support securement to a main body 12. Such an aperture 76 may be shaped and sized to selectively receive a physical linkage 28, horn 28, or the like that conducts vibration, oscillation, and/or reciprocation from a main body 12 to a head 14.

Referring to FIGS. 62-72, in selected embodiments, a fluid system 16 may be separated from (e.g., located somewhat remotely with respect to) a main body 12 and/or head 14. For example, a fluid system 16 may comprise a pump (e.g., a peristaltic pump) that draws fluid from a fluid reservoir 44 (e.g., a saline bag) and urges the fluid through a relatively long conduit 50a to an aperture 78 in a head 14. In this manner, the flow of liquid to head 14 may be controlled (e.g., finely controlled) and may be set to a relatively low flow rate so as to avoid creating a puddling, liquid control, or liquid absorption problem for a user and/or patient. In such embodiments, a main body 12 may provide a channel 120 for receiving and engaging the conduit 50a. The channel 120 may grip the conduit 50a and ensure that the conduit 50a moves with the main body 12 and is not inadvertently pulled away or disengaged from a head 14.

In certain embodiments, a main body 12 and/or head 14 configured for use with a remote fluid reservoir 44 may also be configured for use with an on-board or attached reservoir 44. For example, a main body 12 may be shaped to house, extend over, or cradle at least a portion of a fluid reservoir 44 (e.g., at least a portion of a saline bullet). In such arrangements, a channel 120 may receive and secure a relatively short conduit 50b. Insertion of an outlet 88 of a fluid reservoir 44 into one end of the relatively short conduit 50b may secure or connect the fluid reservoir 44 to the rest of the device 10.

Referring to FIGS. 73-88, in selected embodiments, a head 14 may be configured for use on an open, deep wound or in undermined areas or tunneling wound-care situations. Accordingly, a contact surface 36 and frame 34 for such embodiments may be sized, shaped, and of sufficient length to support or facilitate that function. In certain embodiments, such a "deep pocket" head 14 may have an aperture 76 to support securement to a main body 12. Such an aperture 76 may be shaped and sized to selectively receive a physical linkage 28, horn 28, or the like that conducts vibration, oscillation, and/or reciprocation from a main body 12 to a head 14. In other embodiments, a deep pocket head 14 may be monolithically connected to (e.g., molded as a single unit with) a main body 12 or handle portion 12 that is shaped to cradle a finger of a user or fluid reservoir 44 as described hereinabove.

Figure 89:
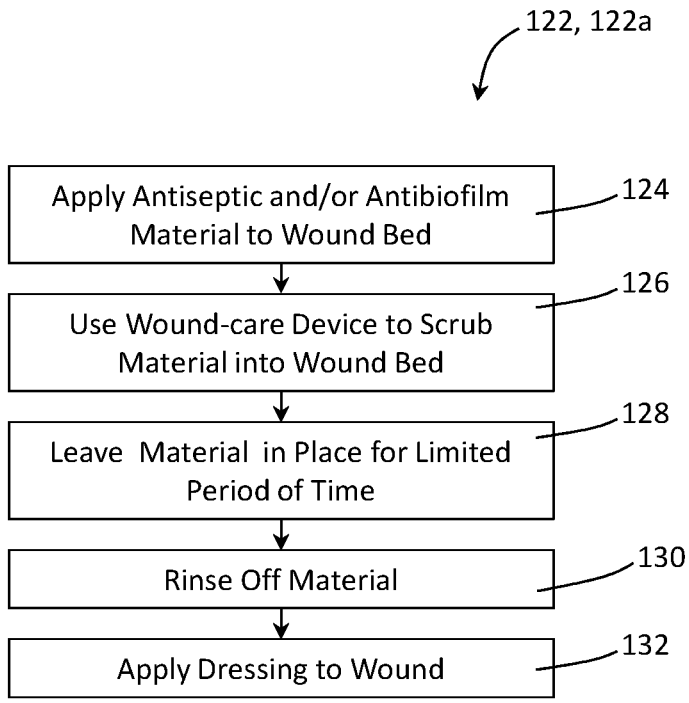
FIG. 89 is a block diagram of an alternative embodiment of a method for using a wound-care device in accordance with the present invention.
Figure 90:
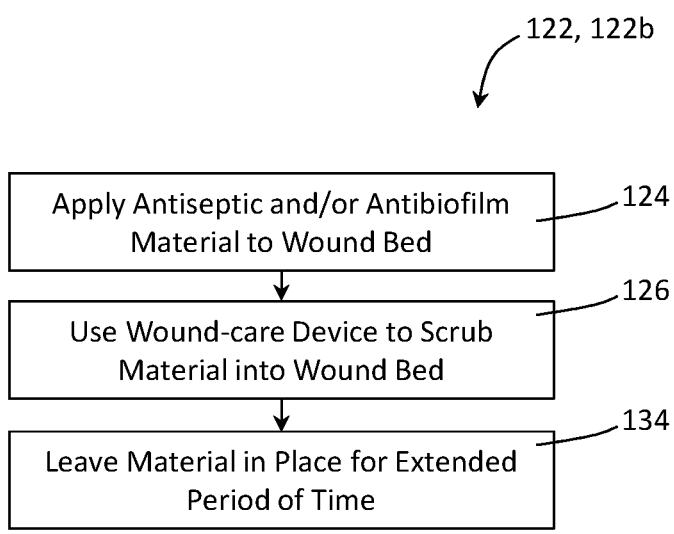
FIG. 90 is a block diagram of another alternative embodiment of a method for using a wound-care device in accordance with the present invention.

Referring to FIGS. 89 and 90, in selected embodiments, a wound-care device 10 in accordance with the present invention may be used in certain alternative methods 122. Such alternative methods 122 may be performed as stand-alone methods of wound care or may be incorporated into one or more other methods set forth hereinabove (e.g., between steps 72 and 74 in the method 58 of FIG. 5, between steps 72 and 110 in the method 108 of FIG. 15, between steps 72 and 110 in the method 112 of FIG. 16, or the like). In certain embodiments, one or more alternative methods 122 may involve applying an antiseptic and/or antibiofilm gel, paste, powder, or the like to a wound bed. This may assist in physically breaking up any biofilm (e.g., disrupt the Extra Polymeric Substance (EPS) of the biofilm) while, at the same time, actively working to (1) expose, lift up, flush away, and/or kill bacteria, and/or (2) otherwise chemically disrupt the biofilm.

For example, in one alternative method 122a, an antiseptic and/or antibiofilm material (e.g., gel, paste, powder, or the like) may be applied 124 to a wound bed. Thereafter, a wound-care device 10 in accordance with the present invention may be used to scrub 126 the material into the wound bed. The material may be left 128 in place for a limited period of time (e.g., a time period in a range from about 1 minute to about 15 minutes) and then rinsed 130 off. Thereafter, a dressing may be applied 132 if desired or necessary.

If an antiseptic and/or antibiofilm material is of a nature that prolonged application or exposure to a wound bed is beneficial and not potentially harmful, a different method 122b may be used. Specifically, after the material is applied 124 and scrubbed 126, it may be left 134 in place for an extended period of time. For example, a material may be left 134 in place for hours to days (e.g., up to seven days) in the case of an acutely infected wound. Accordingly, an antiseptic and/or antibiofilm material may affirmatively act to prevent bacterial growth, biofilm regrowth, and to provide an appropriate moist wound healing environment for an extended period of time.

In selected embodiments, an example of an antiseptic and/or antibiofilm material that may be rinsed 130 off after a few minutes may be hypochlorous acid, iodine, polyhexamethylene biguanide (PHMB), or the like. In certain embodiments, a preferred material may combine one or more antiseptics and/or antibiotics with one or more surfactants. Surfactants may break down the protective outer layer(s) of bacteria and/or viruses, kill bacteria or viruses, bind to dead or living bacteria and lift them off a wound bed, or the like. Therefore, one or more surfactants may be a valuable contributor to a gel, paste, power, or the like applied to a wound bed in one or more methods 58, 108, 112, 122 in accordance with the present invention.

EDTA is a metal chelator that may help break up biofilm and work well when combined with one or more surfactants. Adding EDTA to a combination of antiseptics such as iodine and PHMB may produce or enable a liquid material (e.g., an emulsified gel) suitable for application to a wound bed in one or more methods 58, 108, 112, 122 in accordance with the present invention (i.e., when combined with a manual and/or low sonic frequency electromechanical manipulation of a wound bed using a wound-care device 10).

An example of an antiseptic and/or antibiofilm material that may be left 134 in place for an extended period of time may be a slow-release iodine dressing, a PHMB dressing, or a combination or sub-combination of iodine, PHMB, EDTA, one or more surfactants, and the like. If such a combination is made in the context of a viscous gel or paste, it may be applied to a contact surface 36 of a head 14 and then scrubbed into a wound bed to break up biofilm bacteria and EPS and kill the bacteria.

Figure 91:
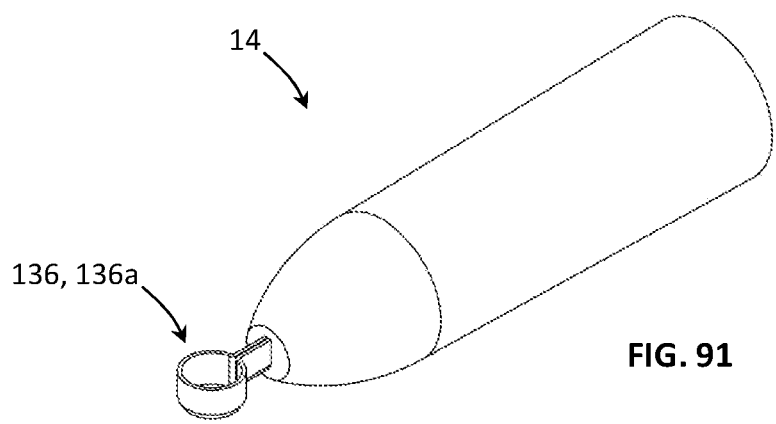
FIG. 91 is a perspective view of another alternative embodiment of a removable head for a wound-care device in accordance with the present invention.
Figure 92:
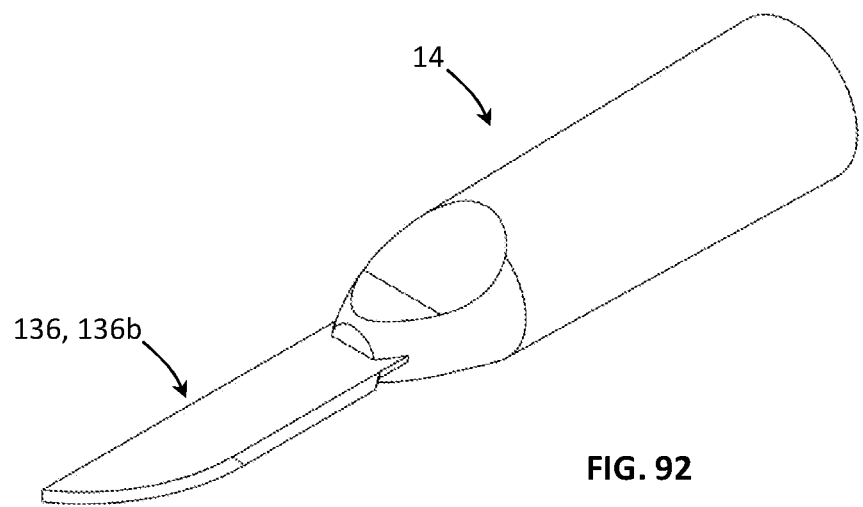
FIG. 92 is a perspective view of another alternative embodiment of a removable head for a wound-care device in accordance with the present invention.

Referring to FIGS. 91 and 92, in selected embodiments, certain heads 14 in accordance with the present invention may include a cutting element 136 (e.g., a curette 136a, scalpel 136b, or the like) rather than a contact surface 36. For example, a head 14 may configured as a removable head 14 having an aperture 76 for receiving a horn 28 or the like therewithin. Accordingly, when such a head 14 is applied to a horn 28 and the corresponding device 10 is turned "on," a motion generator 18 may cause a cutting element 136 to vibrate, oscillate, and/or reciprocate at a desired frequency. This motion may enable a user to remove dead tissue, callous material, or the like more easily or in a more controlled manner.

In view of the foregoing, a wound-care device 10 in accordance with the present invention may be supplied with or simply fit a variety of different heads 14 (e.g., one or more cleanings heads 14, one or more desloughing heads, one or more debriding heads 14, one or more cutting heads 14, or the like or a combination or sub-combination thereof). Accordingly, a user may select and install a particular head 14 to perform a particular task. When that task is complete, the user may remove that head 14 and install a different head 14 to perform a different task.

Figure 93:
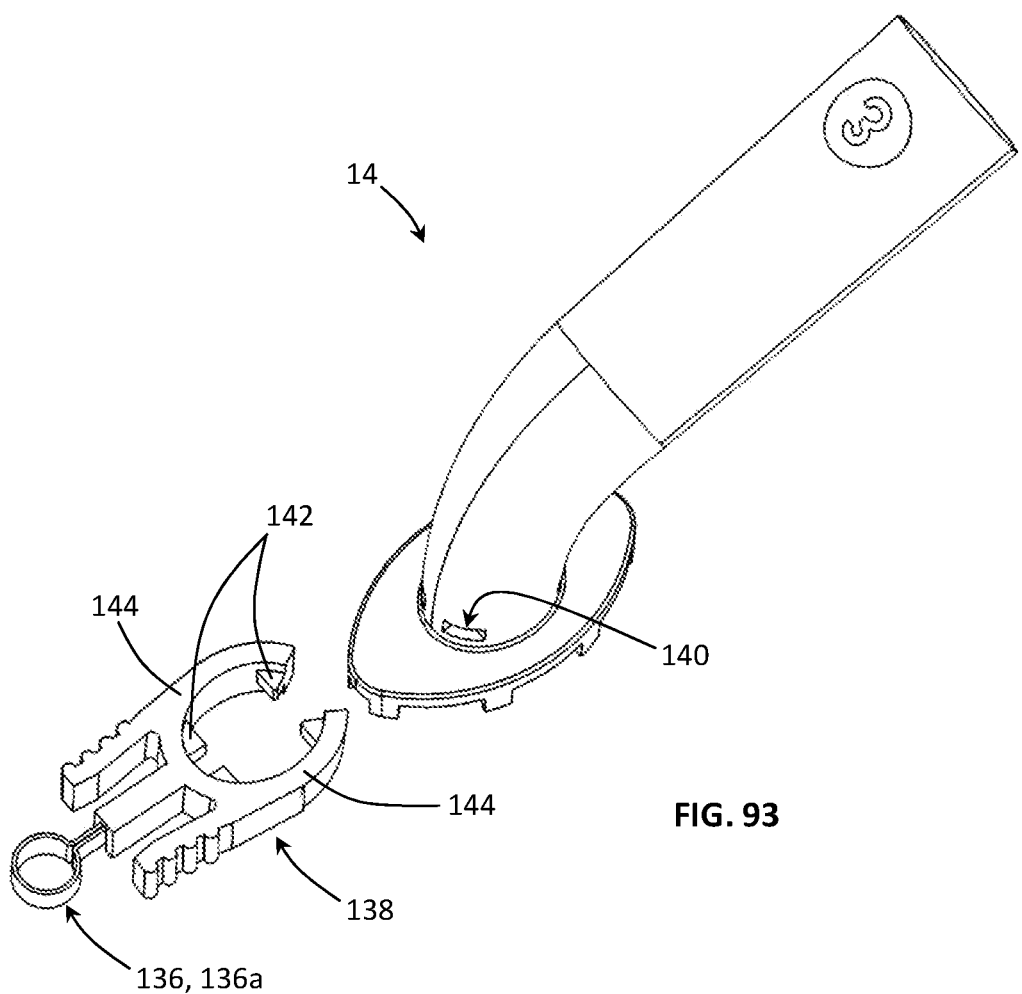
FIG. 93 is an exploded perspective view of another alternative embodiment of a removable head for a wound-care device in accordance with the present invention.
Figure 94:
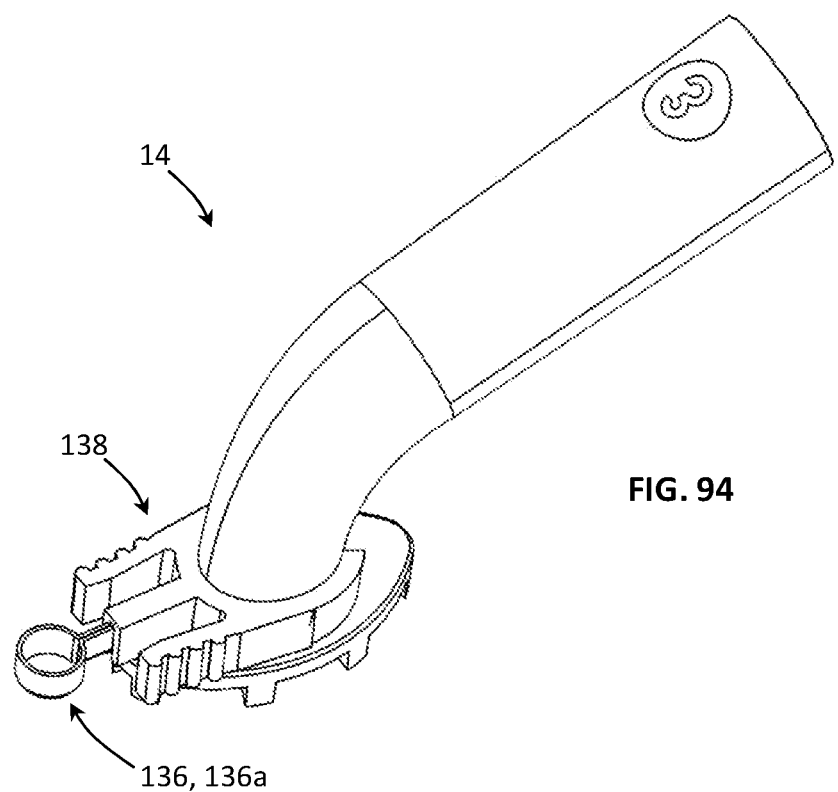
FIG. 94 is a perspective view of the removable head of FIG. 93 in an assembled configuration.
Figure 95:
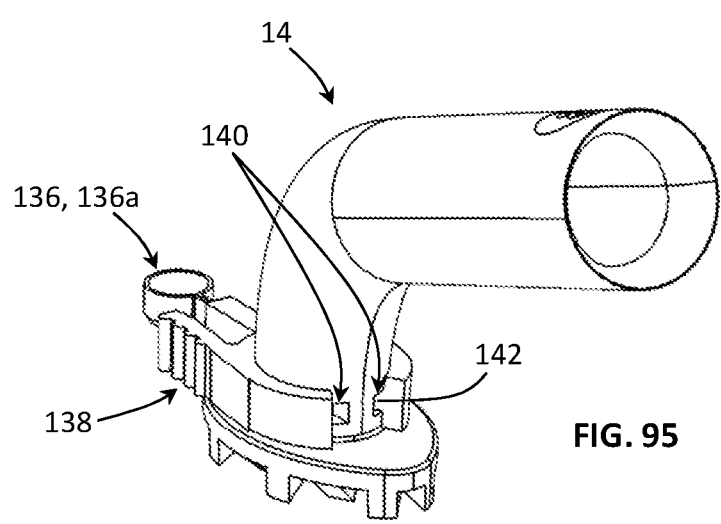
FIG. 95 is another perspective view of the removable head of FIG. 93 in an assembled configuration.
Figure 96:
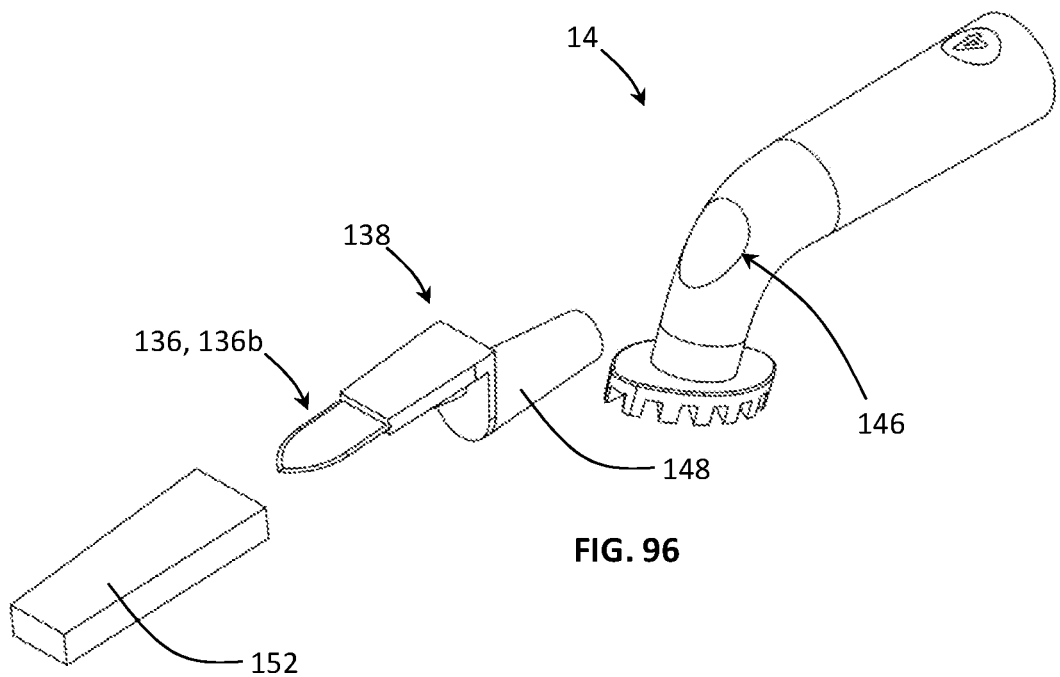
FIG. 96 is an exploded perspective view of another alternative embodiment of a removable head for a wound-care device in accordance with the present invention.
Figure 97:
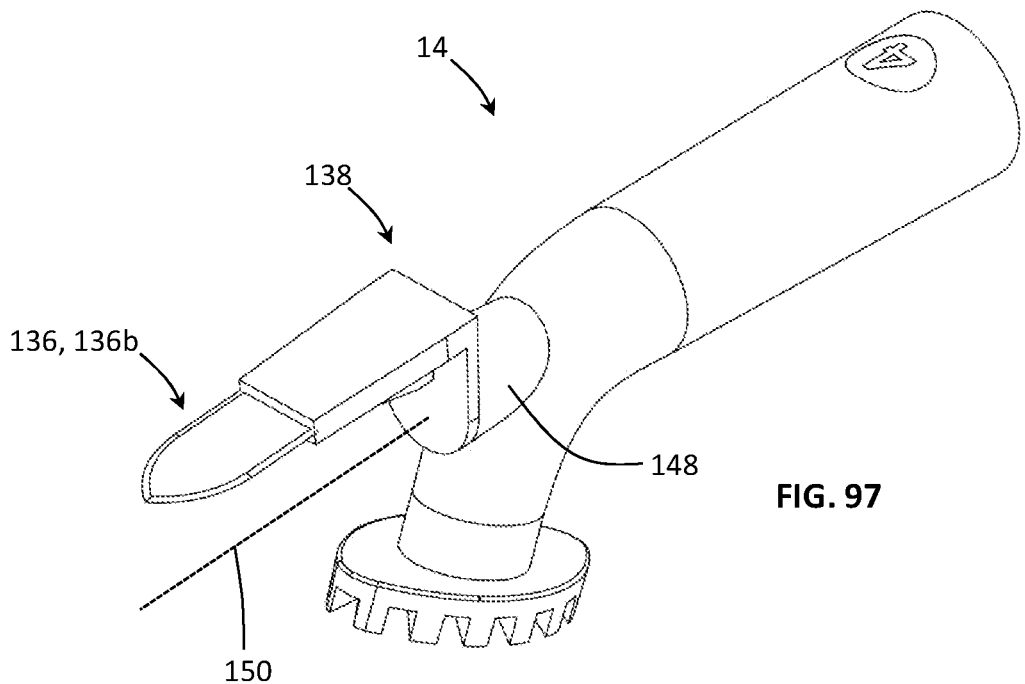
FIG. 97 is a perspective view of the removable head of FIG. 96 in an assembled configuration with the protective cover removed.
Figure 98:
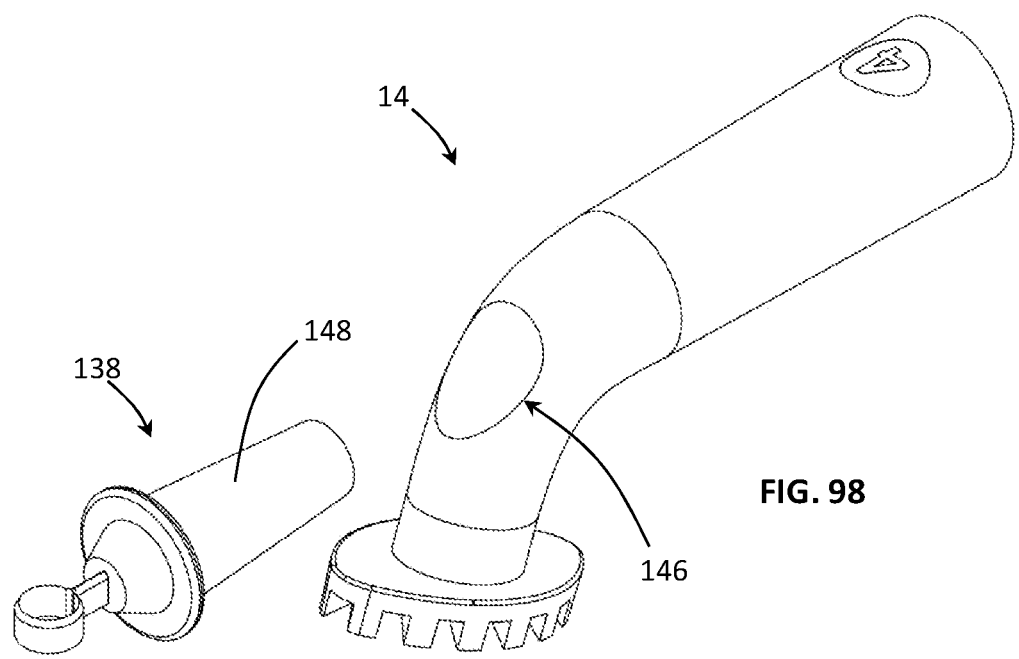
FIG. 98 is an exploded perspective view of another alternative embodiment of a removable head for a wound-care device in accordance with the present invention.
Figure 99:
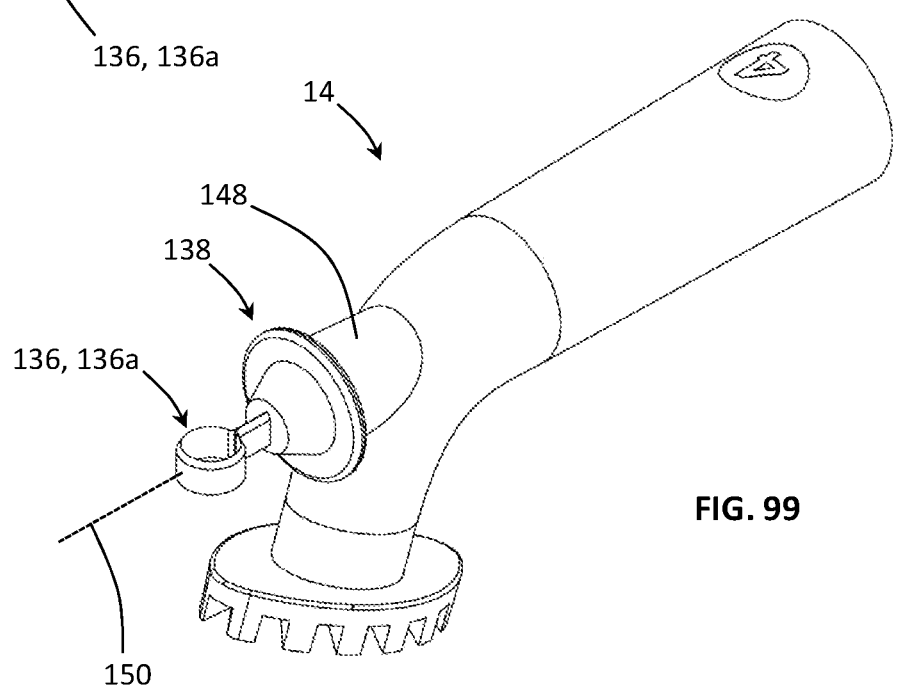
FIG. 99 is a perspective view of the removable head of FIG. 98 in an assembled configuration.

Referring to FIGS. 93-95, in selected embodiments, certain heads 14 in accordance with the present invention may include a cutting element 136 (e.g., a curette 136a, scalpel 136b, or the like) in addition to a contact surface 36. For example, a head 14 may configured to receive and retain a removable cutting element 136. Accordingly, when such a head 14 is applied to a horn 28 and the corresponding device 10 is turned "on," a motion generator 18 may cause a removable cutting device 136 to vibrate, oscillate, and/or reciprocate at a desired frequency.

In selected embodiments, an engagement mechanism 138 may selectively and/or removably secure a cutting element 136 to the rest of a head 14. For example, a main portion of a head 14 may include one or more recesses 140 and an engagement mechanism 138 may include one or more extensions 142 shaped to engage the one or more recesses 140. Clamping "jaws" 144 or the like may be manually flexed to open an engagement mechanism 138 sufficiently that it may engage the rest of a head 14 (e.g., sufficiently that one or more extensions 142 may be positioned so as to align with one or more recesses 140). When manual flexing of the engagement mechanism 138 ends, the engagement mechanism 138 may return to a closed position wherein the clamping jaws 144 thereof are in a neutral and/or undeflected position. The tendency of an engagement mechanism 138 to remain in the closed position may hold the one or more extensions 142 within the one or more recesses 140 and, thereby, selectively and/or removably secure the cutting element 136 to the rest of the head 14.

Referring to FIGS. 96-99, in selected embodiments, an engagement mechanism 138 may selectively and/or removably secure within an aperture 146 formed in a main portion of a head 14. For example, a main portion of a head 14 may include a tapered aperture 146 and an engagement mechanism 138 may include a tapered shaft 148 shaped to engage the tapered aperture 146. A frictional engagement between a tapered aperture 146 and a tapered shaft 148 of an engagement mechanism 138 may be sufficient to secure a cutting element 136 to the rest of a head 14.

In certain embodiments, an axis of symmetry 150 may exist between a tapered shaft 148 and a tapered aperture 146. Accordingly, before inserting an engagement mechanism 138 into a tapered aperture 146 of a head 14, a user may select a desired orientation for the corresponding cutting element 136. Once the orientation is selected and the tapered shaft 148 is seated within the tapered aperture 146, a friction engagement between the two components 146, 148 may resist relative rotation of one with respect to the other about the axis of symmetry 150.

In selected embodiments, a kit or system in accordance with the present invention may include a removable cover 152 for a cutting element 136. A removable cover 152 may protect a user and/or patient from inadvertent or unwanted contact with the cutting element 136 before the user is ready to use the cutting element 136. Alternatively, or in addition thereto, a cover 152 may preserve sterility of a cutting element 136 prior to use.

Figure 100:
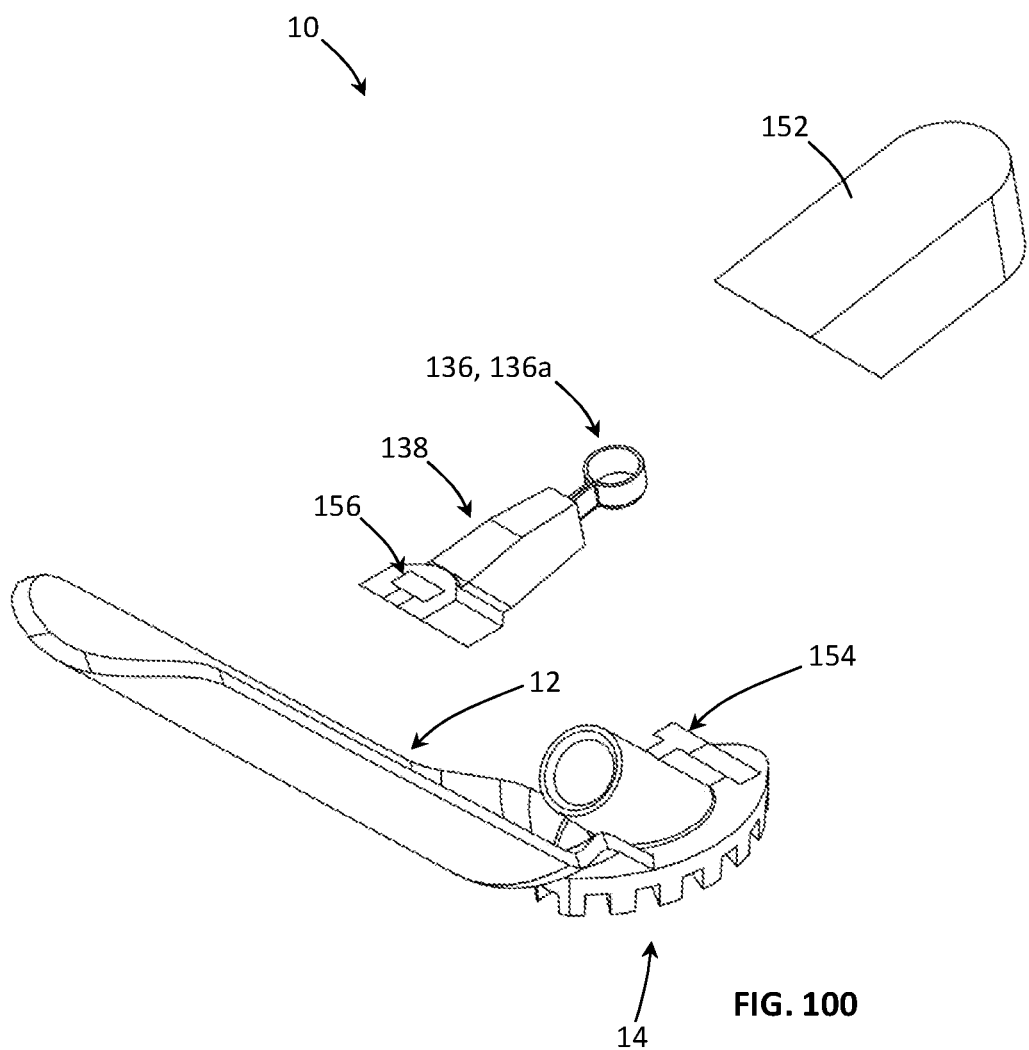
FIG. 100 is an exploded perspective view of another alternative embodiment of a wound-care device in accordance with the present invention.
Figure 101:
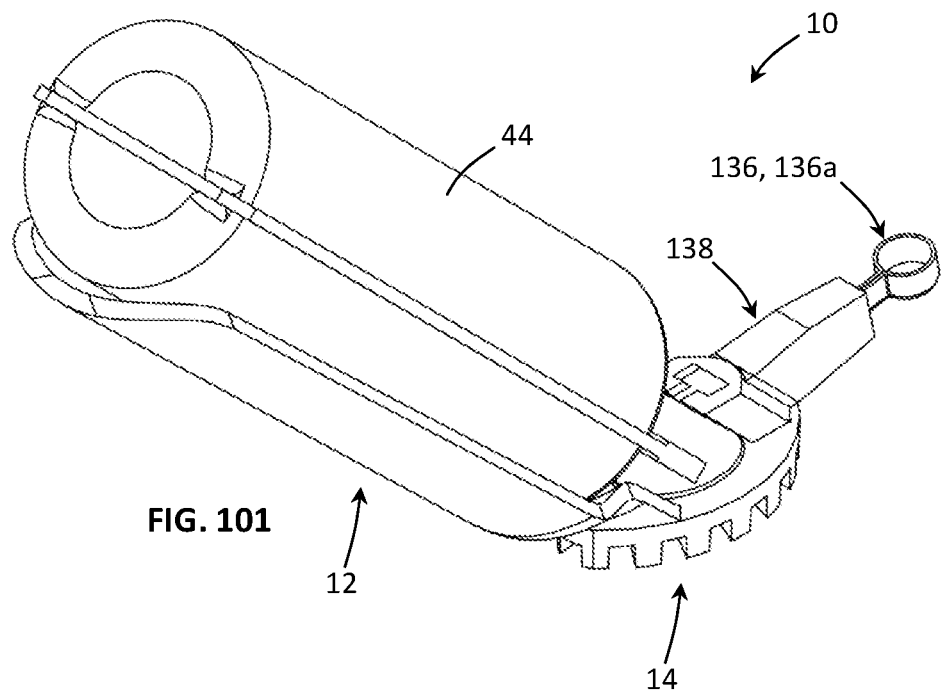
FIG. 101 is a perspective view of the wound-care device of FIG. 100 in an assembled configuration with the protective cover removed and a fluid reservoir installed.
Figure 102:
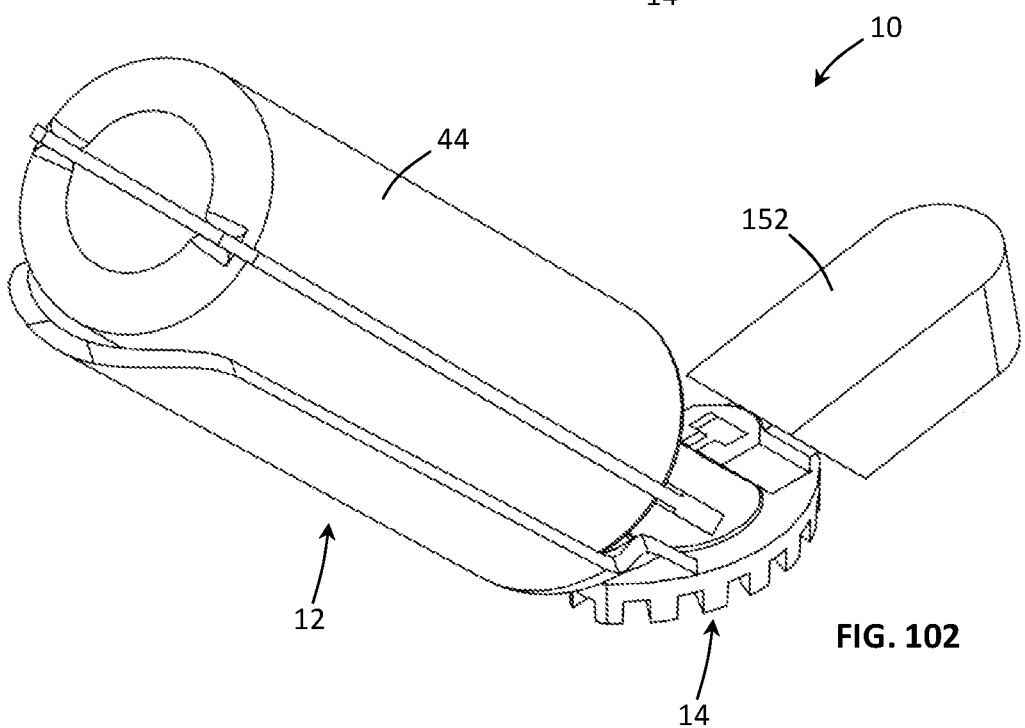
FIG. 102 is a perspective view of the wound-care device of FIG. 100 in an assembled configuration with a fluid reservoir installed.

Referring to FIGS. 100-102, in selected embodiments, a simplified main body 12 and head 14 combination may include a cutting element 136 (e.g., a curette 136a, scalpel 136b, or the like) in addition to a contact surface 36. In such embodiments, an engagement mechanism 138 may selectively and/or removably secure a cutting element 136 to the rest of a head 14. For example, a main portion of a head 14 may include a rail 154 and an engagement mechanism 138 may include an aperture 156 shape to engage the rail 154. When the aperture 156 is slid onto the rail 154, the engagement mechanism 138 may frictionally and/or mechanically engage the rail 154 and, thereby, selectively and/or removably secure the cutting element 136 to the rest of the head 14.

Figure 103:
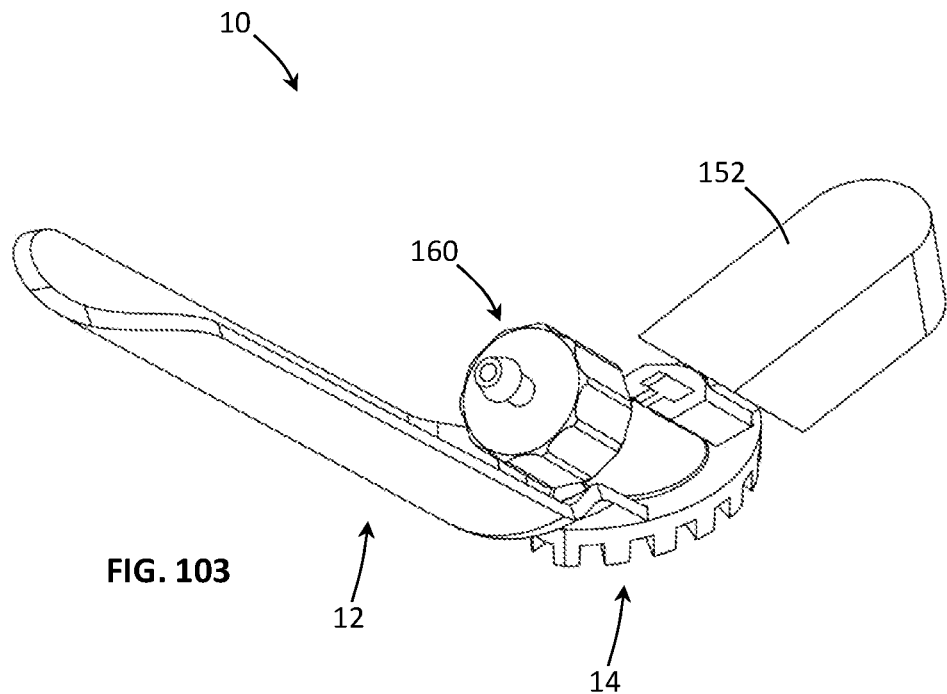
FIG. 103 is a perspective view of the wound-care device of FIG. 100 in an assembled configuration with a Luer-type connector installed.
Figure 104:
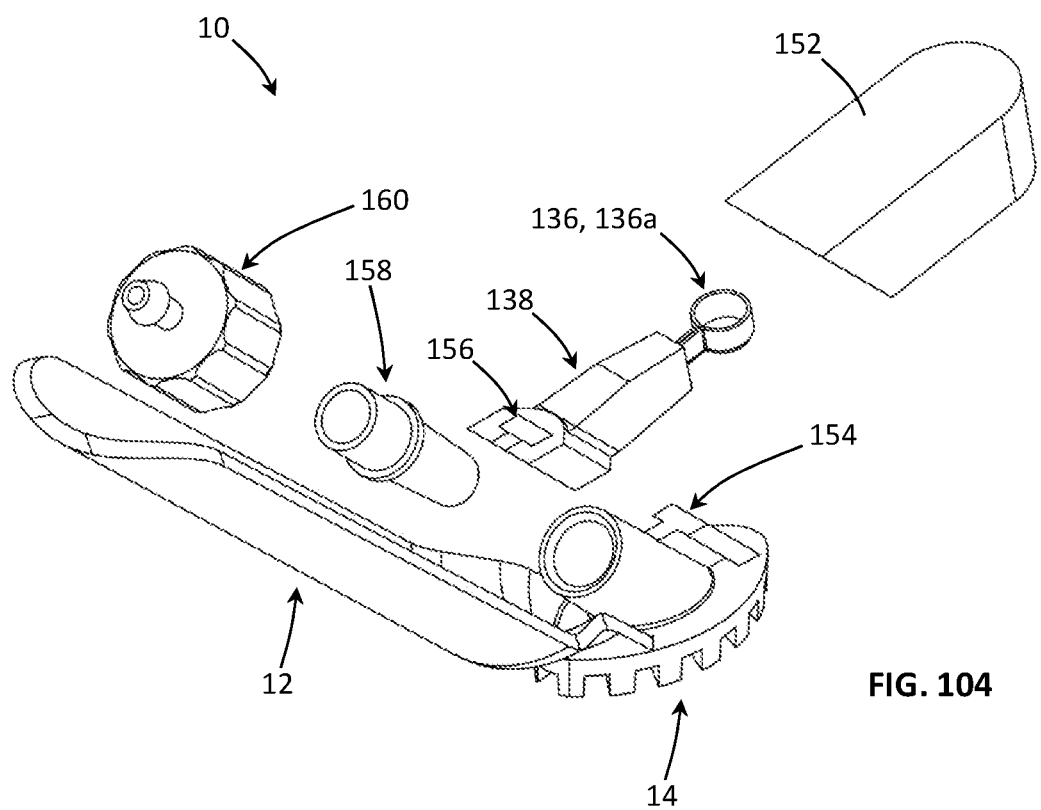
FIG. 104 is an exploded perspective view of the wound-care device of FIG. 103.

Referring to FIGS. 103 and 104, a wound-care device 10 may enable standard conduits 50 (e.g., standard or commonly available intravenous tubing, intravenous connectors, saline bags, or the like) to be used as part of a fluid system 16 in accordance with the present invention. For example, in certain embodiments, a kit corresponding to a wound-care device 10 may include an adaptor 158. The adaptor 158 may interface between an aperture 78 (e.g., an aperture 78 suitable for receiving an outlet 88 of a saline bullet) and a standard connector 160 (e.g., a Luer-type connector). That is, an adaptor 158 may have one end sized and shaped to be inserted within and frictionally engage an aperture 78 in a head and have a second, opposite end sized and shaped to receive and frictionally or mechanically engage a standard connector.

Figure 105:
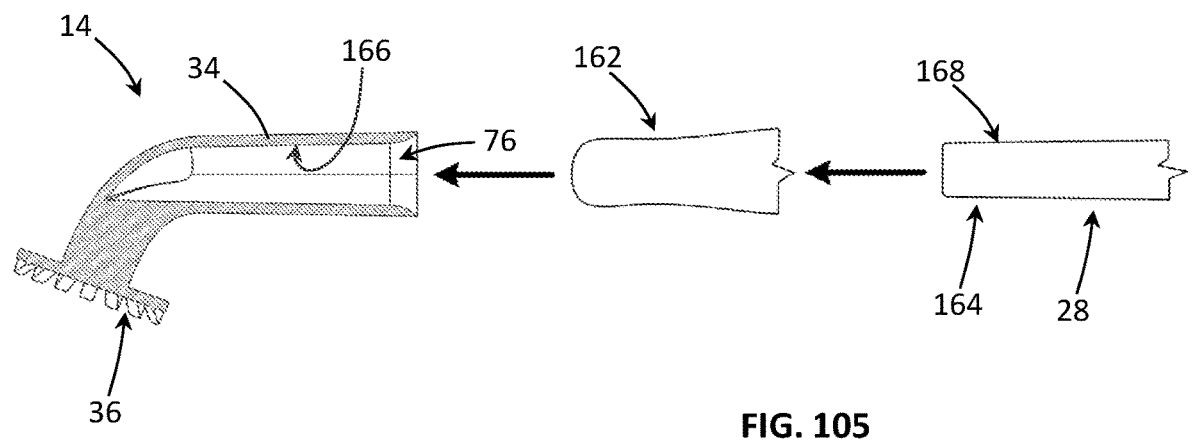
FIG. 105 is an exploded view of a head shown in cross-section, a portion of a sleeve, and a portion of a horn.
Figure 106:
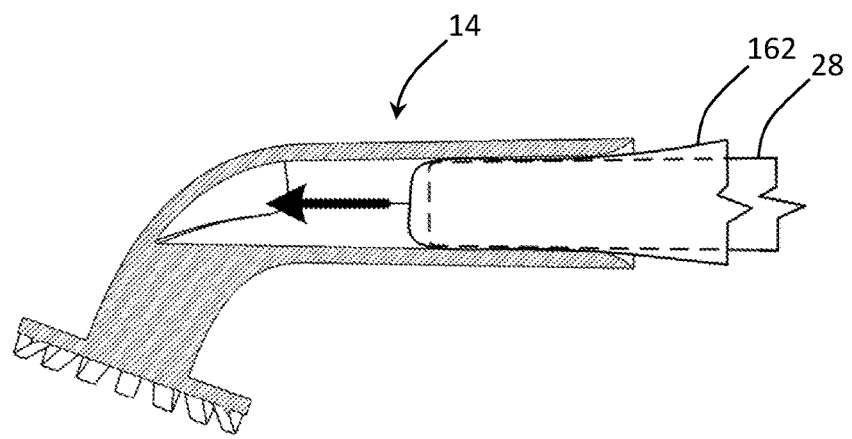
FIG. 106 is a partially assembled view of the head, sleeve, and horn of FIG. 105.

Referring to FIGS. 105 and 106, in selected embodiments, a device 10 may be provided or used in combination with one or more disposable (e.g., single use) sleeves 162 so that the device 10 or portions of the device 10 (e.g., a main body 12 or handle portion 12) may be reusable between patients safely without contamination of the device 10. In such embodiments, to configure a device 10 for use, a new and/or clean (e.g., sterile) head 14 and sleeve 162 may be applied to a main body 12 so that all surfaces coming in contact with a patient and a care-giver are clean. In certain embodiments, a sleeve 162 may cover a horn 28 and a housing 24 and a head 14 may slide over the sleeve 162 when it is installed on the horn 28.

That is, a head 14 may include a frame 34 and a contact surface 36. The frame 34 may engage the horn 28. For example, the frame 34 may have an aperture 76 shaped and sized to selectively receive (e.g., frictionally engage via mating tapers) the horn 28 and, thereby, conduct vibrations, oscillations, and/or reciprocations that originate with a motion generator 18 to the contact surface 36. When a sleeve 162 is used in such an arrangement, the aperture 76 in the frame 34 may receive therewithin the first end 164 of the horn 28 covered by the sleeve 162 such that a portion of the sleeve 162 is positioned between an interior surface 166 of the aperture 76 and an exterior surface 168 of the first end 164 of the horn 28.

The flowcharts of FIGS. 5, 15, 16, 89, and 90 illustrate the functionality and/or use of devices and systems in accordance with the present invention. It should be noted that, in some alternative implementations, the functions noted in the blocks may occur out of the order noted in the Figures. In certain embodiments, two blocks shown in succession may, in fact, be executed substantially concurrently, or the blocks may sometimes be executed in the reverse order, depending upon the functionality involved. Alternatively or in addition thereto, certain steps or functions may be omitted if not needed.

References in the specification to "one embodiment," "an embodiment," "an example embodiment," "selected embodiments," "certain embodiments," or the like, indicate that the embodiment or embodiments described may include a particular feature, structure, or characteristic, but every embodiment may not necessarily include the particular feature, structure, or characteristic. Such phrases are not necessarily referring to the same embodiment. Moreover, when physically possible or desired, it is understood that features, structures, or characteristic described in the context of one embodiment may be applied to or incorporated within one or more other embodiments. For example, any contact surface 36 shown or described in connection with one embodiment of a device 10 or head 14 may be used on any other embodiment of a device 10 or head 14.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method of treating a wound, the method comprising:
    obtaining a wound-care device comprising
        a handle having a first end and a second end opposite the first end,
        a disposable sleeve covering the handle and the first end thereof,
        a head secured to the first end of the handle and extending away from the first end of the handle, and
        the head comprising
            a frame,
            a first aperture formed in the frame and receiving therewithin the first end covered by the disposable sleeve such that a portion of the disposable sleeve is positioned between an interior surface of the first aperture and an exterior surface of the first end,
            a base having a front side and a back side, and
            a plurality of projections extending away from the base; and
    disturbing a wound bed of a patient by placing one or more projections of the plurality of projections in contact with the wound bed and moving, while the one or more projections are in contact with the wound bed, the wound-care device with respect to the wound bed.

2. The method of claim 1, wherein the frame, the base, and the plurality of projections are a monolithic unit formed of polymeric material.

3. The method of claim 2, wherein the wound-care device further comprises a motion generator positioned within the first end of the handle, the motion generator comprising an electric motor having a shaft with an eccentric weight secured thereto.

4. The method of claim 3, further comprising rotating, by the electric motor, the eccentric weight at a speed in a range from about 9,000 to about 36,000 revolutions per minute.

5. The method of claim 1, wherein:
the first aperture extends in a first direction;
the base extends in a second direction; and
the second direction departs from the first direction at an angle in a range from about 25 degrees to about 55 degrees.

6. The method of claim 1, wherein the head further comprises a cutting element positioned proximate the back side of the base.

7. The method of claim 1, wherein the head further comprises a second aperture bypassing the first aperture and extending through the base from the front side to the back side.

8. The method of claim 7, further comprising:
obtaining a container comprising an outlet and containing a fluid;
placing the outlet of the container in fluid communication with the second aperture; and
squeezing, during the disturbing, the container to expel at least a portion of the fluid through the outlet and through the second aperture.

9. The method of claim 1 wherein:
the wound-care device further comprises a motion generator positioned within the handle; and
the moving comprises inducing, by the motion generator, at least one of vibration, oscillation, or reciprocation of the plurality of projections at a frequency in a range of about 100 Hz to about 1000 Hz.

10. The method of claim 9, where the inducing comprises inducing, by the motion generator, the at least one of vibration, oscillation, or reciprocation at a frequency in a range of about 150 Hz to about 600 Hz.

11. A wound-care device comprising:
a handle having a first end and a second end opposite the first end;
the handle extending in a first direction from the first end to the second end;
a disposable sleeve covering the handle and the first end thereof;
a head secured to the first end of the handle and comprising
a frame,
a first aperture extending in the first direction into the frame and receiving therewithin the first end covered by the disposable sleeve such that a portion of the disposable sleeve is positioned between an interior surface of the first aperture and an exterior surface of the first end,
a base connected to the frame, and
a plurality of projections for disturbing a wound bed of a patient, the plurality of projections extending away from the base,
wherein the base extends in a second direction away from the first end of the handle and the second direction departs from the first direction at an angle in a range from about 25 degrees to about 55 degrees; and
a motion generator positioned within the handle and comprising an electric motor.

12. The wound-care device of claim 11, wherein:
the motion generator further comprises a shaft extending from the electric motor with an eccentric weight secured thereto; and
the motion generator is positioned within the first end of the handle.

13. The wound-care device of claim 11, wherein the frame, the base, and the plurality of projections are a monolithic unit formed of polymeric material.

14. The wound-care device of claim 11, wherein:
the base comprises a back side and a front side;
the plurality of projections project from the front side of the base; and
a second aperture extends through the base from the back side to the front side in a manner that bypasses the first aperture.

15. The wound-care device of claim 14, further comprising a container comprising an outlet and containing a fluid, wherein the outlet is connected to be in fluid communication with the second aperture.

16. The wound-care device of claim 12, wherein the electric motor is configured to rotate the eccentric weight at a speed in a range from about 9,000 to about 36,000 revolutions per minute.

17. The wound-care device of claim 11, wherein the motion generator is configured to vibrate, oscillate, or reciprocate the plurality of projections at a frequency in a range of about 100 Hz to about 1000 Hz.

18. The wound-care device of claim 17, wherein the motion generator is configured to vibrate, oscillate, or reciprocate the plurality of projections with an amplitude in a range from about 1 mm to about 10 mm.

19. A wound-care device comprising:
a handle having a tapered end and an opposite end, wherein the handle extends in a first direction from the opposite end to the tapered end;
a disposable sleeve covering the handle and the tapered end thereof;
a motion generator positioned within the tapered end and comprising an electric motor, the motion generator selectively inducing vibration or oscillation of the tapered end; and
a head selectively securable to the tapered end and comprising
a frame,
a first aperture extending in the first direction into the frame and having an interior surface tapering to provide a frictional engagement with the tapered end as the tapered end is inserted into the first aperture, the first aperture receiving therewithin the tapered end covered by the disposable sleeve such that a portion of the disposable sleeve is positioned between the interior surface of the first aperture and an exterior surface of the tapered end,
a base connected to the frame, and
a plurality of projections for disturbing a wound bed of a patient, the plurality of projections extending away from the base,
wherein the base extends in a second direction away from the tapered end of the handle and the second direction departs from the first direction at an angle in a range from about 25 degrees to about 55 degrees.

\* \* \* \* \*